US007056914B2

(12) United States Patent
Torrens Jover et al.

(10) Patent No.: US 7,056,914 B2
(45) Date of Patent: Jun. 6, 2006

(54) BENZOXAZINONE-DERIVED COMPOUNDS, THEIR PREPARATION AND USE AS MEDICAMENTS

(75) Inventors: Antoni Torrens Jover, Terrassa (ES); Jose Aurelio Castrillo Perez, Barcelona (ES); Jordi Frigola Constansa, Sant Just Desvern (ES); Josep Mas Prió, Rubi (ES); Alberto Dordal Zueras, Barcelona (ES); Maria Angeles Fisas Escasany, Barcelona (ES)

(73) Assignee: ESTEVE Laboratorios Dr. Esteve S.A., Barcelona (ES)

( * ) Notice: Subject to any disclaimer, the term of this patent is extended or adjusted under 35 U.S.C. 154(b) by 0 days.

(21) Appl. No.: 10/407,343

(22) Filed: Apr. 4, 2003

(65) Prior Publication Data

US 2004/0058920 A1    Mar. 25, 2004

(30) Foreign Application Priority Data

Apr. 9, 2002    (ES)    ................................ 200200813

(51) Int. Cl.
C07D 405/04    (2006.01)
C07D 405/14    (2006.01)
A61K 31/536    (2006.01)
A61P 3/04    (2006.01)

(52) U.S. Cl. ...................................... 514/230.5; 544/92
(58) Field of Classification Search ................. 544/92; 514/230.5
See application file for complete search history.

(56) References Cited

FOREIGN PATENT DOCUMENTS

| WO | WO 95/02405 | 1/1995 |
|----|-------------|--------|
| WO | WO 95/28397 | 10/1995 |
| WO | WO 97/19682 | 6/1997 |
| WO | WO 97/20823 | 6/1997 |
| WO | WO 97/25992 | 7/1997 |
| WO | WO 97/38665 | 10/1997 |
| WO | WO 98/24768 | 6/1998 |
| WO | WO 98/35957 | 8/1998 |
| WO | WO 98/40356 | 9/1998 |
| WO | WO 99/40091 | 8/1999 |
| WO | WO 00/20376 | 4/2000 |
| WO | WO 01/07409 | 2/2001 |
| WO | WO 01/13917 | 3/2001 |
| WO | WO 01/44213 | 6/2001 |
| WO | WO 01/64675 | 9/2001 |
| WO | WO 02/094825 | 11/2002 |

OTHER PUBLICATIONS

Hackh's Chemical Dictionary (Fourth Edition) 1969, pp. 25 and 193.*
http://www.encyclopedia.com/html/a1/aliphati.asp downloaded on Apr. 6, 2005.*
William, et al. "1-{1-[4-[(N-Acetyl-4-piperidinyl)oxy]-2-methoxybenzoyl]piperdin-4-yl}-4H-3,1-benzoxazin-2(1H)-one (L-371,257): A New, Orally Bioavailable, Non-Peptide Oxytocin Antagonist", J. Med. Chem., 1995, 38, pp. 4634-4636.
Williams, et al., "Nonpeptide Oxytocin Antagonists: Analogs of L-371,257 with Improved Potency", Bioorganic & Medicinal Chemistry Letters, 9, (1999), pp. 1311-1316.
"Multiple Receptors For Neuropeptide Y In The Hippocampus: Putative Roles In Seizures And Cognition", Redrobe et al., Brain Research Interactive, 848, 1999.
"Neuropeptide Y: A Possible Role In Hypertension?", Michel et al., Journal of Hypertension 1995.
"Identification Of A Novel Hypothalamic Neuropeptide Y Receptor Associated With Feeding Behavior", Hu et al., Journal of Biological Chemistry, vol. 271, No. 42, 1996.
"A Receptor Subtype Involved In Neuropeptide-Y-Induced Food Intake", Gerald, et al., Letters to Nature, vol. 382, 1996.
"1-{1-[4-[(N-Acetyl-4-piperidinyl)oxy]-2-methoxybenzoyl]piperidin-4-yl}-4H-3,1-benzoxazin-2(1H)-one (L-371,257): A New, Orally Bioavailable, Non-Peptide Ozytocin Antagonist", Williams et al., Jnl. Med. Chem., 38, 1995.
"Autoradiographic Reevaluation Of The Binding Properties Of $^{125}$I-[Leu$^{31}$,Pro$^{34}$]Peptide YY and $^{125}$I-Peptide YY$_{3-36}$ to Neuropeptide Y Receptor Subtypes In Rat Forebrain", Gobbi et al., Journal of Neurochemistry, 1999.
"Development of Orally Active Oxytocin Antagonists: Studies on 1-(1-{4-[1-(2-Methyl-1-oxidopyridin-3-ylmethyl)piperidin-4-yloxy]-2-methoxybenzoyl}piperidin-4-yl)-1,4-dihydrobenz[d][1,3]oxazin-2-one (L-372,662) and Related Pyridines", Bell et al., J. Med. Chem., 41, 1998.

* cited by examiner

Primary Examiner—Mark L Berch
Assistant Examiner—Kahsay Habte
(74) Attorney, Agent, or Firm—Perman & Green, LLP.

(57) ABSTRACT

The present invention relates to Benzoxazinone-derived compounds of general formula (I), methods for their preparation, medicaments comprising these compounds as well as their use for the preparation of a medicament for the treatment of humans or animals.

32 Claims, No Drawings

BENZOXAZINONE-DERIVED COMPOUNDS, THEIR PREPARATION AND USE AS MEDICAMENTS

The present invention relates to Benzoxazinone-derived compounds of general formula (I), methods for their preparation, medicaments comprising these compounds as well as their use for the preparation of a medicament for the treatment of humans or animals.

Neuropeptide Y (NPY), first isolated in porcine brain extracts (Tatemoto et. al. Nature 1982, 296, 659), is a 36-aminoacid peptide belonging to the family of pancreatic polypeptides, and is one of the most abundant peptides in the brain and in the central nervous system. In addition, NPY is also distributed in several parts of the peripheral nervous system.

Several studies suggest a significant role of NPY in food ingestion regulation and particularly in food dysfunctions like obesity, anorexia and bulimia. Specifically, NPY is a powerful stimulant of food ingestion. Thus, appetite is significantly increased when NPY is injected directly into the CNS of satiated mice (Clark J. T. et. al. Endocrinology 1984, 115, 427; Levine A. S. et. al. Peptides 1984, 5, 1025; Stanley B. G. et. al. Life Sci. 1984, 35, 2635; Stanley B. G. et. al. Proc. Nat. Acad. Sci. USA 1985, 82, 3940). On the other hand, NPY may play a role in cognitive function regulation, e. g. memory (Flood J. F. et. al. Brain Res. 1987, 421, 280; Redrobe J. P. et. Al. Brain Res. 1999, 848, 153), and be active in anxiety (Heilig M. et. al. Reg. Peptides 1992, 41, 61) and depression (Heilig M. et. al. Eur. J. Pharmacol. 1988, 147, 465) processes.

NPY is also distributed in the peripheral system. Some studies suggest that it might be involved in hypertensive (Michal M. C: et. al. J. Hypertens. 1995, 13, 153), and analgesic (Gehlert D. R. Life Sci. 1994, 55, 551) processes, among others.

The endogenous proteins that constitute NPY-binding receptors have been widely studied. Several have been cloned and expressed. At present, six different receptor subtypes, named Y1 to Y6, are recognized (Hispkind P. A. et. al. Annu. Rep. Med. Chem. 1996, 31, 1; Grunemar L. et. al. TIPS Reviews., 15, 153). Each NPY receptor subtype is generally associated to a different biological activity. For example, Y2 receptor is involved in the induction of convulsions in rats (Dumont Y. et. al. Brit. J. Pharmacol. 2000, 129, 1075).

The most recently identified receptor is Y5 (Hu et. al. J. Biol. Chem. 1996, 271, 26315). There is evidence that Y5 receptor has a unique pharmacological profile related to food ingestion as compared to the other receptor subtypes. The fact that [D-Trp$^{32}$]NPY peptide, a selective Y5-receptor agonist with no affinity for Y1 receptor, stimulates food ingestion in rats (Gerald C. et. al. Nature, 1996, 382, 168), supports the hypothesis that Y5 receptor is related to exaggerated food consumption. Consequently, compounds antagonizing Y5 receptor should be effective to inhibit food ingestion and very useful to control diseases like obesity or disorders of food ingestion, preferably anorexia or bulimia, or diabetes, artritis or epilepsy.

Several NPY5 non-peptidic antagonists have been described. Thus, 2-aminoquinazoline derivatives [PCT Int. Appl. WO 9720823, 1997 (Novartis AG)], sulfonamides [PCT Int. Appl. WO 9719682, 1997 (Synaptic Pharmaceutical Corp.)], pyrazoles [PCT Int. Appl. WO 9824768, 1998 (Banyu Pharmaceutical Co., Ltd)], aminopyridines [PCT Int. Appl. WO 9840356, 1998 (Banyu Pharmaceutical Co., Ltd)], N-aralkyl-2-tetralinamines [PCT Int. Appl. WO 0020376, 2000 (Ortho McNeil Pharmaceutical Inc.)], several amides [PCT Int. Appl. WO 9835957, 1998 (Bayer Corp.)], pyridine and pyrimidine derivatives [PCT Int. Appl. WO 9940091, 1999 (Amgen Inc.)], carbazoles [PCT Int. Appl. WO 0107409, 2001 (Astra Zeneca AB.)], and spiroisoquinolinones [PCT Int. Appl. WO 0113917, 2001 (Bristol-Myers Squibb Co.)], have been prepared.

Benzoxazinone derivatives having biological activity related to NPY receptors are not disclosed in the state of the art. The only background of benzoxazinone derivatives with biological activity refer to P2X7-receptor antagonists, useful for the treatment of inflammatory, immune or cardiovascular diseases [PCT Int. Appl. WO 01044213, 2001 (Astrazeneca AB)], to oxytocin receptor antagonists, useful in tocology [PCT Int. Appl. WO 9725992, 1997 (Merck Co., Inc.)], to α1c adrenergic receptor antagonists [PCT Int. Appl. WO 9528397, 1955 (Merck Co., Inc.)], or to pharnesilprotein-transferase enzyme inhibitors [PCT Int. Appl. WO 9738665, 1997 (Merck Co., Inc.)].

Thus, it was an object of the present invention to provide novel compounds that are suitable in particular as active substances in medicaments, preferably in medicaments for the regulation of neuropeptide Y receptors, particularly preferably of neuropeptide Y 5 (NPY5) receptor, for the regulation of food ingestion, preferably for the prophylaxis and/or treatment of disorders of food ingestion, preferably obesity, anorexia, bulimia or diabetes, for the prophylaxis and/or treatment of disorders of the peripheral nervous system, disorders of the central nervous system, anxiety, depression, cognitive disorders, preferably memory disorders, cardiovascular diseases, pain, epilepsy, arthritis, hypertensive syndrom, inflammatory diseases, immune diseases and other NPY5 mediated disorders in mammals, including man.

Said object was achieved by providing benzoxazinone-derived compounds of general formula (I),

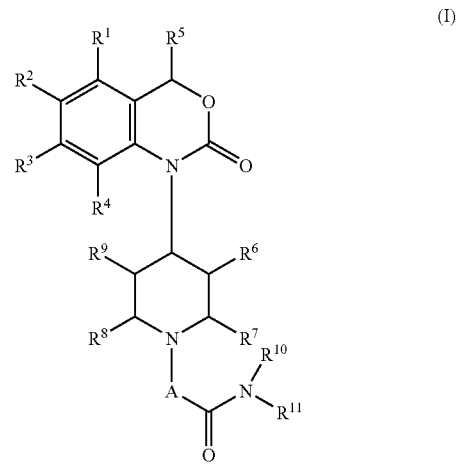

wherein $R^1$, $R^2$, $R^3$, $R^4$ are each independently selected from the group consisting of hydrogen, halogen, an unbranched or branched, saturated or unsaturated, optionally at least mono-substituted aliphatic radical, a saturated or unsaturated, optionally at least mono-substituted, optionally at least one heteroatom as ring member containing cycloaliphatic radical, which may be bonded via an optionally at least mono-substituted alkylene group and/or may be condensed with an optionally at least mono-substituted mono- or polycyclic ring-system, an optionally at least mono-substituted aryl- or heteroaryl radical, which may be bonded via an optionally at least mono-substituted alkylene group and/or may be condensed with an optionally at least mono-substituted mono- or polycyclic ringsystem, a nitro, cyano, —$OR^{12}$, —$OC(=O)R^{13}$, —$SR^4$, —$SOR^{14}$, —$SO_2R^{14}$, —NH—$SO_2R^{14}$, —$SO_2NH_2$ and —$NR^{15}R^{16}$ moiety, $R^5$ represents hydrogen, an unbranched or branched, saturated or unsaturated, optionally at least mono-substituted aliphatic radical or a saturated or unsaturated, optionally at least mono-substituted, optionally at least one heteroatom as ring member containing cycloaliphatic radical, $R^6$, $R^7$, $R^8$, $R^9$ are each independently selected from the group consisting of hydrogen, an unbranched or branched, saturated or unsaturated, optionally at least mono-substituted aliphatic radical, a saturated or unsaturated, optionally at least mono-substituted, optionally at least one heteroatom as ring member containing cycloaliphatic radical, a cyano and a —$COOR^{17}$ moiety, A represents a bridge member —$CHR^{18}$— or —$CHR^{18}$—$CH_2$—, $R^{10}$ represents hydrogen, an unbranched or branched, saturated or unsaturated, optionally at least mono-substituted aliphatic radical, a saturated or unsaturated, optionally at least mono-substituted, optionally at least one heteroatom as ring member containing cycloaliphatic radical or an optionally at least mono-substituted aryl- or heteroaryl radical, which may be bonded via an optionally at least mono-substituted alkylene group and/or may be condensed with an optionally at least mono-substituted mono- or polycyclic ring-system, $R^{11}$ represents an unbranched or branched, saturated or unsaturated, optionally at least mono-substituted aliphatic radical, a saturated or unsaturated, optionally at least mono-substituted, optionally at least one heteroatom as ring member containing cycloaliphatic radical, which may be bonded via an optionally at least mono-substituted alkylene group and/or may be condensed with an optionally at least mono-substituted mono- or polycyclic ringsystem, or an optionally at least mono substituted aryl- or heteroaryl radical, which may be bonded via an optionally at least mono-substituted alkylene group and/or may be condensed with an optionally at least mono-substituted mono- or polycyclic ringsystem, or $R^{10}$ and $R^{11}$ together with the bridging nitrogen atom form an optionally at least mono-substituted, saturated, unsaturated or aromatic heterocyclic ring that may contain at least one further heteroatom as a ring member and/or may be condensed with an optionally at least mono-substituted mono- or polycyclic ringsystem, $R^{12}$ represents hydrogen, an unbranched or branched, saturated or unsaturated, optionally at least mono-substituted aliphatic radical, a saturated or unsaturated, optionally at least mono-substituted, optionally at least one heteroatom as ring member containing cycloaliphatic radical, which may be bonded via an optionally at least mono-substituted alkylene group and/or may be condensed with an optionally at least mono-substituted mono- or polycyclic ring-system, or an optionally at least mono-substituted aryl- or heteroaryl radical, which may be bonded via an optionally at least mono-substituted alkylene group and/or may be condensed with an optionally at least mono-substituted mono- or polycyclic ring-system, $R^{13}$ represents hydrogen, an unbranched or branched, saturated or unsaturated, optionally at least mono-substituted aliphatic radical, a saturated or unsaturated, optionally at least mono-substituted, optionally at least one heteroatom as ring member containing cycloaliphatic radical, which may be bonded via an optionally at least mono-substituted alkylene group and/or may be condensed with an optionally at least mono-substituted mono- or polycyclic ring-system, or an optionally at least mono-substituted aryl- or heteroaryl radical, which may be bonded via an optionally at least mono-substituted alkylene group and/or may be condensed with an optionally at least mono-substituted mono- or polycyclic ring-system, $R^{14}$ represents an unbranched or branched, saturated or unsaturated, optionally at least mono-substituted aliphatic radical, a saturated or unsaturated, optionally at least mono-substituted, optionally at least one heteroatom as ring member containing cycloaliphatic radical, which may be bonded via an optionally at least mono-substituted alkylene group and/or may be condensed with an optionally at least mono-substituted mono- or polycyclic ring-system, or an optionally at least mono-substituted aryl- or heteroaryl radical, which may be bonded via an optionally at least mono-substituted alkylene group and/or may be condensed with an optionally at least mono-substituted mono- or polycyclic ring-system, $R^{15}$ and $R^{16}$ are each independently selected from the group consisting of hydrogen, an unbranched or branched, saturated or unsaturated, optionally at least mono-substituted aliphatic radical, a saturated or unsaturated, optionally at least mono-substituted, optionally at least one heteroatom as ring member containing cycloaliphatic radical, which may be bonded via an optionally at least mono-substituted alkylene group and/or may be condensed with an optionally at least mono-substituted mono- or polycyclic ring-system, or an optionally at least mono-substituted aryl- or heteroaryl radical, which may be bonded via an optionally at least mono-substituted alkylene group and/or may be condensed with an optionally at least mono-substituted mono- or polycyclic ring-system, or $R^{15}$ and $R^{16}$ together with the bridging nitrogen atom form a saturated, unsaturated or aromatic heterocyclic ring, which may be at least mono-substituted and/or contain at least one further heteroatom as ring member, $R^{17}$ represents hydrogen, an unbranched or branched, saturated or unsaturated, optionally at least mono-substituted aliphatic radical, a saturated or unsaturated, optionally at least mono-substituted, optionally at least one heteroatom as ring member containing cycloaliphatic radical or an optionally at least mono-substituted aryl- or heteroaryl radical, which may be bonded via an optionally at least mono-substituted alkylene group and/or may be condensed with an optionally at least mono-substituted mono- or polycyclic ring-system, $R^{18}$ represents hydrogen, an unbranched or branched, saturated or unsaturated, optionally at least mono-substituted aliphatic radical, a saturated or unsaturated, optionally at least mono-substituted, optionally at least one heteroatom as ring member containing cycloaliphatic radical or an optionally at least mono-substituted aryl- or heteroaryl radical, which may be bonded via an optionally at least mono-substituted alkylene group and/or may be condensed with an optionally at least mono-substituted mono- or polycyclic ring-system, optionally in form of one of their stereoisomers, preferably enantiomers or diastereomers, their racemates or in form of a mixture of at least two of its stereoisomers, preferably enantiomers or diastereomers, in any mixing ratio, or physiologically acceptable salts thereof, or solvates, respectively.

A mono- or polycyclic ring-system according to the present invention means a mono- or polycyclic hydrocarbon ring-system that may be saturated, unsaturated or aromatic. If the ring system is polycyclic, each of its different rings may show a different degree of saturation, i.e. it may be saturated, unsaturated or aromatic. Optionally each of the rings of the mono- or polycyclic ring system may contain one or more heteroatoms as ring members, which may be identical or different and which can preferably be selected from the group consisting of N, O, S and P, more preferably be selected from the group consisting of N, O and S. Preferably the polycyclic ring-system may comprise two rings that are condensed. The rings of the mono- or polycyclic ring-system are preferably 5- or 6-membered.

If one or more of the residues $R^1$–$R^{18}$ represents an aliphatic radical, which is substituted by one or more substituents, unless defined otherwise, each of these substituents may preferably be selected from the group consisting of hydroxy, halogen, branched or unbranched $C_{1-4}$-alkoxy, branched or unbranched $C_{1-4}$-perfluoroalkoxy, branched or unbranched $C_{1-4}$-perfluoroalkyl, amino, carboxy, amido, cyano, nitro, —$SO_2NH_2$, —CO—$C_{1-4}$-alkyl, —SO—$C_{1-4}$-alkyl, —$SO_2$—$C_{1-4}$-alkyl, —NH—$SO_2$—$C_{1-4}$-alkyl, wherein the $C_{1-4}$-alkyl may in each case be branched or unbranched, an unsubstituted or at least mono-substituted phenyl or naphthyl radical and an unsubstituted or at least mono-substituted furanyl-, thienyl-, pyrrolyl-, imidazolyl-, pyrazolyl-, pyridinyl-, pyrimidinyl-, quinolinyl- and isoquinolinyl radical, more preferably be selected from the group consisting of hydroxy, F, Cl, Br, methoxy, ethoxy, $CF_3$ and an unsubstituted phenyl radical. If any one of the above mentioned substitutents itself is at least mono-substituted, said substituents may preferably be selected from the group consisting of F, Cl, methyl and methoxy.

If one or more of the residues $R^1$–$R^{18}$ represents a cycloaliphatic radical, which is substituted by one or more substituents, unless defined otherwise, each of these substituents may preferably be selected from the group consisting of hydroxy, halogen, branched or unbranched $C_{1-4}$-alkyl, branched or unbranched $C_{1-4}$-alkoxy, branched or unbranched $C_{1-4}$-perfluoroalkoxy, phenoxy, benzoyl, cyclohexyl, branched or unbranched $C_{1-4}$-perfluoroalkyl, —$NR^AR^B$ wherein $R^A$, $R^B$ are each independently selected from the group consisting of H, a branched or unbranched $C_{1-4}$-alkyl-radical, —$CH_2$—$CH_2$—OH and phenyl, carboxy, amido, cyano, nitro, —$SO_2NH_2$, —CO—$C_{1-4}$-alkyl, —CO—$OC_{1-4}$-alkyl, —SO—$C_{1-4}$-alkyl, —$SO_2$—$C_{1-4}$-alkyl, —NH—$SO_2$—$C_{1-4}$-alkyl, wherein $C_{1-4}$-alkyl may in each case be branched or unbranched, unsubstituted or at least mono-substituted phenyl or naphthyl and unsubstituted or at least mono-substituted furanyl-, thienyl-, pyrrolyl-, imidazolyl-, pyrazolyl-, pyridinyl-, pyrimidinyl-, quinolinyl- and isoquinolinyl radical, more preferably be selected from the group consisting of hydroxy, F, Cl, Br, methyl, ethyl, methoxy, ethoxy, benzoyl, phenoxy, cyclohexyl, —$CF_3$, —CO—$CH_3$, —CO—$OCH_3$, —$NR^AR^B$ wherein $R^A$, $R^B$ are each independently selected from the group consisting of H, a branched or unbranched $C_{1-4}$-alkyl-radical, —$CH_2$—$CH_2$—OH and phenyl, and an unsubstituted phenyl radical. If any one of the above mentioned substitutents itself is at least mono-substituted, said substituents may preferably be selected from the group consisting of F, Cl, methyl and methoxy.

If one or more of the residues $R^1$–$R^4$ and $R^{10}$–$R^{18}$ comprises an alkylene group, which is substituted by one or more substituents, unless defined otherwise, each of these substituents may preferably be selected from the group consisting of hydroxy, halogen, branched or unbranched $C_{1-4}$-alkoxy, branched or unbranched $C_{1-4}$-perfluoroalkoxy, branched or unbranched $C_{1-4}$-perfluoroalkyl, amino, carboxy, amido, cyano, nitro, —$SO_2NH_2$, —CO—$C_{1-4}$-alkyl, —SO—$C_{1-4}$-alkyl, —$SO_2$—$C_{1-4}$-alkyl, —NH—$SO_2$—$C_{1-4}$-alkyl, wherein $C_{1-4}$-alkyl may be branched or unbranched, an unsubstituted or at least mono-substituted phenyl or naphthyl radical and an unsubstituted or at least mono-substituted furanyl-, thienyl-, pyrrolyl-, imidazolyl-, pyrazolyl-, pyridinyl-, pyrimidinyl-, quinolinyl- and isoquinolinyl radical, more preferably be selected from the group consisting of hydroxy, F, Cl, Br, methoxy, ethoxy, $CF_3$ and unsubstituted phenyl. If any one of the above mentioned substitutents itself is at least mono-substituted, said substituents may preferably be selected from the group consisting of F, Cl, methyl and methoxy.

If one or more of the residues $R^1$–$R^4$ and $R^{10}$–$R^{18}$ comprises a mono- or polycyclic ringsystem, which is substituted by one or more substituents, unless defined otherwise, each of these substituents may preferably be selected from the group consisting of hydroxy, halogen, branched or unbranched $C_{1-4}$-alkyl, branched or unbranched $C_{1-4}$-alkoxy, branched or unbranched $C_{1-4}$-perfluoroalkoxy, branched or unbranched $C_{1-4}$-perfluoroalkyl, amino, carboxy, amido, cyano, keto, nitro, —$SO_2NH_2$, —CO—$C_{1-4}$-alkyl, —SO—$C_{1-4}$-alkyl, —$SO_2$—$C_{1-4}$-alkyl, —NH—$SO_2$—$C_{1-4}$-alkyl, wherein $C_{1-4}$-alkyl may be branched or unbranched, an unsubstituted or at least mono-substituted phenyl or naphthyl radical and unsubstituted or at least mono-substituted furanyl-, thienyl-, pyrrolyl-, imidazolyl-, pyrazolyl-, pyridinyl-, pyrimidinyl-, quinolinyl- and isoquinolinyl, more preferably from the group consisting of hydroxy, F, Cl, Br, methyl, ethyl, methoxy, ethoxy, $CF_3$, keto, cyano and an unsubstituted phenyl radical. If any one of the above mentioned substitutents itself is at least mono-substituted, said substituents may preferably be selected from the group consisting of F, Cl, methyl and methoxy.

If one or more of the residues $R^1$–$R^4$ and $R^{10}$–$R^{18}$ represents or comprises an aryl radical, which is substituted by one or more substituents, unless defined otherwise, each of these substituents may preferably be selected from the group consisting of hydroxy, halogen, branched or unbranched $C_{1-4}$-alkoxy, branched or unbranched $C_{1-4}$-alkyl, branched or unbranched $C_{1-4}$-perfluoroalkoxy, phenoxy, benzoyl, cyclohexyl, branched or unbranched $C_{1-4}$-perfluoroalkyl, $NR^AR^B$ wherein $R^A$, $R^B$ are each independently selected from the group consisting of H, a branched or unbranched $C_{1-4}$-alkyl-radical, —$CH_2$—$CH_2$—OH and phenyl, carboxy, amido, cyano, nitro, —$SO_2NH_2$, —CO—$C_{1-4}$-alkyl, —CO—$OC_{1-4}$-alkyl, —SO—$C_{1-4}$-alkyl, —$SO_2$—$C_{1-4}$-alkyl, —NH—$SO_2$—$C_{1-4}$-alkyl, wherein $C_{1-4}$-alkyl may be branched or unbranched, an unsubstituted or at least mono-substituted phenyl or naphthyl radical and unsubstituted or at least mono-substituted furanyl-, thienyl-, pyrrolyl-, imidazolyl-, pyrazolyl-, pyridinyl-, pyrimidinyl-, quinolinyl- and isoquinolinyl radical, more preferably be selected from the group consisting of hydroxy, F, Cl, Br, methyl, ethyl, cyano, methoxy, ethoxy, benzoyl, phenoxy, cyclohexyl, $CF_3$, —CO—$CH_3$, —CO—$OCH_3$, —$NR^AR^B$ wherein $R^A$, $R^B$ are each independently selected from the group consisting of H, a branched or unbranched $C_{1-4}$-alkyl-radical, —$CH_2$—$CH_2$—OH and phenyl, and an unsubstituted phenyl radical. If any of the above mentioned substitutents itself is at least mono-substituted, said substituents may preferably be selected from the group consisting of F, Cl, methyl and methoxy.

If one or more of the residues $R^1$–$R^4$ and $R^{10}$–$R^{18}$ represents or comprises a heteroaryl radical, which is substituted by one or more substituents, unless defined otherwise, each of these substituents may preferably be selected from the group consisting of hydroxy, halogen, branched or unbranched $C_{1-4}$-alkoxy, branched or unbranched $C_{1-4}$-alkyl, branched or unbranched $C_{1-4}$-perfluoroalkoxy, phenoxy, benzoyl, cyclohexyl, branched or unbranched $C_{1-4}$-perfluoroalkyl, $NR^AR^B$ wherein $R^A$, $R^B$ are each independently selected from the group consisting of H, a branched or unbranched $C_{1-4}$-alkyl-radical, —$CH_2$—$CH_2$—OH and phenyl, carboxy, amido, cyano, nitro, —$SO_2NH_2$, —CO—$C_{1-4}$-alkyl, —CO—$OC_{1-4}$-alkyl, SO—$C_{1-4}$-alkyl, $SO_2$-$C_{1-4}$-alkyl, —NH—$SO_2$—$C_{1-4}$-alkyl, wherein $C_{1-4}$-alkyl may be branched or unbranched, an unsubstituted or at least mono-substituted phenyl or naphthyl radical and an unsubstituted or at least mono-substituted furanyl-, thienyl-, pyrrolyl-, imidazolyl-, pyrazolyl-, pyridinyl-, pyrimidinyl-, quinolinyl- and isoquinolinyl radical, more preferably be selected from the group consisting of hydroxy, F, Cl, Br, methyl, ethyl, cyano, methoxy, ethoxy, benzoyl, phenoxy, cyclohexyl, $CF_3$, —CO—$CH_3$, —CO—$OCH_3$, —$NR^AR^B$ wherein $R^A$, $R^B$ are each independently selected from the group consisting of H, a branched or unbranched $C_{1-4}$-alkyl-radical, —$CH_2$—$CH_2$—OH and phenyl, and an unsubstituted phenyl radical. If any one of the above mentioned substitutents itself is at least mono-substituted, said substituents may preferably be selected from the group consisting of F, Cl, methyl and methoxy.

If $R^{10}$ and $R^{11}$ and/or $R^{15}$ and $R^{16}$ form a heterocyclic ring, which is substituted by one or more substituents, unless defined otherwise, each of these substituents may preferably be selected from the group consisting of hydroxy, halogen, branched or unbranched $C_{1-4}$-alkoxy, branched or unbranched $C_{1-4}$-alkyl, branched or unbranched $C_{1-4}$-perfluoroalkoxy, branched or unbranched $C_{1-4}$-perfluoroalkyl, amino, carboxy, amido, cyano, nitro, —$SO_2NH_2$, —CO—$C_{1-4}$-alkyl, —SO—$C_{1-4}$-alkyl, —$SO_2$—$C_{1-4}$-alkyl, —NH—$SO_2$—$C_{1-4}$-alkyl, wherein $C_{1-4}$-alkyl may be branched or unbranched, an unsubstituted or at least mono-substituted phenyl or naphthyl radical and an unsubstituted or at least mono-substituted furanyl-, thienyl-, pyrrolyl-, imidazolyl-, pyrazolyl-, pyridinyl-, pyrimidinyl-, quinolinyl- and isoquinolinyl radical, more preferably be selected from the group consisting of hydroxy, F, Cl, Br, methoxy, ethoxy, methyl, $CF_3$ and an unsubstituted phenyl radical. If any of the above mentioned substitutents itself is at least mono-substituted, said substituents may preferably be selected from the group consisting of F, Cl, methyl and methoxy.

If $R^{10}$ and $R^{11}$ and/or $R^{15}$ and $R^{16}$ form a heterocyclic ring, which contains one or more further heteroatoms as ring members, unless defined otherwise, each of these heteroatoms may preferably be selected from the group consisting of N, O and S, more preferably from the group consisting of N and O.

If one or more of the residues $R^1$–$R^{18}$ represents a cycloaliphatic radical, which contains one or more heteroatoms as ring members, unless defined otherwise, each of these heteroatoms may preferably be selected from the group consisting of N, O, S and P, more preferably from the group consisting of N, O and S.

If one or more of the residues $R^1$–$R^4$ and $R^{10}$–$R^{18}$ represents or comprises an heteroaryl radical, which contains one or more heteroatoms as ring members, unless defined otherwise, each of these heteroatoms may preferably be selected from the group consisting of N, O, S and P, more preferably from the group consisting of N, O and S.

Preferred compounds of general formula (I) are those, wherein $R^1$, $R^2$, $R^3$, $R^4$ are each independently selected from the group consisting of H, F, Cl, Br, an unbranched or branched, saturated or unsaturated, optionally at least mono-substituted $C_{1-6}$-aliphatic radical, a saturated or unsaturated, optionally at least mono-substituted, optionally at least one heteroatom as ring member containing $C_{3-8}$-cycloaliphatic radical, which may be bonded via an optionally at least mono-substituted $C_{1-6}$-alkylene group and/or may be condensed with an optionally at least mono-substituted mono- or polycyclic ring-system, an optionally at least mono-substituted, 5- or 6-membered aryl- or heteroaryl radical, which may be bonded via an optionally at least mono-substituted $C_{1-6}$-alkylene group and/or may be condensed with an optionally at least mono-substituted mono- or polycyclic ringsystem, a nitro, cyano, —$OR^{12}$, —$OC(=O)R^{13}$, —$SR^{14}$, —$SOR^{14}$, —$SO_2R^{14}$, —NH—$SO_2R^{14}$, —$SO_2NH_2$ and —$NR^{15}R^{16}$ moiety, $R^5$ represents hydrogen, an unbranched or branched, saturated or unsaturated, optionally at least mono-substituted $C_{1-6}$-aliphatic radical or a saturated or unsaturated, optionally at least mono-substituted, optionally at least one heteroatom as ring member containing $C_{3-8}$-cycloaliphatic radical, $R^6$, $R^7$, $R^8$, $R^9$ are each independently selected from the group consisting of hydrogen, an unbranched or branched, saturated or unsaturated, optionally at least mono-substituted $C_{1-6}$-aliphatic radical, a saturated or unsaturated, optionally at least mono-substituted, optionally at least one heteroatom as ring member containing $C_{3-8}$-cycloaliphatic radical, a cyano and a $COOR^{17}$ moiety, A represents a bridge member —$CHR^{18}$— or —$CHR^{18}$—$CH_2$—, $R^{10}$ represents hydrogen, an unbranched or branched, saturated or unsaturated, optionally at least mono-substituted $C_{1-6}$-aliphatic radical, a saturated or unsaturated, optionally at least mono-substituted, optionally at least one heteroatom as ring member containing $C_{3-8}$-cycloaliphatic radical or an optionally at least mono-substituted, 5- or 6-membered aryl- or heteroaryl radical, which may be bonded via an optionally at least mono-substituted $C_{1-6}$-alkylene group and/or may be condensed with an optionally at least mono-substituted mono- or polycyclic ring-system, $R^{11}$ represents an unbranched or branched, saturated or unsaturated, optionally at least mono-substituted $C_{1-6}$-aliphatic radical, a saturated or unsaturated, optionally at least mono-substituted, optionally at least one heteroatom as ring member containing $C_{3-8}$-cycloaliphatic radical, which may be bonded via an optionally at least mono-substituted $C_{1-6}$-alkylene group and/or may be condensed with an optionally at least mono-substituted mono- or polycyclic ringsystem, or an optionally at least mono substituted 5- or 6-membered aryl- or heteroaryl radical, which may be bonded via an optionally at least mono-substituted $C_{1-6}$-alkylene group and/or may be condensed with an optionally at least mono-substituted mono- or polycyclic ringsystem, or $R^{10}$ and $R^{11}$ together with the bridging nitrogen atom form an optionally at least mono-substituted, saturated, unsaturated or aromatic, 5- or 6-membered heterocyclic ring, which may contain at least one further heteroatom as a ring member and/or may be condensed with an optionally at least mono-substituted mono- or polycyclic ringsystem, $R^{12}$ represents hydrogen, an unbranched or branched, saturated or unsaturated, optionally at least mono-substituted $C_{1-6}$-aliphatic radical, a saturated or unsaturated, optionally at least mono-substituted, optionally at least one heteroatom containing as ring member $C_{3-8}$-cycloaliphatic radical, which may be bonded via an optionally at least mono-substituted $C_{1-6}$-alkylene group and/or may be condensed with an optionally at least mono-substituted mono- or polycyclic ring-system, or an optionally at least mono-substituted, 5- or 6-membered aryl- or heteroaryl radical, which may be bonded via an optionally at least mono-substituted $C_{1-6}$-alkylene group and/or may be condensed with an optionally at least mono-substituted mono- or polycyclic ring-system, $R^{13}$ represents hydrogen, an unbranched or branched, saturated or unsaturated, optionally at least mono-substituted $C_{1-6}$-aliphatic radical, a saturated or unsaturated, optionally at least mono-substituted, optionally at least one heteroatom as ring member containing $C_{3-8}$-cycloaliphatic radical, which may be bonded via an optionally at least mono-substituted $C_{1-6}$-alkylene group and/or may be condensed with an optionally at least mono-substituted mono- or polycyclic ring-system, or an optionally at least mono-substituted, 5- or 6-membered aryl- or heteroaryl radical, which may be bonded via an optionally at least mono-substituted $C_{1-6}$-alkylene group and/or may be condensed with an optionally at least mono-substituted mono- or polycyclic ring-system, $R^{14}$ represents an unbranched or branched, saturated or unsaturated, optionally at least mono-substituted $C_{1-6}$-aliphatic radical, a saturated or unsaturated, optionally at least mono-substituted, optionally at least one heteroatom as ring member containing $C_{3-8}$-cycloaliphatic radical, which may be bonded via an optionally at least mono-substituted $C_{1-6}$-alkylene group and/or may be condensed with an optionally at least mono-substituted mono- or polycyclic ring-system, or an optionally at least mono-substituted, 5- or 6-membered aryl- or heteroaryl radical, which may be bonded via an optionally at least mono-substituted $C_{1-6}$-alkylene group and/or may be condensed with an optionally at least mono-substituted mono- or polycyclic ring-system, $R^{15}$ and $R^{16}$ each are independently selected from the group consisting of hydrogen, an unbranched or branched, saturated or unsaturated, optionally at least mono-substituted $C_{1-6}$-aliphatic radical, a saturated or unsaturated, optionally at least mono-substituted, optionally at least one heteroatom as ring member containing $C_{3-8}$-cycloaliphatic radical, which may be bonded via an optionally at least mono-substituted $C_{1-6}$-alkylene group and/or may be condensed with an optionally at least mono-substituted mono- or polycyclic ring-system, or an optionally at least mono-substituted, 5- or 6-membered aryl- or heteroaryl radical, which may be bonded via an optionally at least mono-substituted $C_{1-6}$-alkylene group and/or may be condensed with an optionally at least mono-substituted mono- or polycyclic ring-system, or $R^{15}$ and $R^{16}$ together with the bridging nitrogen atom form a saturated, unsaturated or aromatic, 5- or 6-membered heterocyclic ring, which may be at least mono-substituted and/or contain at least one further heteroatom as a ring member, $R^{17}$ represents hydrogen, an unbranched or branched, saturated or unsaturated, optionally at least mono-substituted $C_{1-6}$-aliphatic radical, a saturated or unsaturated, optionally at least mono-substituted, optionally at least one heteroatom as ring member containing $C_{3-8}$-cycloaliphatic radical or an optionally at least mono-substituted, 5- or 6-membered aryl- or heteroaryl radical, which may be bonded via an optionally at least mono-substituted $C_{1-6}$-alkylene group and/or may be condensed with an optionally at least mono-substituted mono- or polycyclic ring-system, $R^{18}$ represents hydrogen, an unbranched or branched, saturated or unsaturated, optionally at least mono-substituted $C_{1-6}$-aliphatic radical, a saturated or unsaturated, optionally at least mono-substituted, optionally at least one heteroatom as ring member containing $C_{3-8}$-cycloaliphatic radical or an optionally at least mono-substituted, 5- or 6-membered aryl- or heteroaryl radical, which may be bonded via an optionally at least mono-substituted $C_{1-6}$-alkylene group and/or may be condensed with an optionally at least mono-substituted mono- or polycyclic ring-system, optionally in form of one of their stereoisomers, preferably enantiomers or diastereomers, their racemates or in form of a mixture of at least two of its stereoisomers, preferably enantiomers or diastereomers, in any mixing ratio, or physiologically acceptable salts thereof, or solvates, respectively.

Particularly preferred are compounds of general formula (I), wherein $R^1$, $R^2$, $R^3$, $R^4$ are each independently selected from the group consisting of H, F, Cl, Br, a saturated, branched or unbranched, optionally at least mono-substituted $C_{1-3}$-aliphatic radical, a saturated, optionally at least mono-substituted, optionally at least one heteroatom as ring member containing $C_5$- or $C_6$-cycloaliphatic radical, which may be bonded via an optionally at least mono-substituted $C_1$- or $C_2$-alkylene group, a nitro, cyano, —$OR^{12}$, —OC(=O)$R^{13}$, —$SR^{14}$ and —$NR^{15}R^{16}$ moiety, preferably be selected from the group consisting of H, F, Cl, $CH_3$, $CH_2CH_3$, $CF_3$, $CF_2CF_3$, cyclopentyl, cyclohexyl, nitro, cyano and —$OR^{12}$ and the remaining residues $R^5$–$R^{18}$ and A have the meaning given above, optionally in form of one of their stereoisomers, preferably enantiomers or diastereomers, their racemates or in form of a mixture of at least two of its stereoisomers, preferably enantiomers or diastereomers, in any mixing ratio, or physiologically acceptable salts thereof, or solvates, respectively.

Also particularly preferred are compounds of general formula (I), wherein $R^5$ represents H or a branched or unbranched $C_{1-3}$-alkyl radical, preferably H, $CH_3$ or $CH_2CH_3$, and the remaining residues $R^6$–$R^{18}$ and A have the meaning given above, optionally in form of one of their stereoisomers, preferably enantiomers or diastereomers, their racemates or in form of a mixture of at least two of its stereoisomers, preferably enantiomers or diastereomers, in any mixing ratio, or physiologically acceptable salts thereof, or solvates, respectively.

Also particularly preferred are compounds of general formula (I), wherein $R^6$, $R^7$, $R^8$, $R^9$ are each independently selected from the group consistihg of H, a branched or unbranched $C_{1-3}$-alkyl radical, a cyano and a $COOR^{17}$ moiety, preferably selected from the group consisting of H, $CH_3$, $CH_2CH_3$ and a cyano moiety, and the remaining residues $R^{10}$–$R^{18}$ and A have the meaning given above, optionally in form of one of their stereoisomers, preferably enantiomers or diastereomers, their racemates or in form of a mixture of at least two of its stereoisomers, preferably enantiomers or diastereomers, in any mixing ratio, or physiologically acceptable salts thereof, or solvates, respectively.

Also particularly preferred are compounds of general formula (I), wherein $R^{10}$ represents hydrogen or a branched or unbranched $C_{1-4}$-alkyl radical, and the remaining residues $R_{11}$–$R^{18}$ and A have the meaning given above, optionally in form of one of their stereoisomers, preferably enantiomers or diastereomers, their racemates or in form of a mixture of at least two of its stereoisomers, preferably enantiomers or diastereomers, in any mixing ratio, or physiologically acceptable salts thereof, or solvates, respectively.

Also particularly preferred are compounds of general formula (I), wherein $R^{11}$ is selected from the group consisting of an unsubstituted phenyl radical, a phenyl radical optionally at least mono-substituted with a branched or unbranched $C_{1-4}$-alkyl-radical, a branched or unbranched $C_{1-4}$-alkoxy-radical, a branched or unbranched $C_{1-4}$-perfluoroalkyl-radical, a branched or unbranched $C_{1-4}$-perfluoroalkoxy-radical, F, Cl, Br, cyclohexyl, phenyl, phenoxy, phenylthio, benzoyl, cyano, —C(=O)$C_{1-2}$-alkyl, —C(=O)O$C_{1-2}$-alkyl, -carboxy, —CH(OH)(phenyl), —NR$^A$R$^B$ wherein R$^A$, R$^B$ are each independently selected from the group consisting of H, a branched or unbranched $C_{1-4}$-alkyl-radical, —CH$_2$—CH$_2$—OH and an unsubstituted phenyl radical, an unsubstituted thiazole radical, a group of general formula (A)

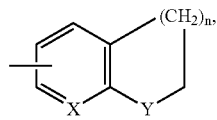
(A)

wherein n is 1 or 2,

X represents CH or N,

Y represents CH$_2$, O, N—R$^C$, CH—OH or C(=O),

R$^C$ is H or a branched or unbranched $C_{1-4}$-alkyl radical, a group of formula (B),

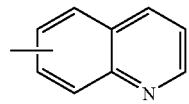
(B)

a group of formula (C),

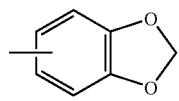
(C)

a group of general formula (D),

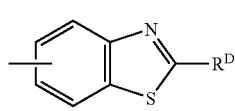
(D)

wherein R$_D$ is H or a branched or unbranched $C_{1-4}$-alkyl radical and a group of general formula (E),

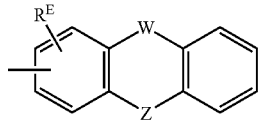
(E)

wherein

R$^E$ represents H, a branched or unbranched $C_{1-4}$-alkyl radical or a branched or unbranched $C_{1-4}$-alkoxy radical, W represents a bond between the two aromatic rings, CH$_2$, CH—OH or C(=O), Z represents CH$_2$, O, S, CH—OH, C(=O) or N—R$^F$ where R$^F$ represents H or a branched or unbranched $C_{1-4}$-alkyl-radical, and the remaining residues $R^{12}$–$R^{18}$ and A have the meaning given above, optionally in form of one of their stereoisomers, preferably enantiomers or diastereomers, their racemates or in form of a mixture of at least two of its stereoisomers, preferably enantiomers or diastereomers, in any mixing ratio, or physiologically acceptable salts thereof, or solvates, respectively.

Also particularly preferred are compounds of general formula (I), wherein $R^{10}$ and $R^{11}$ together with the bridging nitrogen atom form a saturated, 6-membered heterocyclic ring, which is at least mono-substituted with a methyl radical and/or condensed with an unsubstituted or at least mono-substituted phenyl- or cyclohexyl-radical, said phenyl- or cyclohexyl-radical preferably being at least mono-substituted with F and/or OCH$_3$, and the remaining residues $R^{12}$–$R^{18}$ and A have the meaning given above, optionally in form of one of their stereoisomers, preferably enantiomers or diastereomers, their racemates or in form of a mixture of at least two of its stereoisomers, preferably enantiomers or diastereomers, in any mixing ratio, or physiologically acceptable salts thereof, or solvates, respectively.

Also particularly preferred are compounds of general formula (I), wherein $R^{12}$ represents H, a $C_{1-4}$-alkyl radical, a cyclohexyl radical or a phenyl radical, preferably H, CH$_3$, C$_2$H$_5$ or a phenyl radical, and the remaining residues $R^{13}$–$R^{18}$ and A have the meaning given above, optionally in form of one of their stereoisomers, preferably enantiomers or diastereomers, their racemates or in form of a mixture of at least two of its stereoisomers, preferably enantiomers or diastereomers, in any mixing ratio, or physiologically acceptable salts thereof, or solvates, respectively.

Also particularly preferred are compounds of general formula (I), wherein $R^{13}$ represents H, a $C_{1-4}$-alkyl radical, cyclohexyl or a phenyl radical, preferably H, CH$_3$, C$_2$H$_5$ or phenyl, and the remaining residues $R^{14}$–$R^{18}$ and A have the meaning given above, optionally in form of one of their stereoisomers, preferably enantiomers or diastereomers, their racemates or in form of a mixture of at least two of its stereoisomers, preferably enantiomers or diastereomers, in any mixing ratio, or physiologically acceptable salts thereof, or solvates, respectively.

Also particularly preferred are compounds of general formula (I), wherein $R^{14}$ represents H, a $C_{1-4}$-alkyl radical, cyclohexyl or a phenyl radical, preferably H, CH$_3$, C$_2$H$_5$ or phenyl, and the remaining residues $R^{15}$–$R^{18}$ and A have the meaning given above, optionally in form of one of their stereoisomers, preferably enantiomers or diastereomers, their racemates or in form of a mixture of at least two of its stereoisomers, preferably enantiomers or diastereomers, in any mixing ratio, or physiologically acceptable salts thereof, or solvates, respectively.

Also particularly preferred are compounds of general formula (I), wherein $R^{15}$ and $R^{16}$ are each independently selected from the group consisting of H, a $C_{1-4}$-alkyl radical, cyclohexyl and a phenyl radical, preferably from the group consisting of H, $CH_3$, $C_2H_5$ and phenyl, and the remaining residues $R^{17}$ and $R^{18}$ and A have the meaning given above, optionally in form of one of their stereoisomers, preferably enantiomers or diastereomers, their racemates or in form of a mixture of at least two of its stereoisomers, preferably enantiomers or diastereomers, in any mixing ratio, or physiologically acceptable salts thereof, or solvates, respectively.

Also particularly preferred are compounds of general formula (I), wherein $R^{17}$ represents H, a $C_{1-4}$-alkyl radical, cyclohexyl or a phenyl radical, preferably H, $CH_3$, $C_2H_5$ or phenyl, and the remaining residues $R^{18}$ and A have the meaning given above, optionally in form of one of their stereoisomers, preferably enantiomers or diastereomers, their racemates or in form of a mixture of at least two of its stereoisomers, preferably enantiomers or diastereomers, in any mixing ratio, or physiologically acceptable salts thereof, or solvates, respectively.

Also particularly preferred are compounds of general formula (I), wherein $R^{18}$ represents H, a $C_{1-4}$-alkyl radical or a phenyl radical, preferably H, $CH_3$ or phenyl, and the remaining residue A has the meaning given above, optionally in form of one of their stereoisomers, preferably enantiomers or diastereomers, their racemates or in form of a mixture of at least two of its stereoisomers, preferably enantiomers or diastereomers, in any mixing ratio, or physiologically acceptable salts thereof, or solvates, respectively.

More particularly preferred are compounds of general formula (I), wherein at least two of the residues $R^1$, $R^2$, $R^3$, $R^4$, preferably $R^2$ and $R^3$, do not represent hydrogen, and the residues from the group $R^1$, $R^2$, $R^3$ and $R^4$ that do not represent hydrogen as well as the remaining residues $R^5$–$R^{18}$ and A have the meaning given above, optionally in form of one of their stereoisomers, preferably enantiomers or diastereomers, their racemates or in form of a mixture of at least two of its stereoisomers, preferably enantiomers or diastereomers, in any mixing ratio, or physiologically acceptable salts thereof, or solvates, respectively.

More particularly preferred are compounds of general formula (I), wherein $R^5$ is $CH_3$ or $C_2H_5$, and the remaining residues $R^1$–$R^4$ and $R^6$–$R^{18}$ and A have the meaning given above, optionally in form of one of their stereoisomers, preferably enantiomers or diastereomers, their racemates or in form of a mixture of at least two of its stereoisomers, preferably enantiomers or diastereomers, in any mixing ratio, or physiologically acceptable salts thereof, or solvates, respectively.

Most preferred are the following benzoxazin-derived compounds of general formula (I):

[1] 2-[4-(2-oxo-4H-benzo[d][1,3]oxazin-1-yl)-piperidin-1-yl]-N-(9-oxo-9H-fluoren-2-yl)-acetamide,

[2] 2-[4-(2-oxo-4H-benzo[d][1,3]oxazin-1-yl)-piperidin-1-yl]-N-(9-oxo-9H-fluoren-3-yl)-acetamide),

[3] 2-[4-(2-oxo-4H-benzo[d][1,3]oxazin-1-yl)-piperidin-1-yl]-N-(9-oxo-9H-fluoren-3-yl)-acetamide hydrochloride,

[4] N-(4-benzoyl-phenyl)-2-[4-(2-oxo-4H-benzo[d][1,3]oxazin-1-yl)-piperidin-1-yl]-acetamide,

[5] N-(4-benzoyl-phenyl)-2-[4-(2-oxo-4H-benzo[d][1,3]oxazin-1-yl)-piperidin-1-yl]-acetamide hydrochloride,

[6] 2-[4-(2-oxo-4H-benzo[d][1,3]oxazin-1-yl)-piperidin-1-yl]-N-(5-oxo-5,6,7,8-tetrahidro-naphthalene-2-yl)-acetamide hydrochloride,

[7] 2-[4-(2-oxo-4H-benzo[d][1,3]oxazin-1-yl)-piperidin-1-yl]-N-(9-oxo-9H-fluoren-4-yl)-acetamide hydrochloride,

[8] N-(3-benzoyl-phenyl)-2-[4-(2-oxo-4H-benzo[d][1,3]oxazin-1-yl)-piperidin-1-yl]-acetamide hydrochloride,

[9] 2-[4-(2-oxo-4H-benzo[d][1,3]oxazin-1-yl)-piperidin-1-yl]-N-(1-oxo-indan-5-yl)-acetamide,

[10] 2-[4-(2-oxo-4H-benzo[d][1,3]oxazin-1-yl)-piperidin-1-yl]-N-(1-oxo-indan-5-yl)-acetamide hydrochloride,

[11] N-Indan-5-yl-2-[4-(2-oxo-4H-benzo[d][1,3]oxazin-1-yl)-piperidin-1-yl]-acetamide hydrochloride,

[12] N-(2-Methoxy-dibenzofuran-3-yl)-2-[4-(2-oxo-4H-benzo[d][1,3]oxazin-1-yl)-piperidin-1-yl]-acetamide hydrochloride),

[13] N-(4-Cyclohexyl-phenyl)-2-[4-(2-oxo-4H-benzo[d][1,3]oxazin-1-yl)-piperidin-1-yl]-acetamide hydrochloride,

[14] 1-{1-[2-(3,4-Dihidro-2H-quinolin-1-yl)-2-oxo-ethyl]piperidin-4-yl}-1,4-dihydro-benzo[d][1,3]oxazin-2-one hydrochloride,

[15] 2-[4-(2-oxo-4H-benzo[d][1,3]oxazin-1-yl)-piperidin-1-yl]-N-(9-oxo-9H-fluoren-3-yl)-2-phenyl-acetamide hydrochloride,

[16] 2-[4-(2-oxo-4H-benzo[d][1,3]oxazin-1-yl)-piperidin-1-yl]-N-(9-oxo-9H-fluoren-3-yl)-propionamide hydrochloride,

[17] N-(9-Ethyl-9H-carbazol-3-yl)-2-[4-(2-oxo-4H-benzo[d][1,3]oxazin-1-yl)-piperidin-1-yl]-acetamide,

[18] N-(9-Ethyl-9H-carbazol-3-yl)-2-[4-(2-oxo-4H-benzo[d][1,3]oxazin-1-yl)-piperidin-1-yl]-acetamide hydrochloride,

[19] 2-[4-(6-methyl-2-oxo-4H-benzo[d][1,3]oxazin-1-yl)-piperidin-1-yl]-N-(9-oxo-9H-fluoren-3-yl)-acetamide,

[20] 2-[4-(6-methyl-2-oxo-4H-benzo[d][1,3]oxazin-1-yl)-piperidin-1-yl]-N-(9-oxo-9H-fluoren-3-yl)-acetamide hydrochloride,

[21] N-(9-Ethyl-9H-carbazol-3-yl)-2-[4-(6-methyl-2-oxo-4H-benzo[d][1,3]oxazin-1-yl)-piperidin-1-yl]-acetamide hydrochloride,

[22] N-(4-Cyclohexyl-phenyl)-2-[4-(6-methyl-2-oxo-4H-benzo[d][1,3]oxazin-1-yl)-piperidin-1-yl]-acetamide,

[23] N-(4-Cyclohexyl-phenyl)-2-[4-(6-methyl-2-oxo-4H-benzo[d][1,3]oxazin-1-yl)-piperidin-1-yl]-acetamide hydrochloride,

[24] N-(4-benzoyl-phenyl)-2-[4-(6-methyl-2-oxo-4H-benzo[d][1,3]oxazin-1-yl)-piperidin-1-yl]-acetamide hydrochloride,

[25] N-(9-Methyl-9H-carbazol-3-yl)-2-[4-(2-oxo-4H-benzo[d][1,3]oxazin-1-yl)-piperidin-1-yl]-acetamide hydrochloride,

[26] N-(9,10-Dioxo-9,10-dihydro-anthracene-2-yl)-2-[4-(2-oxo-4H-benzo[d][1,3]oxazin-1-yl)-piperidin-1-yl]-acetamide hydrochloride,

[27] N-[4-(Ethyl-phenyl-amino)-phenyl]-2-[4-(2-oxo-4H-benzo[d][1,3]oxazin-1-yl)-piperidin-1-yl]-acetamide hydrochloride,

[28] 2-[4-(6-Methyl-2-oxo-4H-benzo[d][1,3]oxazin-1-yl)-piperidin-1-yl]-N-[4-methyl-phenyl-amino)-phenyl]-acetamide hydrochloride,

[29] 2-[4-(2-oxo-4H-benzo[d][1,3]oxazin-1-yl)-piperidin-1-yl]-N-[4-phenoxy-phenyl]-acetamide hydrochloride,

[30] N-[4-(Isopropyl-phenyl-amino)-phenyl]-2-[4-(2-oxo-4H-benzo[d][1,3]oxazin-1-yl)-piperidin-1-yl]-acetamide hydrochloride,

[31] 3-[4-(2-Oxo-4H-benzo[d][1,3]oxazin-1-yl)-piperidin-1-yl]-N-(9-oxo-9H-fluoren-3-yl)-propionamide hydrochloride,
[32] 2-[4-(6-Chloro-2-oxo-4H-benzo[d][1,3]oxazin-1-yl)-piperidin-1-yl]-N-(9-ethyl-9H-carbazol-3-yl)-acetamide hydrochloride,
[33] N-(4-Chloro-phenyl)-2-[4-(2-oxo-4H-benzo[d][1,3]oxazin-1-yl)-piperidin-1-yl]-acetamide hydrochloride,
[34] 2-[4-(6-Chloro-2-oxo-4H-benzo[d][1,3]oxazin-1-yl)-piperidin-1-yl]-N-(4-chloro-phenyl)-acetamide hydrochloride,
[35] 2-[4-(8-Methyl-2-oxo-4H-benzo[d][1,3]oxazin-1-yl)-piperidin-1-yl]-N-(9-oxo-9H-fluoren-3-yl)-acetamide hydrochloride,
[36] 2-[4-(6-Chloro-2-oxo-4H-benzo[d][1,3]oxazin-1-yl)-piperidin-1-yl]-N-(9-oxo-9H-fluoren-3-yl)-acetamide hydrochloride,
[37] N-(9-Hydroxy-9H-fluoren-3-yl)-2-[4-(8-methyl-2-oxo-4H-benzo[d][1,3]oxazin-1-yl)-piperidin-1-yl]-acetamide hydrochloride,
[38] N-(9-Hydroxy-9H-fluoren-2-yl)-2-[4-(2-oxo-4H-benzo[d][1,3]oxazin-1-yl)-piperidin-1-yl]-acetamide hydrochloride,
[39] 2-[4-(6-Chloro-2-oxo-4H-benzo[d][1,3]oxazin-1-yl)-piperidin-1-yl]-N-(9-hydroxy-9H-fluoren-3-yl)-acetamide hydrochloride,
[40] N-(9-Ethyl-9H-carbazol-3-yl)-2-[4-(8-methyl-2-oxo-4H-benzo[d][1,3]oxazin-1-yl)-piperidin-1-yl]-acetamide hydrochloride,
[41] 2-[4-(8-Methyl-2-oxo-4H-benzo[d][1,3]oxazin-1-yl)-piperidin-1-yl]-N-(4-trifluoromethyl-phenyl)-acetamide hydrochloride,
[42] 2-[4-(8-Methyl-2-oxo-4H-benzo[d][1,3]oxazin-1-yl)-piperidin-1-yl]-N-phenyl-acetamide hydrochloride,
[43] 2-[4-(2-oxo-4H-benzo[d][1,3]oxazin-1-yl)-piperidin-1-yl]-N-(4-trifluoromethylphenyl)-acetamide hydrochloride,
[44] 2-[4-(6-Chloro-2-oxo-4H-benzo[d][1,3]oxazin-1-yl)-piperidin-1-yl]-N-phenylacetamide hydrochloride,
[45] 2-[4-(6-Chloro-2-oxo-4H-benzo[d][1,3]oxazin-1-yl)-piperidin-1-yl]-N-(4-trifluoromethyl-phenyl)-acetamide hydrochloride,
[46] 2-[4-(2-oxo-4H-benzo[d][1,3]oxazin-1-yl)-piperidin-1-yl]-N-phenyl-acetamide hydrochloride,
[47] N-(4-Chloro-phenyl)-2-[4-(8-Methyl-2-oxo-4H-benzo[d][1,3]oxazin-1-yl)-piperidin-1-yl]-acetamide hydrochloride,
[48] N-(4-Cyano-phenyl)-2-[4-(2-oxo-4H-benzo[d][1,3]oxazin-1-yl)-piperidin-1-yl]-acetamide hydrochloride,
[49] N-(4-Cyano-phenyl)-2-[4-(8-methyl-2-oxo-4H-benzo[d][1,3]oxazin-1-yl)-piperidin-1-yl]-acetamide hydrochloride,
[50] 2-[4-(6-Chloro-2-oxo-4H-benzo[d][1,3]oxazin-1-yl)-piperidin-1-yl]-N-(4-cyano-phenyl)-acetamide hydrochloride,
[51] N-(4-Acethyl-phenyl)-2-[4-(2-oxo-4H-benzo[d][1,3]oxazin-1-yl)-piperidin-1-yl]-acetamide hydrochloride,
[52] 2-[4-(8-Methyl-2-oxo-4H-benzo[d][1,3]oxazin-1-yl)-piperidin-1-yl]-N-(4-phenoxy-phenyl)-acetamide hydrochloride,
[53] N-(4-Acethyl-phenyl)-2-[4-(6-chloro-2-oxo-4H-benzo[d][1,3]oxazin-1-yl)-piperidin-1-yl]-acetamide hydrochloride,
[54] N-(4-Acethyl-phenyl)-2-[4-(8-methyl-2-oxo-4H-benzo[d][1,3]oxazin-1-yl)-piperidin-1-yl]-acetamide hydrochloride,
[55] 2-[4-(6-Chloro-2-oxo-4H-benzo[d][1,3]oxazin-1-yl)-piperidin-1-yl]-N-(4-phenoxy-phenyl)-acetamide hydrochloride,
[56] N-(4-Benzoyl-phenyl)-2-[4-(8-methyl-2-oxo-4H-benzo[d][1,3]oxazin-1-yl)-piperidin-1-yl]-acetamide hydrochloride,
[57] N-(4-Benzoyl-phenyl)-2-[4-(6-chloro-2-oxo-4H-benzo[d][1,3]oxazin-1-yl)-piperidin-1-yl]-acetamide hydrochloride,
[58] N-(2-Chloro-phenyl)-2-[4-(6-methyl-2-oxo-4H-benzo[d][1,3]oxazin-1-yl)-piperidin-1-yl]-acetamide,
[59] 2-[4-(6-Methyl-2-oxo-4H-benzo[d][1,3]oxazin-1-yl)-piperidin-1-yl]-N-(2-trifluoromethyl-phenyl)-acetamide,
[60] 2-[4-(6-Methyl-2-oxo-4H-benzo[d][1,3]oxazin-1-yl)-piperidin-1-yl]-N-phenyl-acetamide,
[61] N-(4-Cyclohexyl-phenyl)-2-[4-(8-methyl-2-oxo-4H-benzo[d][1,3]oxazin-1-yl)-piperidin-1-yl]-acetamide hydrochloride,
[62] 2-[4-(6-Chloro-2-oxo-4H-benzo[d][1,3]oxazin-1-yl)-piperidin-1-yl]-N-(4-cyclohexyl-phenyl)-acetamide hydrochloride,
[63] N-(2-Benzoyl-phenyl)-2-[4-(2-oxo-4H-benzo[d][1,3]oxazin-1-yl)-piperidin-1-yl]-acetamide hydrochloride,
[64] N-(2-Benzoyl-phenyl)-2-[4-(8-methyl-2-oxo-4H-benzo[d][1,3]oxazin-1-yl)-piperidin-1-yl]-acetamide hydrochloride, g
[65] N-(2-Benzoyl-phenyl)-2-[4-(6-chloro-2-oxo-4H-benzo[d][1,3]oxazin-1-yl)-piperidin-1-yl]-acetamide hydrochloride,
[66] N-(2-Benzoyl-phenyl)-2-[4-(6-methyl-2-oxo-4H-benzo[d][1,3]oxazin-1-yl)-piperidin-1-yl]-acetamide,
[67] 2-[4-(6-Methyl-2-oxo-4H-benzo[d][1,3]oxazin-1-yl)-piperidin-1-yl]-N-(4-phenoxy-phenyl)-acetamide hydrochloride,
[68] N-(4-Acetyl-phenyl)-2-[4-(6-methyl-2-oxo-4H-benzo[d][1,3]oxazin-1-yl)-piperidin-1-yl]-acetamide hydrochloride,
[69] N-(9-Hydroxy-9H-fluoren-3-yl)-2-[4-(2-oxo-4H-benzo[d][1,3]oxazin-1-yl)-piperidin-1-yl]-acetamide hydrochloride,
[70] 2-[4-(6-Chloro-2-oxo-4H-benzo[d][1,3]oxazin-1-yl)-piperidin-1-yl]-N-(9-oxo-9H-fluoren-2-yl)-acetamide hydrochloride,
[71] 2-[4-(6-Methyl-2-oxo-4H-benzo[d][1,3]oxazin-1-yl)-piperidin-1-yl]-N-(9-oxo-9H-fluoren-2-yl)-acetamide hydrochloride,
[72] 2-[4-(8-Methyl-2-oxo-4H-benzo[d][1,3]oxazin-1-yl)-piperidin-1-yl]-N-(9-oxo-9H-fluoren-2-yl)-acetamide hydrochloride,
[73] 2-[4-(6-Chloro-2-oxo-4H-benzo[d][1,3]oxazin-1-yl)-piperidin-1-yl]-N-(9-hydroxy-9H-fluoren-2-yl)-acetamide hydrochloride,
[74] N-(9-Hydroxy-9H-fluoren-2-yl)-2-[4-(6-methyl-2-oxo-4H-benzo[d][1,3]oxazin-1-yl)-piperidin-1-yl]-acetamide hydrochloride,
[75] N-(9-Hydroxy-9H-fluoren-2-yl)-2-[4-(8-methyl-2-oxo-4H-benzo[d][1,3]oxazin-1-yl)-piperidin-1-yl]-acetamide hydrochloride,
[76] N-(9-Hydroxy-9H-fluoren-3-yl)-2-[4-(6-methyl-2-oxo-4H-benzo[d][1,3]oxazin-1-yl)-piperidin-1-yl]-acetamide hydrochloride,
[77] N-(4-Cyclohexyl-phenyl)-2-[4-(7-fluoro-2-oxo-4H-benzo[d][1,3]oxazin-1-yl)-piperidin-1-yl]-acetamide hydrochloride,
[78]N-(9-Ethyl-9H-carbazol-3-yl)-2-[4-(5-fluoro-2-oxo-4H-benzo[d][1,3]oxazin-1-yl)-piperidin-1-yl]-acetamide hydrochloride,

[79] N-(9-Ethyl-9H-carbazol-3-yl)-2-[4-(6-metoxy-2-oxo-4H-benzo[d][1,3]oxazin-1-yl)-piperidin-1-yl]-acetamide hydrochloride,
[80] N-(9-Ethyl-9H-carbazol-3-yl)-2-[4-(7-methyl-2-oxo-4H-benzo[d][1,3]oxazin-1-yl)-piperidin-1-yl]-acetamide hydrochloride,
[81] 2-[4-(5-Chloro-2-oxo-4H-benzo[d][1,3]oxazin-1-yl)-piperidin-1-yl]-N-(9-ethyl-9H-carbazol-3-yl)acetamide hydrochloride,
[82] 2-[4-(5-Fluoro-2-oxo-4H-benzo[d][1,3]oxazin-1-yl)-piperidin-1-yl]-N-(4-phenoxy-phenyl)-acetamide hydrochloride,
[83] 2-[4-(6-metoxy-2-oxo-4H-benzo[d][1,3]oxazin-1-yl)-piperidin-1-yl]-N-(9-oxo-9H-fluoren-3-yl)-acetamide,
[84] N-Dibenzofuran-2-yl-2-[4-(8-metoxy-2-oxo-4H-benzo[d][1,3]oxazin-1-yl)-piperidin-1-yl]-acetamide,
[85] 2-[4-(7-Chloro-2-oxo-4H-benzo[d][1,3]oxazin-1-yl)-piperidin-1-yl]-N-dibenzofuran-2-yl-acetamide,
[86] 2-[4-(6-Fluoro-2-oxo-4H-benzo[d][1,3]oxazin-1-yl)-piperidin-1-yl]-N-(9-oxo-9H-fluoren-3-yl)-acetamide,
[87] 2-[4-(7-Fluoro-2-oxo-4H-benzo[d][1,3]oxazin-1-yl)-piperidin-1-yl]-N-(9-hydroxy-9H-fluoren-3-yl)-acetamide,
[88] N-(9H-Carbazol-3-yl)-2-[4-(5-methyl-2-oxo-4H-benzo[d][1,3]oxazin-1-yl)-piperidin-1-yl]-acetamide,
[89] N-(9H-Carbazol-3-yl)-2-[4-(5-fluoro-2-oxo-4H-benzo[d][1,3]oxazin-1-yl)-piperidin-1-yl]-acetamide,
[90] N-(9H-carbazol-3-yl)-2-[4-(6-metoxy-2-oxo-4H-benzo[d][1,3]oxazin-1-yl)-piperidin-1-yl]-acetamide,
[91] N-(9-Ethyl-9H-carbazol-3-yl)-2-[4-(5-metoxy-2-oxo-4H-benzo[d][1,3]oxazin-1-yl)-piperidin-1-yl]-acetamide,
[92] 2-[4-(5-Metoxy-2-oxo-4H-benzo[d][1,3]oxazin-1-yl)-piperidin-1-yl]-N-(4-phenoxy-phenyl)-acetamide,
[93] N-(9-Hydroxy-9H-fluoren-3-yl)-2-[4-(7-methyl-2-oxo-4H-benzo[d][1,3]oxazin-1-yl)-piperidin-1-yl]-acetamide,
[94] N-(9-Hydroxy-9H-fluoren-3-yl)-2-[4-(8-metoxy-2-oxo-4H-benzo[d][1,3]oxazin-1-yl)-piperidin-1-yl]-acetamide,
[95] N-Dibenzofuran-2-yl-2-[4-(5-methyl-2-oxo-4H-benzo[d][1,3]oxazin-1-yl)-piperidin-1-yl]-acetamide,
[96] N-[4-(Ethyl-phenyl-amino)-phenyl]-2-[4-(7-methyl-2-oxo-4H-benzo[d][1,3]oxazin-1-yl)-piperidin-1-yl]-acetamide,
[97] N-(9H-Carbazol-3-yl)-2-[4-(8-chloro-2-oxo-4H-benzo[d][1,3]oxazin-1-yl)-piperidin-1-yl]-acetamide,
[98] N-[4-(Ethyl-phenyl-amino)-phenyl]-2-[4-(8-metoxi-2-oxo-4H-benzo[d][1,3]oxazin-1-yl)-piperidin-1-yl]-acetamide,
[99] N-(9-Hydroxy-9H-fluoren-4-yl)-2-[4-(2-oxo-4H-benzo[d][1,3]oxazin-1-yl)-piperidin-1-yl]-acetamide,
[100] N-[4-(Hydroxy-phenyl-methyl)-phenyl-2-[4-(2-oxo-4H-benzo[d][1,3]oxazin-1-yl)-piperidin-1-yl]-acetamide,
[101] N-[4-Chloro-2-(2-chloro-benzoyl)-phenyl]-2-[4-(6-methyl-2-oxo-4H-benzo[d][1,3]oxazin-1-yl)-piperidin-1-yl]-acetamide,
[102] N-[4-Chloro-2-(2-chloro-benzoyl)-phenyl]-2-[4-(2-oxo-4H-benzo[d][1,3]oxazin-1-yl)-piperidin-1-yl]-acetamide hydrochloride,
[103] N-[4-Chloro-2-(2-chloro-benzoyl)-phenyl]-2-[4-(8-methyl-2-oxo-4H-benzo[d][1,3]oxazin-1-yl)-piperidin-1-yl]-acetamide hydrochloride,
[104] N-[4-Chloro-2-(2-chloro-benzoyl)-phenyl]-2-[4-(6-chloro-2-oxo-4H-benzo[d][1,3]oxazin-1-yl)-piperidin-1-yl]-acetamide hydrochloride,
[105] 2-[4-(7-Methyl-2-oxo-4H-benzo[d][1,3]oxazin-1-yl)-piperidin-1-yl]-N-thiazole-2-yl-acetamide,
[106] 2-[4-(6-Fluoro-2-oxo-4H-benzo[d][1,3]oxazin-1-yl)-piperidin-1-yl]-N-thiazole-2-yl-acetamide,
[107] N-Dibenzothiophene-2-yl-2-[4-(5-methoxy-2-oxo-4H-benzo[d][1,3]oxazin-1-yl)-piperidin-1-yl]-acetamide,
[108] 2-[4-(7-Chloro-2-oxo-4H-benzo[d][1,3]oxazin-1-yl)-piperidin-1-yl]-N-dibenzothiophene-2-yl-acetamide,
[109] 2-[4-(5-Hydroxy-2-oxo-4H-benzo[d][1,3]oxazin-1-yl)-piperidin-1-yl]-N-(4-phenoxy-phenyl)-acetamide,
[110] 1-{1-[2-(3,4-Dihydro-1H-isoquinoline-2-yl)-2-oxo-ethyl]-piperidin-4-yl}-1,4-dihydro-benzo[d][1,3]oxazin-2-one hydrochloride,
[111] 2-[4-(6-Fluoro-2-oxo-4H-benzo[d][1,3]oxazin-1-yl)-piperidin-1-yl]-N-quinoline-6-yl-acetamide,
[112] 2-[4-(6-Methoxy-2-oxo-4H-benzo[d][1,3]oxazin-1-yl)-piperidin-1-yl]-N-quinoline-6-yl-acetamide,
[113] 2-[4-(6-Chloro-2-oxo-4H-benzo[d][1,3]oxazin-1-yl)-piperidin-1-yl]-N-quinoline-6-yl-acetamide,
[114] 2-[4-(6-Fluoro-2-oxo-4H-benzo[d][1,3]oxazin-1-yl)-piperidin-1-yl]-N-(2-methyl-benzothiazole-5-yl)-acetamide,
[115] 2-[4-(6-Chloro-2-oxo-4H-benzo[d][1,3]oxazin-1-yl)-piperidin-1-yl]-N-(2-methyl-benzothiazole-5-yl)-acetamide,
[116] 2-[4-(6-Methoxy-2-oxo-4H-benzo[d][1,3]oxazin-1-yl)-piperidin-1-yl]-N-(2-methyl-benzothiazole-5-yl)-acetamide,
[117] N-(3-Dimethylamino-phenyl)-2-[4-(2-oxo-4H-benzo[d][1,3]oxazin-1-yl)-piperidin-1-yl]-acetamide,
[118] N-(4-Dimethylamino-phenyl)-2-[4-(2-oxo-4H-benzo[d][1,3]oxazin-1-yl)-piperidin-1-yl]-acetamide,
[119] N-(3-Dimethylamino-phenyl)-2-[4-(8-methyl-2-oxo-4H-benzo[d][1,3]oxazin-1-yl)-piperidin-1-yl]-acetamide,
[120] N-(4-Dimethylamino-phenyl)-2-[4-(8-methyl-2-oxo-4H-benzo[d][1,3]oxazin-1-yl)-piperidin-1-yl]-acetamide,
[121] N-(3-Dimethylamino-phenyl)-2-[4-(6-methyl-2-oxo-4H-benzo[d][1,3]oxazin-1-yl)-piperidin-1-yl]-acetamide,
[122] N-(4-Dimethylamino-phenyl)-2-[4-(6-methyl-2-oxo-4H-benzo[d][1,3]oxazin-1-yl)-piperidin-1-yl]-acetamide,
[123] N-(4-Diethylamino-phenyl)-2-[4-(2-oxo-4H-benzo[d][1,3]oxazin-1-yl)-piperidin-1-yl]-acetamide,
[124] 2-{2-[4-(2-Oxo-4H-benzo[d][1,3]oxazin-1-yl)-piperidin-1-yl]-acethylamino}-benzoic acid methyl ester,
[125] 2-{2-[4-(8-Methyl-2-oxo-4H-benzo[d][1,3]oxazin-1-yl)-piperidin-1-yl]-acethylamino}-benzoic acid methyl ester,
[126] N-(2-Methoxy-dibenzofuran-3-yl)-2-[4-(2-oxo-4H-benzo[d][1,3]oxazin-1-yl)-piperidin-1-yl]-acetamide hydrochloride,
[127] N-2-[4-(6-Chloro-2-oxo-4H-benzo[d][1,3]oxazin-1-yl)-piperidin-1-yl]-N-(2-methoxy-dibenzofuran-3-yl)-acetamide hydrochloride,
[128] 2-{2-[4-(6-Chloro-2-oxo-4H-benzo[d][1,3]oxazin-1-yl)-piperidin-1-yl]-acethylamino}-benzoic acid methyl ester,
[129] 2-{2-[4-(6-Methyl-2-oxo-4H-benzo[d][1,3]oxazin-1-yl)-piperidin-1-yl]-acethylamino}-benzoic acid methyl ester,
[130] 2-[4-(6-Chloro-2-oxo-4H-benzo[d][1,3]oxazin-1-yl)-piperidin-1-yl]-N-(4-diethylamino-phenyl)-acetamide dihydrochloride,
[131] 2-[4-(6-Chloro-2-oxo-4H-benzo[d][1,3]oxazin-1-yl)-piperidin-1-yl]-N-{4-[ethyl-(2-hydroxy-ethyl)-amino]-phenyl}acetamide dihydrochloride,
[132] N-{4-[Ethyl-(2-hydroxy-ethyl)-amino]-phenyl}-2-[4-(6-methyl-2-oxo-4H-benzo[d][1,3]oxazin-1-yl)-piperidin-1-yl]-acetamide dihydrochloride,

[133] N-(4-Diethylamino-phenyl)-2-[4-(6-methyl-2-oxo-4H-benzo[d][1,3]oxazin-1-yl)-piperidin-1-yl]-acetamide dihydrochloride,

[134] N-(4-Diethylamino-phenyl)-2-[4-(8-methyl-2-oxo-4H-benzo[d][1,3]oxazin-1-yl)-piperidin-1-yl]-acetamide dihydrochloride,

[135] N-{4-[ethyl-(2-hydroxy-ethyl)-amino]-phenyl}-2-[4-(8-methyl-2-oxo-4H-benzo[d][1,3]oxazin-1-yl)-piperidin-1-yl]-acetamide dihydrochloride,

[136] N-Benzo[1,3]dioxol-5-yl-2-[4-(2-oxo-4H-benzo[d][1,3]oxazin-1-yl)-piperidin-1-yl]-acetamide,

[137] N-Benzo[1,3]dioxol-5-yl-2-[4-(6-methyl-2-oxo-4H-benzo[d][1,3]oxazin-1-yl)-piperidin-1-yl]-acetamide,

[138] N-Benzo[1,3]dioxol-5-yl-2-[4-(6-chloro-2-oxo-4H-benzo[d][1,3]oxazin-1-yl)-piperidin-1-yl]-acetamide,

[139] N-Benzo[1,3]dioxol-5-yl-2-[4-(8-methyl-2-oxo-4H-benzo[d][1,3]oxazin-1-yl)-piperidin-1-yl]-acetamide,

[140] N-{4-[ethyl-(2-hydroxy-ethyl)-amino]-phenyl}-2-[4-(2-oxo-4H-benzo[d][1,3]oxazin-1-yl)-piperidin-1-yl]-acetamide dihydrochloride,

[141] 2-[4-(6-Chloro-2-oxo-4H-benzo[d][1,3]oxazin-1-yl)-piperidin-1-yl]-N-(4-dimethylamino-phenyl)-acetamide dihydrochloride,

[142] N-(9-Hydroxy-9H-fluoren-3-yl)-2-[4-(4-methyl-2-oxo-4H-benzo[d][1,3]oxazin-1-yl)-piperidin-1-yl]-acetamide,

[143] N-(9-Ethyl-9H-carbazol-3-yl)-2-[4-(4-methyl-2-oxo-4H-benzo[d][1,3]oxazin-1-yl)-piperidin-1-yl]-acetamide,

[144] 2-[4-(4-Methyl-2-oxo-4H-benzo[d][1,3]oxazin-1-yl)-piperidin-1-yl]-N-(4-phenoxy-phenyl)-acetamide,

[145] 2-{2-[4-(2-Oxo-4H-benzo[d][1,3]oxazin-1-yl)-piperidin-1-yl]-acetamino}-benzoic acid,

[146] 1-{1-[2-(6-Fluoro-2-methyl-3,4-dihydro-2H-quinoline-1-yl)-2-oxo-ethyl]-piperidin-4-yl}-1,4-dihydro-benzo[d][1,3]oxazin-2-one,

[147] 6-Chloro-1-{1-[2-(6-fluoro-2-methyl-3,4-dihydro-2H-quinoline-1-yl)-2-oxo-ethyl]-piperidin-4-yl}-1,4-dihydro-benzo[d][1,3]oxazin-2-one,

[148] 1-{1-[2-(6-Fluoro-2-methyl-3,4-dihydro-2H-quinoline-1-yl)-2-oxo-ethyl]-piperidin-4-yl}-6-methyl-1,4-dihydro-benzo[d][1,3]oxazin-2-one,

[149] 1-{1-[2-(6-Fluoro-2-methyl-3,4-dihydro-2H-quinoline-1-yl)-2-oxo-ethyl]-piperidin-4-yl}-8-methyl-1,4-dihydro-benzo[d][1,3]oxazin-2-one,

[150] 1-{1-[2-(6-Methoxy-2,2,4-trimethyl-3,4-dihydro-2H-quinoline-1-yl)-2-oxo-ethyl]-piperidin-4-yl}-1,4-dihydro-benzo[d][1,3]oxazin-2-one;

[151] 6-Chloro-1-{1-[2-(6-methoxy-2,2,4-trimethyl-3,4-dihydro-2H-quinoline-1-yl)-2-oxo-ethyl]-piperidin-4-yl}-1,4-dihydro-benzo[d][1,3]oxazin-2-one,

[152] 1-{1-[2-(6-Methoxy-2,2,4-trimethyl-3,4-dihydro-2H-quinoline-1-yl)-2-oxo-ethyl]-piperidin-4-yl}-8-methyl-1,4-dihydro-benzo[d][1,3]oxazin-2-one,

[153] 1-{1-[2-(6-Methoxy-2,2,4-trimethyl-3,4-dihydro-2H-quinoline-1-yl)-2-oxo-ethyl]-piperidin-4-yl}-6-methyl-1,4-dihydro-benzo[d][1,3]oxazin-2-one,

[154] N-(9-Hydroxy-9H-fluoren-3-yl)-2-[4-(2-oxo-7-trifluormethyl-4H-benzo[d][1,3]oxazin-1-yl)-piperidin-1-yl]-acetamide,

[155] N-(9H-carbazol-3-yl)-2-[4-(2-oxo-7-trifluormethyl-4H-benzo[d][1,3]oxazin-1-yl)-piperidin-1-yl]-acetamide,

[156] 2-[4-(2-Oxo-7-trifluormethyl-4H-benzo[d][1,3]oxazin-1-yl)-piperidin-1-yl]-N-(4-phenoxy-phenyl)-acetamide,

[157] N-(9-Ethyl-9H-carbazol-3-yl)-2-[4-(2-oxo-7-trifluormethyl-4H-benzo[d][1,3]oxazin-1-yl)-piperidin-1-yl]-acetamide,

[158] 2-4-(6,7-Difluoro-2-oxo-4H-benzo[d][1,3]oxazin-1-yl)-piperidin-1-yl]-N-(9-hydroxy-9H-fluoren-3-yl)-acetamide,

[159] N-(9H-carbazol-3-yl)-2-[4-(6,7-difluoro-2-oxo-4H-benzo[d][1,3]oxazin-1-yl)-piperidin-1-yl]-acetamide,

[160] 2-4-(6,7-Difluoro-2-oxo-4H-benzo[d][1,3]oxazin-1-yl)-piperidin-1-yl]-N-(4-phenoxy-phenyl)-acetamide,

[161] 2-4-(6,7-Difluoro-2-oxo-4H-benzo[d][1,3]oxazin-1-yl)-piperidin-1-yl]-N-(9-ethyl-9H-carbazol-3-yl)-acetamide,

[162] 2-[4-(4-Methyl-2-oxo-4H-benzo[d][1,3]oxazin-1-yl)-piperidin-1-yl]-N-(9-oxo-9H-fluoren-3-yl)-acetamide,

[163] 2-[4-(6-Chloro-2-oxo-4H-benzo[d][1,3]oxazin-1-yl)-piperidin-1-yl]-N-(3-dimethylamino-phenyl)-acetamide.

In a further aspect the present invention also provides a process for the preparation of benzoxazinone-derived compounds of general formula (I), wherein $R^1$–$R^{11}$ and A have the meaning given above, according to which at least one compound of general formula (II),

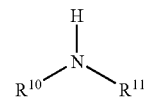

(II)

wherein $R^{10}$ and $R^{11}$ have the meaning given above, is reacted with at least one compound of general formula (III),

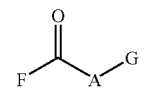

(III)

wherein A has the meaning given above, F represents halogen, hydroxy or an O-acyl group and G represents halogen, preferably chlorine, in a suitable reaction medium and in the presence of at least one base and/or at least one auxiliary agent, and reacting the so obtained compound of general (IV)

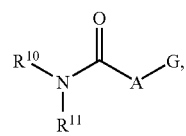

(IV)

wherein A, G, $R^{10}$ and $R^{11}$ have the above defined meaning, with at least one piperidin compound of general formula (V) and/or a salt, preferably hydrochloride, thereof,

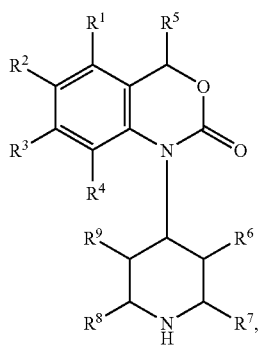

(V)

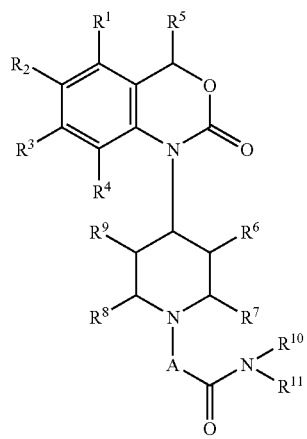

(I)

wherein $R^1$ to $R^9$ have the meaning as definded above, in a suitable reaction medium, optionally in the presence of at least one base and/or at least one auxiliary agent.

According to the invention, the process may be illustrated as an example by the following reaction scheme 1:

Scheme 1:

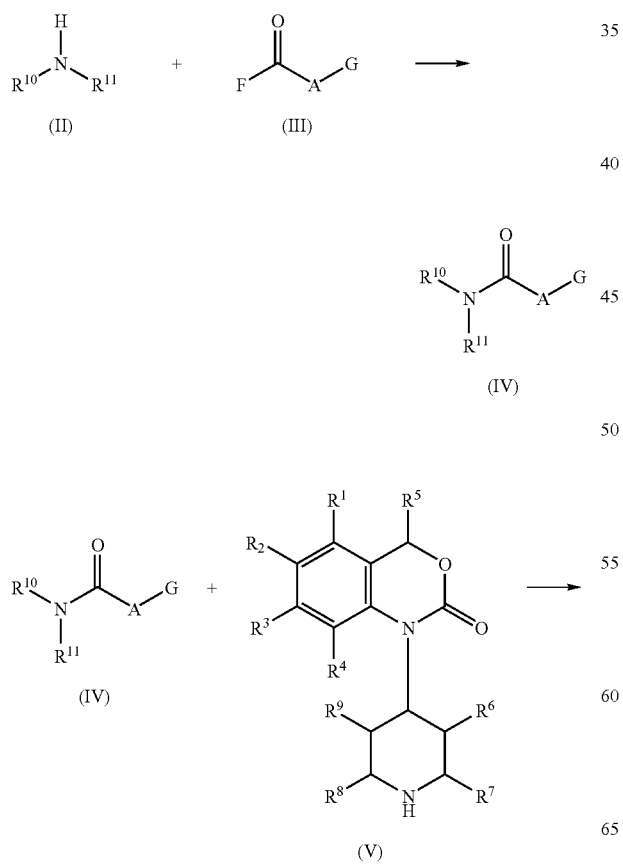

wherein $R^1$ to $R^{11}$ and A have the meaning as given above.

Suitable reaction media are e.g. organic solvents, such as ethers, preferably diethyl ether, dioxane, tetrahydrofurane, dimethyl glycol ether, or alcohols, e.g. methanol, ethanol, propanol, isopropanol, butanol, isobutanol, tert-butanol, or hydrocarbons, preferably benzene, toluene, xylene, hexane, cyclohexane, petroleum ether, or halogenated hydrocarbons, e.g. dichloromethane, trichloromethane, tetrachloromethane, dichloroethylene, trichloroethylene, chlorobenzene or/and other solvents, preferably ethyl acetate, triethylamine, pyridine, dimethylsulfoxide, diemthylformamide, hexamethylphosphoramide, acetonitril, acetone or nitromethane, are included. Mixtures based one or more of the afore mentioned solvents may also be used.

Bases that may be used in the processes according to the present invention are generally organic or inorganic bases, preferably alkali metal hydroxides, e.g. sodium hydroxyde or potassium hydroxyde, or obtained from other metals such as barium hydroxyde or different carbonates, preferably potassium carbonate, sodium carbonate, calcium carbonate, or alkoxides, e.g. sodium methoxide, potassium methoxide, sodium ethoxide, potassium methoxide, potassium ethoxide or potassium tert-butoxide, or organic amines, preferably triethylamine, diisopropyethylamine or heterocycles, e.g. 1,4-diazabicyclo[2.2.2]octane, 1,8-diazabicyclo[5.4.0]undec-7-ene pyridine, diamino pyridine, dimethylaminopyridine, methylpiperidine or morpholine. Alkali metals such as sodium or ist hydrides, e.g. sodium hydride, may also be used. Mixtures based one or more of the afore mentioned bases may also be used.

The above mentioned bases may be used for the process as auxiliary agents, hen appropriate. Other suitable auxiliary agents for the above mentioned reactions are, for example, dehydrating agents like carbodiimides, e.g. diisopropylcarbodiimide, cyclohexylcarbodiimide or N-(3-dimethylaminopropyl)-N'-ethylcarbodiimide hydrochloride, or carbonylic compounds, e.g. carbonyldiimidazol or compounds like isobutylchloroformiate or methansulfonyl chloride, among others. These reagents are generally used in amounts from 0.5 to 5 mol versus 1 mol of the corresponding reactands. These bases are generally used in amounts from 0.05 to 10 mol versus 1 mol of the corresponding reactands.

During some of the synthetic reactions described or while preparing the compounds of general formulas (I), (II), (III), (IV) and (V), the protection of sensitive groups or of reagents may be necessary and/or desirable. This can be performed by using conventional protective groups like those described in the literature [Protective groups in Organic Chemistry, ed. J. F. W. McOmie, Plenum Press, 1973; T. W. Greene & P. G. M. Wuts, Protective Groups in Organic Chemistry, John Wiley & sons, 1991. Said literature description is hereby incorporated by reference as part of the disclosure. The protective groups may also be eliminated as convenient by means well-known to those skilled in the art.

The compounds of general formulas (II), (III), (IV) and (V) are either commercially available or can be produced according to methods known to those skilled in the art. The reaction of compounds of general formulas (IV) and (V) to yield benzoxazinone-derived compounds of general formula (I) may also be facilitated by conventional methods known to those skilled in the art.

The substituted benzoxazinone compounds of general formula (V), wherein $R^5$ represents H, are preferably synthesized from substituted anthranilic acid or a corresponding ester via the corresponding substituted benzylalcohol (see scheme 2, method A). By reductive amination with 1-Boc-(tert.-Butylcarbonyloxy) the Boc-piperidin-moiety is introduced into the substituted benzylalcohol. The benzoxazinone-ring is formed by cyclisation with triphosgene. The elimination of the Boc-protecting group is carried out by treatment in acidic media according to the method described in Williams et al., J. Med. Chem. 1995 38, 4634 and later by Bell et al., J. Med. Chem., 1998, 41, 2146 which are hereby incorporated by reference and form part of the disclosure. By reacting such a substituted benzoxazinone compound of general formula (V) with a halogenated amide of general formula (IV) benzoxazinone derived compounds of general formula (I) are obtained.

By reduction of the corresponding ketones via conventional methods known to those skilled in the art, e.g. by reduction with sodium borohydride (see scheme 2, method B, R5=Z) benzoxazinone derived compounds of general formula (I), wherein $R^5$ represents an unbranched or branched, saturated or unsaturated, optionally at least mono-substituted aliphatic radical or a saturated or unsaturated, optionally at least mono-substituted, optionally at least one heteroatom as ring member containing cycloaliphatic radical (denoted by Z in method B) can be obtained.

Scheme 2:

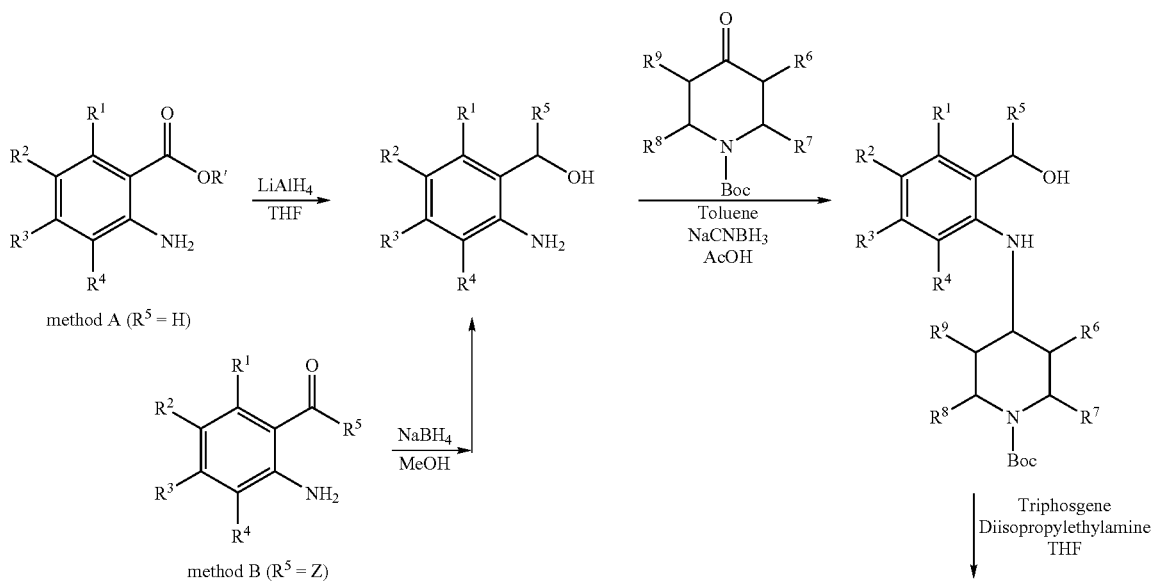

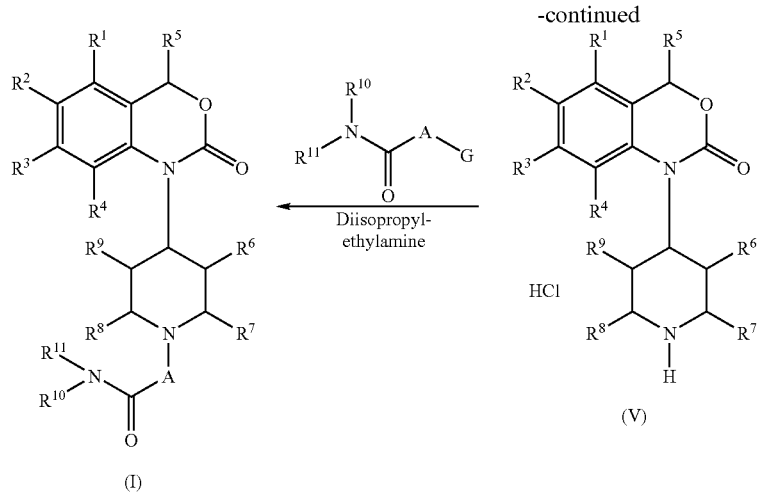
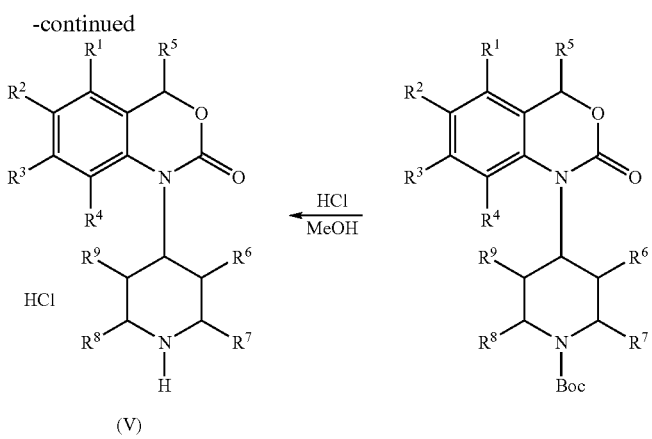

The compounds of general formula (IV) are commercially available or may be produced according to scheme I by conventional methods known to those skilled in the art. Essentially the respective compound of general formula (II) is reacted with chloroacetyl chloride or the respective compound of general formula (III) in the presence of an organic reaction medium, preferably dichloromethane and a base, preferably triethylamine and/or diisopropylethylamine.

The present invention also provides for novel intermediates, namely the following compounds of general formula (V):

[1] 6-Methyl-1-(piperidin-4-yl)-1,4-dihydro-2H-3,1-benzoxazin-2-one,
[2] 7-Methyl-1-(piperidin-4-yl)-1,4-dihydro-2H-3,1-benzoxazin-2-one,
[3] 8-Methyl-1-(piperidin-4-yl)-1,4-dihydro-2H-3,1-benzoxazin-2-one,
[4] 5-Chloro-1-(piperidin-4-yl)-1,4-dihydro-2H-3,1-benzoxazin-2-one,
[5] 6-Chloro-1-(piperidin-4-yl)-1,4-dihydro-2H-3,1-benzoxazin-2-one,
[6] 8-Chloro-1-(piperidin-4-yl)-1,4-dihydro-2H-3,1-benzoxazin-2-one,
[7] 6-Fluoro-1-(piperidin-4-yl)-1,4-dihydro-2H-3,1-benzoxazin-2-one,
[8] 7-Fluoro-1-(piperidin-4-yl)-1,4-dihydro-2H-3,1-benzoxazin-2-one,
[9] 5-Methoxy-1-(piperidin-4-yl)-1,4-dihydro-2H-3,1-benzoxazin-2-one,
[10] 6-Methoxy-1-(piperidin-4-yl)-1,4-dihydro-2H-3,1-benzoxazin-2-one,
[11] 5-Hydroxy-1-(piperidin-4-yl)-1,4-dihydro-2H-3,1-benzoxazin-2-one,
[12] 6-Hydroxy-1-(piperidin-4-yl)-1,4-dihydro-2H-3,1-benzoxazin-2-one,
[13] 8-Hydroxy-1-(piperidin-4-yl)-1,4-dihydro-2H-3,1-benzoxazin-2-one,
[14] 6,7-Difluoro-1-piperidin-4-yl-1,4-dihydro-benzo[d][1,3]oxazin-2-one and
[15] 1-Piperidin-4-yl-7-trifluoromethyl-1,4-dihydro-benzo[d][1,3]oxazin-2-one, optionally in form of their salts.

In a further aspect the present invention also provides a process for the preparation of salts of benzoxazinone-derived compounds of general formula (I), wherein at least one compound of general formula (I) having at least one basic group is reacted with an inorganic or organic acid, preferably in the presence of a suitable reaction medium. Suitable reaction media are the ones given above. Suitable inorganic acids are for example hydrochloric acid, hydrobromic acid, phosphoric acid, sulfuric acid, nitric acid, suitable organic acids are e.g. citric acid, maleic acid, fumaric acid, tartaric acid, or derivatives thereof, such as p-toluenesulfonic acid, methanesulfonic acid or camphersulfonic acid.

In yet a further aspect the present invention also provides a process for the preparation of salts of benzoxazinone-derived compounds of general formula (I), wherein at least one compound of general formula (I) having at least one acidic group is reacted with one or more suitable bases, preferably in the presence of a suitable reaction medium. Suitable bases are e.g. hydroxides, carbonates or alkoxides, which include suitable cations, derived e.g. from alkaline metals, alkaline earth metals or organic cations, e.g. $[NH_nR_{4-n}]^+$, wherein n is 0, 1, 2, 3 or 4 and R represents a branched or unbranched $C_{1-4}$-alkyl-radical.

Solvates, preferably hydrates, of the Benzoxazinone-derived compounds of general formula (I) may also be obtained by standard procedures known to those skilled in the art.

If the Benzoxazinone-derived compounds of general formula (I) are obtained in form of a mixture of stereoisomers, particularly enantiomers or diastereomers, said mixtures may be separated by standard procedures known to those skilled in the art, e.g. chromatographic methods or crystallization with chiral reagents.

The purification and isolation of the Benzoxazinone-derived compounds of general formula (I) or a corresponding stereoisomer, or salt, or solvate respectively, if required, may be carried out by conventional methods known to those skilled in the art, e.g. chromatographic methods or recrystallization.

The Benzoxazinone-derived compounds of general formula (I), their stereoisomers or the respective salts or solvates are toxicologically acceptable and are therefore suitable as pharmaceutical active substances for the preparation of medicaments.

The present invention therefore also provides for a medicament comprising at least one benzoxazinone-derived compound of general formula (I), optionally in form of one of its stereoisomers, preferably enantiomers or diastereomers, its racemate or in form of a mixture of at least two of its stereoisomers, preferably enantiomers or diastereomers, in any mixing ratio, or a physiologically acceptable salt thereof, or a solvate, respectively, and optionally one or more pharmaceutically acceptable adjuvants.

Furthermore, the present invention also provides for a pharmaceutical composition comprising at least one benzoxazinone-derived compound of general formula (I), optionally in form of one of its stereoisomers, preferably enantiomers or diastereomers, its racemate or in form of a mixture of at least two of its stereoisomers in any mixing ratio, or a physiologically acceptable salt thereof, or a solvate, respectively, and optionally one or more pharmaceutically acceptable adjuvants, which is not yet formulated into a medicament.

Preferably the medicament is suitable for the regulation of neuropeptide Y receptors, preferably of neuropeptide Y 5 (NPY5) receptor, for the regulation of food ingestion, preferably for the prophylaxis and/or treatment of disorders of food ingestion, preferably obesity, anorexia or bulimia, for the prophylaxis and/or treatment of disorders of the peripheral nervous system, disorders of the central nervous system, diabetes, arthritis, epilepsy, anxiety, depression, cognitive disorders, preferably memory disorders, cardiovascular diseases, pain, hypertensive syndrom, inflammatory diseases or immune diseases.

The present invention also provides for the use of at least one benzoxazinone-derived compound of general formula (I), optionally in form of one of its stereoisomers, preferably enantiomers or diastereomers, its racemate or in form of a mixture of at least two of its stereoisomers, preferably enantiomers or diastereomers, in any mixing ratio, or a physiologically acceptable salt thereof, or a solvate, respectively, for the manufacture of a medicament for the regulation of neuropeptide Y receptors, preferably of neuropeptide Y 5 (NPY5) receptor, for the regulation of food ingestion, preferably for the prophylaxis and/or treatment of disorders of food ingestion, preferably obesity, anorexia or bulimia, for the prophylaxis and/or treatment of disorders of the peripheral nervous system, disorders of the central nervous system, diabetes, arthritis, epilepsy, anxiety, depression, cognitive disorders, preferably memory disorders, cardiovascular diseases, pain, hypertensive syndrom, inflammatory diseases or immune diseases.

The medicament may be in any form suitable for the application to humans and/or animals and can be produced by standard procedures known to those skilled in the art. The composition of the medicament may vary depending on the route of administration.

The medicament of the present invention may e.g. be administered parentally in combination with conventional injectable liquid carriers, such as water or suitable alcohols. Conventional pharmaceutical adjuvants for injection, such as stabilizing agents, solubilizing agents, and buffers, may be included in such injectable compositions. These medicaments may be injected intramuscularly, intraperitoneally, or intravenously.

Medicaments according to the present invention may also be formulated into orally administrable compositions containing one or more physiologically compatible carriers or excipients, in solid or liquid form. These compositions may contain conventional ingredients such as binding agents, fillers, lubricants, and acceptable wetting agents. The compositions may take any convenient form, such as tablets, pellets, capsules, lozenges, aqueous or oily solutions, suspensions, emulsions, or dry powdered form suitable for reconstitution with water or other suitable liquid medium before use, for immediate or controlled release.

The liquid oral forms for administration may also contain certain additives such as sweeteners, flavoring, preservatives, and emulsifying agents. Non-aqueous liquid compositions for oral administration may also be formulated, containing edible oils. Such liquid compositions may be conveniently encapsulated in e.g., gelatin capsules in a unit dosage amount.

The compositions of the present invention may also be administered topically or via a suppository.

The above mentioned compositions include preferably 1 to 60% by weight of one or more of the benzoxazinone-derived compound of general formula (I), optionally in form of one of its stereoisomers, preferably enantiomers or diastereomers, its racemate or in form of a mixture of at least two of its stereoisomers in any mixing ratio, or a physiologically acceptable salt thereof, or a solvate, respectively, and 40 to 99% by weight of the appropriate pharmaceutical vehicle(s).

The daily dosage for humans and animals may vary depending on factors that have their basis in the respective species or other factors, such as age, weight or degree of illness and so forth. The daily dosage for humans usually ranges from 1 milligram to 500 milligram of substace to be administered during one or several intakes.

Pharmacological Methods:

Neuropeptide Y5 Receptor Binding Studies:

Method (I)

The experimental protocol follows the method by M. Gobbi et al. as decribed in M. Gobbi, T. Mennini, A. Vezzani: Autoradiographic Reevaluation of the Binding Properties of [$^{125}$I][Leu$^{31}$, Pro$^{34}$] Peptide YY and [$^{125}$I] Peptide YY$_{3-36}$ to Neuropeptide Y Receptor Subtypes in Rat Forebrain, The Journal of Neurochemistry, 1999, 72, 1663–1670, which is hereby incorporated by reference and is part of the disclosure, with modifications. Male Wistar rats are sacrificed by decapitation, their brains are rapidly removed and the cortex is dissected. Homogenization is performed in cold conditions in the buffer: 120 mM NaCl, 4.7 mM KCl, 2.2 mM CaCl$_2$, 1.2 mM KH$_2$PO$_4$, 1.2 mM MgSO$_4$, 25 mM NaHCO$_3$, 5.5 mM glucose, pH 7.4, by means of a Ultra-Turrax homogenizer for 15 seconds at 13,500 rpm. The ratio between fresh tissue weight and buffer volume is of twenty times. The membrane is centrifuged for 10 min at 48,000 g. The supernatant is discarded and the pellet is washed, resuspended and recentrifuged three more times. The final membrane resuspension is performed in the buffer: 120 mM NaCl, 4.7 mM KCl, 2.2 mM CaCl$_2$, 1.2 mM KH$_2$PO$_4$, 1.2 mM MgSO$_4$, 25 mM NaHCO$_3$, 5.5 mM glucose, 0.1% BSA, 0.05% bacitracin, pH 7.4, at a 20 ml/g ratio of fresh tissue. The radioligand used is [$^{125}$I]-PYY$_{3-36}$ at the concentration of 28 pM. Incubation volume: 500 µl. A 1 µM concentration of BIBP 3226 is added to the incubation medium in order to saturate receptor Y$_1$. Incubation is performed at 25° C. for 120 minutes and ended by rapid filtration in a Harvester Brandel Cell through fiber glass filters of the brand Schleicher & Schuell GF 3362 pretreated with a 0.5% polyethylenimine solution. The filters are cold-washed three times with two milliliters of the same buffer used in homogenization. The filters are transferred to vials and 5 ml of Ecoscint H liquid scintillation cocktail are added to each vial. The vials are allowed to reach steady state for a few hours before counting in a Wallac Winspectral 1414 scintillation counter. Non-specific binding is determined in the presence of 1 μM of pNPY (Neuropeptide Y of porcine origin). The assays are performed in triplicate.

Method (II)

The methods used for membrane preparation and binding are similar to those described by Y. Hu, B. T. Bloomquist et al. in Y. Hu, B. T. Bloomquist et al., The Journal of Biological Chemistry, 1996, 271, 26315–26319 with modifications. Said literature description is herewith incorporated by reference and forms part of the disclosure. Cells C6 were transfected with the rat Y5 receptor. The cells were grown under standard culture conditions in 150 cm$^2$ dishes and they were harvested using a rubber scraper and 10 ml PBS. The cells from five dishes were collected and centrifuged 2.500 g for 5 min (4° C.). The pellet was washed by resuspending in 3 ml buffer (Tris-HCl 10 mM, pH 7.4), homogenized using a Potter S homogenizer, 10 strokes at 600 rpm and centrifuged 48.000 g for 20 min (4° C.). The pellet was resuspended in 8 ml membrane buffer (Tris-HCl 25 mM, NaCl 120 mM, KCl 5 mM, KH$_2$PO$_4$ 1.2 mM, CaCl$_2$ 2.5 mM, MgSO$_4$ 1.2 mM, BSA 0.15 mg/ml, Bacitracine 0.5 mg/ml, pH 7.4) and rehomogenized using the Potter S, 10 strokes at 600 rpm. The protein concentration in the incubation was 40 μg/ml. The radioligand was [$^{125}$I]-PYY (100 pM) in a total incubation volume of 200 μl. Following incubation at 25° C. for 2 h, the reaction was stopped by addition of 5 ml ice-cold buffer (Tris-HCl 25 mM, NaCl 120 mM, KCl 5 mM, KH$_2$PO$_4$ 1.2 mM, CaCl$_2$ 2.5 mM, MgSO$_4$ 1.2 mM, pH 7.4) and rapid filtration in a Harvester Brandell Cell using filters (Schleicher & Schuell GF 3362) pretreated for two hours with 0.5% polyethyleneimine. Filters were washed one time with 5 ml ice-cold buffer. The filters were placed into plastic scintilation vials and 5 ml scintillation cocktail Ecoscint H were added. The quantity of radioactivity present was determined in a Wallac Winspectral 1414 counter. Non specific binding was determined in the presence of 1 μM de pNPY. All binding assays were done in triplicate.

Method (III)

Binding to Neuropeptide Y$_2$

The experimental protocol follows the method by Y. Dumont et al. as described in Y. Dumont, A. Fournier, S. St-Pierre, R. Quirion: Characterization of Neuropeptide Y Binding Sites in Rat Brain Preparations Using [$^{125}$I][Leu$^{31}$, Pro$^{34}$]Peptide YY and [$^{125}$I]Peptide YY$_{3-36}$ as Selective Y1 and Y2 Radioligands, The Journal of Pharmacology and Experimental Therapeutics, 1995, 272, 673–680, with slight modifications. Said literature description is herewith incorporated by reference and forms part of the disclosure.

Male Wistar rats are sacrificed by decapitation, their brains are rapidly removed and the hypoccampus is dissected. Homogenization is performed in cold conditions in the buffer: 120 mM NaCl, 4.7 mM KCl, 2.2 mM CaCl$_2$, 1.2 mM KH$_2$PO$_4$, 1.2 mM MgSO$_4$, 25 mM NaHCO$_3$, 5.5 mM glucose, pH 7.4, by means of a Ultra-Turrax homogenizer for 15 seconds at 13,500 rpm. The ratio between fresh tissue weight and buffer volume is of ten times. The membrane is centrifuged for 10 min at 48,000 g. The supernatant is discarded and the pellet is washed, resuspended and recentrifuged two more times. The final membrane resuspension is performed in the buffer: 120 mM NaCl, 4.7 mM KCl, 2.2 mM CaCl$_2$, 1.2 mM KH$_2$PO$_4$, 1.2 mM MgSO$_4$, 25 mM NaHCO$_3$, 5.5 mM glucose, 0.1% BSA, 0.05% bacitracin, pH 7.4, at a 90 ml/g ratio of fresh issue. The radioligand used is [$^{125}$I]-PYY$_{3-36}$ at the concentration of 28 pM. Incubation volume: 500 μl. Incubation is performed at 25° C. for 150 minutes and ended by rapid filtration in a Harvester Brandel Cell through fiber glass filters of the brand Schleicher & Schuell GF 3362 pretreated with a 0.5% polyethylenimine solution. The filters are cold-washed three times with three milliliters of the same buffer used in homogenization. The filters are transferred to vials and 5 ml of Ecoscint H liquid scintillation cocktail are added to each vial. The vials are allowed to reach steady state for a few hours before counting in a Wallac Winspectral 1414 scintillation counter. Non-specific binding is determined in the presence of 1 μM of pNPY (Neuropeptide Y of porcine origin). The assays are performed in triplicate.

Behavioural Models (Food Intake Measurements)

In both test, animals rats (Male W, 200–270 g, obtained from Harlan, S. A) were used. The rats are acclimatized to the animal facility for at least 5 days before being subjected to any experimental procedure. During this period, animals were housed in groups of five in translucid cages and provided with food and water ad libitum. At least 24 hours before the tests, animals are adapted to single-housing conditions.

Nocturnal Feeding

Food intake is measured in home cages in order to minimize non-specific stress effects on food intake resulting from changes in housing conditions. Food and water is available ad libitum. Immediately before lights turn off, rats are weighed, randomized and dosed (orally or intraperitoneally), either with vehicle or selected benzoxacine-compounds of general formula (I). Thereafter, rats are returned to home cages and food left on top covers is measured. Remaining food and animal's weight is measured next morning.

The above mentioned methods are described in Ants Kask et al., Europan Journal of Pharmacology 414 (2001) 215–224 and Turnbull et al., Diabetes, Vol. 51, August 2002, which are hereby incorporated by reference and form part of the disclosure.

Acute Effects of Selected Compounds on Food Intake in Fasted Rats:

Rats were fasted for 23 hours in home cages, and after this period dosed (orally or intraperitoneally), either with vehicle or benzoxacine-compound of general formula (I). One hour later preweighed food is left on top covers, and cumulative food intake is measured after 1, 2, 4 and 6 hours.

The methods are described in Ants Kask et al., Europan Journal of Pharmacology 414 (2001) 215–224 and Turnbull et al., Diabetes, Vol. 51, August 2002, which are hereby incorporated by reference and form part of the disclosure.

The following examples are given to illustrate the present invention, but they do not limit the scope of the present invention.

EXAMPLES

The intermediates of general formulas (IV) and (V) were prepared by means of conventional organic chemistry methods known to those skilled in the art. The preparation of some of the intermediates of general formulas (IV) and (V) is shown below:

Example A

Synthesis of a Compound of General Formula (IV)

2-chloro-N-(4-phenoxyphenyl)acetamide

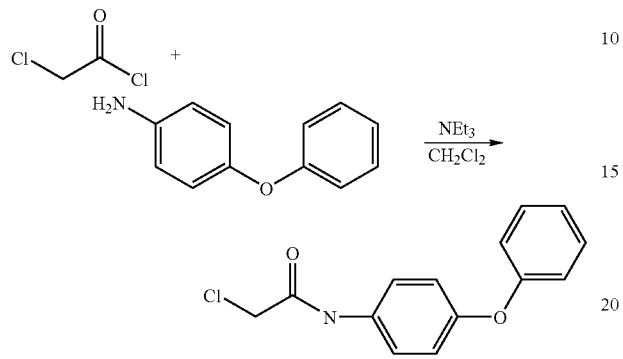

To a solution of 4-phenoxyaniline (1.85 g, 10 mmoles) and triethylamine (2.07 ml, 15 mmoles) in 25 ml dry dichloromethane, is added stepwise a solution of chloroacetyl chloride (1.18 g, 10.5 mmoles) in 10 ml dry dichloromethane. The resulting reaction mixture is stirred for 1 hour at room temperature. Afterwards said reaction mixture is washed with 2×30 ml HCl (2 N) 1×30 ml water, dried with sodium sulfate and the solvent evaporated. 2.48 g. (Yield 95%) of 2-chloro-N-(4-phenoxyphenyl)acetamide were obtained.

IR cm$^{-1}$(KBr): 3270, 1660, 1506, 1490, 1236, 843, 752, 691.

Example B

Synthesis of a Compound of General Formula (V)

Preparation of 6-Chloro-1-(piperidin-4-yl)-1,4-dihydro-2H-3,1-benzoxazin-2-one hydrochloride

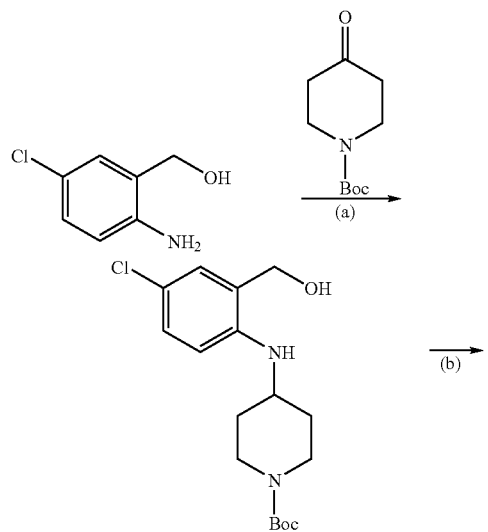

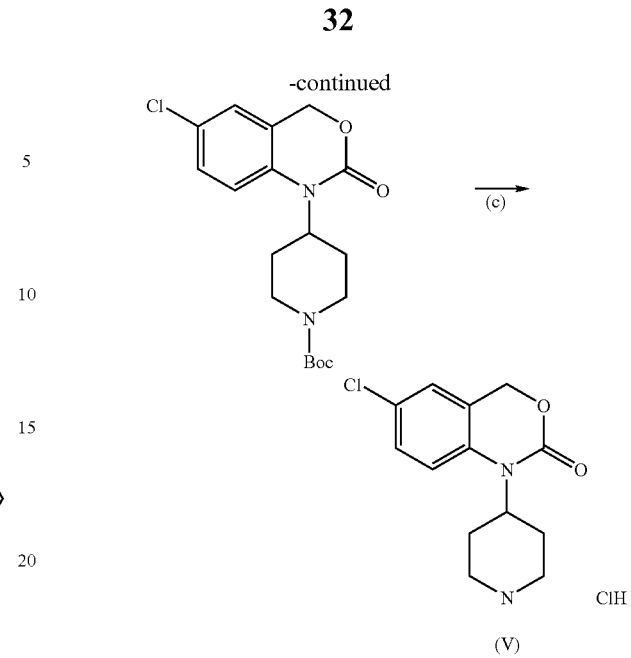

a) 1-(tert-Butyloxycarbonyl)-4-[4-chloro-(2-hydroxymethylphenylamine)]piperidine A solution of 1-(tert-butyloxycarbonyl)-4-piperidinone (20 g, 0.10 mol), 2-amino-5-chlorobenzylic alcohol (17.34 g, 0.11 mol) and acetic acid (14 mL, 0.22 mol) in dry toluene (500 mL) was heated at reflux temperature, with water elimination by means of azeotrope distillation with Dean-Stark, for 6 hours. The mixture was then cooled and vacuum concentrated up to half volume. NaBH$_3$CN (20 g, 0.32 mol) and dry THF (300 mL) were added to the resulting solution. Acetic acid (10 mL, 0.17 mol) was then dripped for one hour. The reaction was stirred at room temperature for 24 hours. The mixture was vacuum concentrated and the residue was dissolved in ethyl acetate (750 mL), washed with a NaHCO$_3$-saturated solution (4×250 mL) and a NaCl-saturated solution (250 mL), dried and evaporated to dryness. The residue was purified by means of flash chromatography eluting with a mixture of ethyl acetate: petroleum ether (1:3). The desired product was thus obtained as an oil (32.7 g, 96%).

$^1$H NMR (CDCl$_3$): 1.32 (d, J=11.2 Hz, 2H), 1.41 (s, 9H), 1.92 (d, J=11.2 Hz, 2H), 2.92 (t, J=12.0 Hz, 1H), 3.10 (s, 1H), 3.37 (m, 1H), 3.88 (d, J=13.7 Hz, 2H), 4.49 (s, 2H), 4.75 (s, 1H), 6.52 (d, J=8.6 Hz, 1H), 6.96 (s, 1H), 7.07 (d, J=8.6 Hz, 1H).

b.) 1-(1-tert-Butyloxycarbonyl-4-piperidinyl)-6-chloro-1,4-dihydro-2H-3,1-benzoxazin-2-one N,N-diisopropylethylamine (DIEA) (43 mL, 0.25 mol) and triphosgene (8.65 g, 29.2 mmol) were added to a solution of 1-(tert-Butyloxycarbonyl)-4-[(4-chloro-(2-hydroxymethyl) phenyl-amino)]piperidine (27.0 g, 79 mmol) in dry THF (250 mL) cooled at 0° C. The reaction was stirred at 0° C. for 1 h and at room temperature for 72 h. Ethyl ether was added and the mixture was cooled at 0° C. for 3 h and the DIEA hydrochloride was then filtered. The filtered solution was evaporated to dryness and the residue was dissolved in ethyl acetate (750 mL), washed with 5% solution of critic acid (2×500 mL), water (250 mL) and NaHCO$_3$-saturated solution (2×500 mL). The ethyl acetate solution was dried (MgSO$_4$), filtered and evaporated under reduced pressure. The residue was brought to the boil with ethyl ether until the whole solid was dissolved and then cooled overnight to yield the desired compound in crystalline form (28.9 g, 67%).

Melting point: 177–179° C.

$^1$H NMR (CDCl$_3$): 1.46 (s, 9H), 1.79 (d, J=10.1Hz, 1H), 2.54 (m, 2H), 2.78 (m, 2H), 3.96 (m, 1H), 4.28 (m, 2H), 5.02 (s, 2H), 6.98 (d, J=8.7 Hz, 1H) 7.13 (d, J=2.4 Hz, 1H), 7.28 (dd, J=8.7 Hz, J=2.4 Hz, 1H).

c.) 6-chloro-1-(piperidin-4-yl)-1,4-dihydro-2H-3,1-benzoxazin-2-one hydrochloride A solution of 1-[(1-tert-Butyloxycarbonyl)-4-piperidinyl]-6-chloro-1,4-dihydro-2H-3,1-benzoxazin-2-one (24 g, 65 mmol) in ethyl acetate (500 mL) was cooled at 0° C. A 5 M solution of hydrogen chloride in ethyl ether (500 mL) was then added and the resulting mixture was stirred at 0° C. for 4 h. The precipitate formed was collected by filtration, washed with ether and vacuum dried to yield the desired product as a solid (16.95 g, 97%).

Melting point: 254–257° C.

$^1$H NMR (CD$_3$OD): 2.13 (d, J=12.2 Hz, 2H), 2.88 (m, 2H), 3.20 (m, 2H), 3.53 (d, J=12.8 Hz, 2H), 4.24 (m, 1H), 5.16 (s, 2H), 7.31 (m, 2H), 7.41 (dd, J=8.8 Hz, J=2.6 Hz, 1H).

Several substituted 3,1-benzoxazin-2-one compounds were prepared via the respectively substituted benzyl alcohols by reducing the respectively substituted anthranilic acids with lithium aluminium hydride and other known reducing agents by methods well known to those skilled in the art (see scheme 2), e.g. por ejemplo 6-methyl-1-(piperidin-4-yl)-1,4-dihydro-2H-3,1-benzoxazin-2-one, 7-methyl-1-(piperidin-4-yl)-1,4-dihydro-2H-3,1-benzoxazin-2-one, 8-methyl-1-(piperidin-4-yl)-1,4-dihydro-2H-3,1-benzoxazin-2-one, 5-methoxy-1-(piperidin-4-yl)-1,4-dihydro-2H-3,1-benzoxazin-2-one, 6-fluoro-1-(piperidin-4-yl)-1,4-dihydro-2H-3,1-benzoxazin-2-one, 8-methoxy-1-(piperidinyl)-1,4-dihydro-2H-3,1-benzoxazin-2-one, 5-methyl-1-(piperidin-4-yl)-1,4-dihydro-2H-3,1-benzoxazin-2-one, 7-fluoro-1-(piperidin-4-yl)-1,4-dihydro-2H-3,1-benzoxazin-2-one, 5-fluoro-1-(piperidin-4-yl)-1,4-dihydro-2H-3,1-benzoxazin-2-one, 6-methoxy-1-(piperidinyl)-1,4-dihydro-2H-3,1-benzoxazin-2-one, 5-chloro-1-(piperidinyl)-1,4-dihydro-2H-3,1-benzoxazin-2-one, 7-chloro-1-(piperidinyl)-1,4-dihydro-2H-3,1-benzoxazin-2-one, 8-chloro-1-(piperidinyl)-1,4-dihydro-2H-3,1-benzoxazin-2-one and others. The reaction of the respective 5-methoxy-1-(piperidinyl)-1,4-dihydro-2H-3,1-benzoxazin-2-one, 8-methoxy-1-(piperidinyl)-1,4-dihydro-2H-3,1-benzoxazin-2-one and 6-methoxy-1-(piperidinyl)-1,4-dihydro-2H-3,1-benzoxazin-2-one compounds according to conventional methods, e.g. BBr$_3$ in an inert organic solvent yields the respective 5-hydroxy-1-(piperidinyl)-1,4-dihydro-2H-3,1-benzoxazin-2-one, 8-hydroxy-1-(piperidinyl)-1,4-dihydro-2H-3,1-benzoxazin-2-one and 6-hydroxy-1-(piperidinyl)-1,4-dihydro-2H-3,1-benzoxazin-2-one compounds. The unsubstituted benzoxazin-2-one 1-(piperidin-4-yl)-1,4-dihydro-2H-3,1-benzoxazin-2-one is prepared according the method described in J. Med. Chem. 1995, 38, 4634 and J. Med. Chem. 1998, 41, 2146, which are hereby incorporated by reference and form part of the disclosure.

The substituted anthranilic acids were reduced by conventional methods known to those skilled in the art, e.g. by the use of LiAlH$_4$ as reducing agent in anhydrous THF under an inert-gas atmosphere, e.g. argon or nitrogen. This process is very efficient and in most cases the respective 2-aminobenzylalcohols are obtained in very good yields.

General instruction for the reduction of substituted anthranilic acids:

To a three neck flask, equipped with a mechanical stirrer and an inlet for gaseous nitrogen, 100 mL anhydrous THF and 116.6 mmoles of LiAlH$_4$ were given and the resulting suspension cooled to 0° C. After the addition of 58.3 mmoles of the respective substituted anthranilic acid in 150 mL anhydrous THF, the resulting reaction mixture is warmed to room temperature and stirred or about an hour. Under cooling to 0° C. 4.7 mL water, 4.7 mL NaOH 15 wt.-%, and finally 14 mL water are carefully added to the mixture. The resulting suspension is filtered and washed with ethylacetate.

The organic phase is washed with water, dried and the solvent evaporated. In most cases the resulting product may be used without further purification.

Example 1

Preparation of 1-{1-[N-(9-oxo-9H-fluoren-2-yl) aminocarbonylmethyl]-4-(piperidinyl)}-1,4-dihydro-2H-3,1-benzoxazin-2-one hydrochloride A mixture of 1-(4-piperidinyl)-1,4-dihydro-2H-3,1-benzoxazinone hydrochloride (2.68 g, 10 mmol), N-(9-oxo-9H-fluoren-2-yl)-2-chloroacetamide (2.99 g, 11 mmol) and K$_2$CO$_3$ (5.53 g, 40 mmol) in DMF (40 mL) was stirred overnight at room temperature. H$_2$O (100 mL) was then added and the precipitate formed was collected by filtration. The solid was dissolved in hot ethyl acetate, washed with water, decanted, dried and evaporated to dryness. The residue dissolved in EtOH was brought to pH=3 with a 1 M solution of hydrogen chloride in EtOH and filtered to yield the desired hydrochloride in crystalline form (3.73 g, 74%).

Example 103

Preparation of N-[4-chloro-2-(2-chloro-benzoyl)-phenyl]-2-[4-(6-chloro-2-oxo-4H-benzo[d][1,3]oxazin-1-yl]-piperidin-1-yl]-acetamide hydrochloride

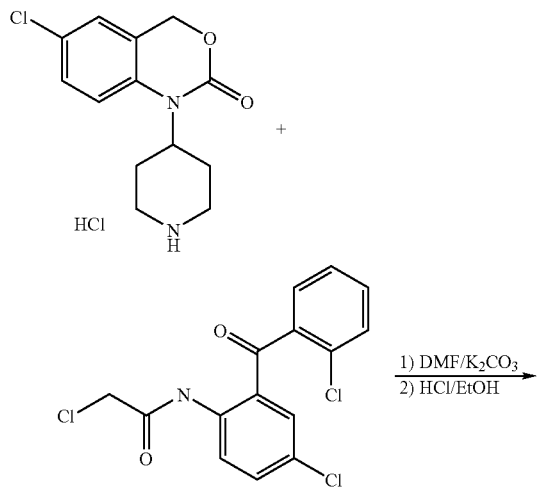

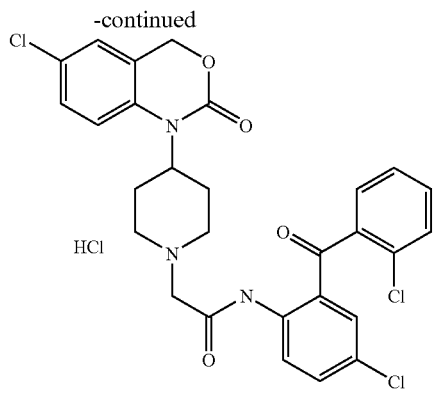

A mixture of 1-(4-piperidinyl)-1,4-dihydro-2H-3,1-benzoxazinone hydrochloride (161 mg, 0.60 mmol), 2-(2-chloroacetamide)-2',5-dichlorobenzophenone (226 mg, 0.66 mmol) and $K_2CO_3$ (330 mg, 2.40 mmol) in DMF (10 mL) is stirred at room temperature overnight. Afterwards $H_2O$ (15 mL) is added and the formed precipitate separated by filtration. The solid is dissolved in ethyl acetate, washed with water, dryed and the solvent evaporated. The so obtained residue is dissolved in ethanol and upon addition of 0.22 ml of a 2.8 M solution of hydrochloric acid in ethanol abs. the hydrochloride salt is crystallized, which was filtered and dryed. 209 mg of a white solid were obtained (Yield 61%).

IR $(cm^{-1})$ KBr: 3385, 3056, 1685, 1607, 1522, 1288, 1238, 1041, 761

$^1$H-NMR: 1.9 (d, J=12.9 Hz, 2H) 2.9 (m, 2H) 3.2 (m, 2H) 3.5 (d, J=11.2 Hz, 2H) 4.0 (s, 2H) 4.2 (m, 1H) 5.0 (s, 2H) 7.3 (m, 4H) 7.4 (m, 1H) 7.5 (m, 2H) 7.5 (m, 1H) 7.6 (dd, J=8.5, 2.4 Hz, 1H) 7.8 (d, J=8.5 Hz, 1H) 10.2 (s, 1H) 10.9 (s, 1H) (DMSO-d6).

Melting point: 201–204° C.

The melting point and the spectroscopic data for the identification of some of the benzoxazinone-derived compounds of general formula (I) prepared analogously to the methods described in Examples 1 and 103, are shown in the following tables:

In the compounds according to examples 1–100 three of the substitutents $R^1$, $R^2$, $R^3$ and $R^4$ as well as the substituents $R^5$ to $R^9$ all represent H. Thus, the general formula (I) may be written in the simplified form (Ia) given below, wherein $R^x$ indicates the respective substituent $R^1$–$R^4$.

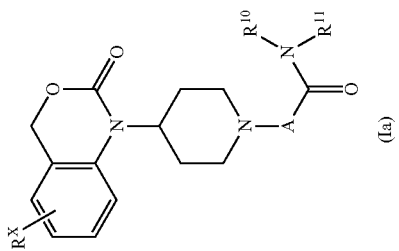
(Ia)
| Ex | R$^X$ | A | R$^{10}$ | R$^{11}$ | Salt | Mp (° C.) | IR cm$^{-1}$ | $^1$H-NMR (300 MHz), δ (solvent) |
|---|---|---|---|---|---|---|---|---|
| 1 | H | CH$_2$ | H | (2-methyl-fluoren-9-one) | HCl | 276–280 | 3241, 1696, 1608, 1560, 1463, 1391, 1293, 1259, 1206, 739. | 2.00(d, J=12.6 Hz, 2H), 2.90(m, J=12.6 Hz, 2H), 3.43(m, 2H), 3.66(d, J=9.7 Hz, 2H), 4.21(m, 3H), 4.28(m, 1H), 5.16(s, 2H), 7.13(m, 1H), 7.34(m, 4H), 7.59(d, J=7.0 Hz, 2H), 7.76(m, 3H), 8.00(s, 1H), 10.26(s, 1H), 11.36(s, 1H), (DMSO-d$_6$) |
| 2 | H | CH$_2$ | H | (2-methyl-fluoren-9-one) | — | 192–194 | 1704, 1611, 1511, 1293, 1205, 768. | 1.74(d, J=10.8 Hz 2H), 2.38(m, 2H), 2.62(m, 2H), 2.99(d, J=11.1 Hz 2H), 3.24(s, 2H), 3.87(m, 1H), 5.12(s, 2H), 7.09(t, J=7.2 Hz, 1H), 7.27(d, J=7.7 Hz, 2H), 7.37(t, J=7.5 Hz, 2H), 7.59(m, 4H), 7.68(d, J=7.5 Hz, 1H), 8.07(s, 1H), 10.22(s, 1H),(DMSO-d$_6$) |
| 3 | H | CH$_2$ | H | (3-methyl-fluoren-9-one) | HCl | >275 | 3433, 1705, 1609, 1557, 1467, 1451, 1297, 1253, 1111, 769 | 2.02(d, J=12.6 Hz, 2H), 2.91(m, J=12.6 Hz, 2H), 3.43(m, 2H), 3.67(d, J=9.9 Hz, 2H), 4.26(m, 3H), 5.16(s, 2H), 7.13(m, 1H), 7.30(d, J=7.5 Hz, 1H), 7.40(m, 3H), 7.64(m, 5H), 8.06(s, 1H), 10.29(s, 1H), 11.46(s, 1H),(DMSO-d$_6$) |

| | | | | | | |
|---|---|---|---|---|---|---|
| 4 | H | CH$_2$ | (4-methylphenyl)(phenyl)methanone structure | — | 133–137 | 3630, 3449, 3249, 1682, 1600, 1516, 1498, 1316, 1282, 1045, 757, 697 | 1.73(d, J=11.7 Hz, 2H), 2.36(m, J=11.2 Hz, 2H), 2.61(m, J=11.7 Hz, 2H), 2.98(d, J=10.8 Hz, 2H), 3.22(s, 2H), 3.87(m, J=11.7 Hz, 1H), 5.11(s, 2H), 7.09(t, J=7.3 Hz, 1H), 7.27(d, J=7.3 Hz, 2H), 7.36(t, J=7.7 Hz, 1H), 7.54(t, J=7.3 Hz, 2H), 7.69(m, 5H), 7.83 (s, 1H), 10.18(s, 1H).(DMSO-d$_6$) |
| 5 | H | CH$_2$ | (4-methylphenyl)(phenyl)methanone structure | HCl | 238–243 | 3457, 1685, 1599, 1542, 1401, 1280, 1034, 700 | 2.00(d, J=11.9 Hz, 2H), 2.91(m, 4H), 3.41(m, 2H), 3.65(d, J=11.2 Hz, 2H), 4.26(m, 3H), 5.16(s, 2H), 7.12(m, 1H), 7.30(d, J=7.5 Hz, 1H), 7.39(d, J=3.8 Hz, 2H), 7.54(m, 2H), 7.68 (m, 3H), 7.81(m, 4H), 10.31(s, 1H), 11.51(s, 1H). (DMSO-d$_6$) |
| 6 | H | CH$_2$ | 6-methyl-tetralone structure | HCl | 260–264 | 3400, 1710 1671, 1592, 1549, 1391, 1260, 1204, 1043, 770 | 1.98(m, 4H), 2.52(m, 2H), 2.91(m, 4H), 3.41(m, 2H), 3.64(m, J=10.4 Hz, 2H), 4.25(m, 3H), 5.16(s, 2H), 7.14(m, 1H), 7.30(d, J=7.3 Hz, 1H), 7.40(m, 2H), 7.58(m, 2H), 7.86(d, J=8.6 Hz, 1H), 10.22(s, 1H), 11.15(s, 1H). (DMSO-d$_6$) |
| 7 | H | CH$_2$ | methyl-fluorenone structure | HCl | 270–273 | 1710, 1698, 1608, 1541, 1466, 1390, 1292, 1263, 1201, 737 | 2.03(d, J=12.1 Hz, 2H), 2.90(m, J=11.2 Hz, 2H), 3.49(m, 2H), 3.70(d, J=11.2 Hz, 2H), 4.29(m, 1H), 4.40(s, 2H), 5.16(s, 2H), 7.14(m, 1H), 7.30(d, J=7.3 Hz, 1H), 7.42(m, 4H), 7.61(m, 4H), 7.82(d, J=7.1 Hz, 1H), 10.29(s, 1H), 10.96(s, 1H). (DMSO-d$_6$) |
| 8 | H | CH$_2$ | (3-methylphenyl)(phenyl)methanone structure | HCl | 214–218 | 3447, 1686, 1609, 1592, 1298, 1208, 1043, 721 | 2.00(d, J=12.1 Hz, 2H), 2.36(m, J=11.0 Hz, 2H), 2.89(m, J=Hz, 2H), 3.33(m, 2H), 3.64(d, J=10.6 Hz, 2H), 4.17(m, 1H), 4.26(m, 1H), 5.16(s, 2H), 7.13(m, 1H), 7.34(m, 3H), 7.54(m, 4H), 7.71(m, 3H), 7.86(d, J=8.1 Hz, 1H), 8.08(s, 1H), 10.17(s, 1H), 10.99(s, 1H). (DMSO-d$_6$) |
| 9 | H | CH$_2$ | methyl-indanone structure | — | 206–209 | 3327, 1720, 1696, 1592, 1514, 1285, 1206, 1045, 768, 753 | 1.73(d, J=11.5 Hz, 2H), 2.36(m, 4H), 2.59(m, 4H), 2.97(d, J=10.8 Hz, 2H), 3.05(m, 2H), 3.21(s, 2H), 3.86(m, 1H), 5.11(s, 2H), 7.09(t, J=7.2 Hz, 1H), 7.27(d, J=7.5 Hz, 2H), 7.36 (m, 1H), 7.58(s, 2H), 7.95(s, 1H), 10.14(s, 1H). (DMSO-d$_6$) |

| # | R1 | R2 | Structure | Salt | mp (°C) | IR | NMR |
|---|---|---|---|---|---|---|---|
| 10 | H | CH₂ | indanone (5-methyl) | HCl | 272–277 | 3463, 1709, 1595, 1555, 1390, 1284, 1256, 1204, 1042, 771 | 2.00(d, J=12.4 Hz, 2H), 2.60(m, 2H), 2.90(m, 2H), 3.07(m, 2H), 3.41(m, 2H), 3.63(m, 2H), 4.25(m, 3H), 5.16(s, 2H), 7.12(m, 1H), 7.30(d, J=7.1 Hz, 1H), 7.38(d, J=3.7 Hz, 2H), 7.63 (s, 2H), 7.94(s, 1H), 10.28(s, 1H), 11.48(s, 1H). (DMSO-d₆) |
| 11 | H | CH₂ | indane (5-methyl) | HCl | 230–231 | 2249, 1701, 1607, 1558, 1496, 1394, 1292, 1206, 1042, 771 | 1.99(m, 4H), 2.83(m, 6H), 3.43(m, 2H), 3.63(d, J=10.1 Hz, 2H), 4.17(s, 2H), 4.29(m, 1H), 5.15(s, 2H), 7.15(m, 3H), 7.30(d, J=7.5 Hz, 1H), 7.37(m, 3H), 7.54(s, 1H), 10.24(s, 1H), 10.95(s, 1H). (DMSO-d₆) |
| 12 | H | CH₂ | dibenzofuran (MeO, methyl) | HCl | 182–187 | 3448, 1592, 1560, 1432, 1400, 1299, 1209, 1043, 770, 721 | 2.02(d, J=12.8 Hz, 2H), 2.91(m, J=10.6 Hz, 2H), 3.45(m, 2H), 3.68(d, J=12.1 Hz, 2H), 3.99(s, 3H), 4.29(s, 2H), 4.42(m, 1H), 5.16(s, 2H), 7.10–8.40(10 H), 10.18(s, 1H), 11.18(s, 1H). (DMSO-d₆) |
| 13 | H | CH₂ | cyclohexyl-phenyl (methyl) | HCl | 256–260 | 3422, 1701, 1609, 1550, 1393, 1292, 1260, 1205, 1043 | 1.29(m, 5H), 1.72(m, 5H), 2.00(d, J=13.2 Hz, 2H), 2.45(m, 1H), 2.91(m, J=11.7 Hz, 2H), 3.39(m, 2H), 3.64(m, 2H), 4.16(s, 2H), 4.30(m, 1H), 5.15(s, 2H), 7.13(m, 3H), 7.29(d, J=7.3 Hz, 1H), 7.38(d, J=8.2 Hz, 2H), 10.28(s, 1H), 10.96(s, 1H). (DMSO-d₆) |
| 14 | H | CH₂ | o-tolyl-CH₂CH₂ | HCl | 198–203 | 3427, 1677, 1497, 1390, 1297, 1205, 1039, 753 | 1.91(m, 4H), 2.73(t, J=6.5 Hz, 2H), 2.93(m, J=11.4 Hz, 2H), 3.40 (m, 2H), 3.66(m, 4H), 4.28(m, 1H), 4.52(m, 2H), 5.15(s, 2H), 7.25 (m, 8H), 10.18(s, 1H). (DMSO-d₆) |
| 15 | H | CHC₆H₅ | fluorenone (methyl) | HCl | 247–249 | 3435, 1709, 1691, 1608, 1561, 1298, 766, 743 | 1.91(d, J=12.0 Hz, 2H), 2.06(d, J=12.8 Hz, 1H), 2.94(m, 3H), 3.23(m, 1H), 3.45(m, 1H), 3.78(m, 1H), 4.32(m, 1H), 5.14(s, 2H), 5.49(s, 1H), 7.12(m, 1H), 7.28(d, J=7.3 Hz, 1H), 7.38(m, 3H), 7.59(m, 8H), 7.80(m, 2H), 8.07(s, 1H), 10.73(s, 1H), 12.16(s, 1H). (DMSO-d₆) |
| 16 | H | CHCH₃ | fluorenone (methyl) | HCl | 242–252 | — | 1.62(d, J=6.4 Hz, 3H), 2.05(d, J=13.0 Hz, 2H), 2.91(m, 2H), 3.57 (m, 2H), 4.35(m, 2H), 5.16(s, 2H), 7.12(m, 1H), 7.38(m, 4H), 7.65 (m, 5H), 8.14(s, 1H), 10.35(s, 1H), 11.77(s, 1H). (DMSO-d₆) |

| # | R | X | Structure | Salt | mp (°C) | IR | NMR |
|---|---|---|---|---|---|---|---|
| 17 | H | CH₂ | 3-methyl-9-ethylcarbazole | — | 212–214 | 3298, 2975, 1713, 1684, 1531, 1492, 1208, 1040, 768, 747 | 1.29(t, J=7.0 Hz, 3H), 1.77(d, J=10.6 Hz, 2H), 2.39(m, 2H), 2.66 (m, 2H), 3.04(d, J=11.6 Hz, 2H), 3.20(s, 2H), 3.90(m, 1H), 3.04 (d, J=11.0 Hz, 2H), 5.13(s, 2H), 7.10(t, J=7.5 Hz, 1H), 4.41(q, J=7.0 Hz, 2H), 7.29(m, 2H), 7.41(m, 2H), 7.58(m, 3H), 8.07(d, J=7.5 Hz, 1H), 8.42(s, 1H), 9.76(s, 1H). (DMSO-d₆) |
| 18 | H | CH₂ | 3-methyl-9-ethylcarbazole | HCl | 246–250 | 3248, 2966, 1683, 1608, 1493, 1299, 1226, 1040, 771, 745 | 1.28(t, J=6.8 Hz, 3H), 2.00(d, J=11.9 Hz, 3H), 2.93(m, J= 11.5 Hz, 2H), 3.43(m, 2H), 3.69(d, J=10.3 Hz, 2H), 4.28(m, 3H), 4.41 (q, J=6.8 Hz, 2H), 5.16(s, 2H), 7.15(m, 2H), 7.30(d, J=7.3 Hz, 1H), 7.41(m, 3H), 7.62(m, 3H), 8.05(d, J=7.9 Hz, 1H), 8.47(s, 1H), 10.33(s, 1H), 11.15(s, 1H). (DMSO-d₆) |
| 19 | 6-CH₃ | CH₂ | fluorenone | — | 237–239 | 1706, 1611, 1596, 1508, 1292, 1214 | 1.72(d, J=11.7 Hz, 2H), 2.25(s, 3H), 2.38(m, 2H), 2.62(m, 2H), 2.99(d, J=11.0 Hz, 2H), 3.23(s, 2H), 3.85(m, 1H), 5.06(s, 2H), 7.06(s, 1H), 7.15(s, 2H), 7.37(t, J=7.3 Hz, 1H), 7.58(m, 4H), 7.67 (d, J=7.3 Hz, 1H), 8.06(s, 1H), 10.17(s, 1H). (DMSO-d₆) |
| 20 | 6-CH₃ | CH₂ | fluorenone | HCl | 250–252 | 3411, 1707, 1683, 1608, 1551, 1296, 1252, 1111 | 1.99(d, J=13.4 Hz, 2H), 2.27(s, 3H), 2.89(m, 2H), 3.42(m, 2H), 3.67(m, 2H), 4.28(m, 3H), 5.11(s, 2H), 7.09(m, 1H), 7.18(d, J= 8.4 Hz, 1H), 7.28(d, J=8.4 Hz, 1H), 7.39(t, J=7.3 Hz, 1H), 7.61 (m, 5H), 8.07(s, 1H), 10.35(s, 1H), 11.65(s, 1H). (DMSO-d₆) |
| 21 | 6-CH₃ | CH₂ | 3-methyl-9-ethylcarbazole | HCl | 247–252 | 1683, 1492, 1460, 1299, 1225 | 1.29(t, J=7.0 Hz, 3H), 2.00(d, J=11.9 Hz, 3H), 2.27(s, 3H), 2.91 (m, J=11.2 Hz, 2H), 3.42(m, 2H), 3.68(d, J=10.4 Hz, 2H), 4.22 (m, 3H), 4.42(q, J=7.1 Hz, 2H), 5.11(s, 2H), 7.10(m, 1H), 7.18 (m, 2H), 7.30(d, J=8.4 Hz, 1H), 7.45(m, 1H), 7.60 (m, 3H), 8.05 (d, J=7.9 Hz, 1H), 8.46(s, 1H), 10.29(s, 1H), 11.09(s, 1H). (DMSO-d₆) |
| 22 | 6-CH₃ | CH₂ | 4-cyclohexylphenyl | — | 155–157 | 2923, 2849, 1711, 1519, 1294, 1217, 1046 | 1.29(m, 5H), 1.72(m, 7H), 2.25(m, 3H), 2.36(m, 3H), 2.58(m, 2H), 2.95(d, J=10.8 Hz, 2H), 3.12(s, 2H), 3.83(m, 1H), 5.06(s, 2H), 7.06(s, 1H), 7.13(m, 4H), 7.51(d, J=8.2 Hz, 2H), 9.64(s, 1H). (DMSO-d₆) |

| # | R | X | Structure | Salt | mp | IR | NMR |
|---|---|---|---|---|---|---|---|
| 23 | 6-CH$_3$ | CH$_2$ | 4-cyclohexylphenyl | HCl | 242–246 | 3428, 2925, 1711, 1691, 1507, 1293, 1218, 1039, 827, 767 | 1.27(m, 5H), 1.71(m, 5H), 1.95(d, J=12.0 Hz, 2H), 2.26(s, 3H), 2.43(m, 1H), 2.89(m, 2H), 3.41(m, 2H), 3.57(m, 2H), 4.17(m, 2H), 4.26(m, 1H), 5.10(s, 2H), 7.09(s, 1H), 7.17(d, J=8.6 Hz, 2H), 7.18(d, J=8.6 Hz, 1H), 7.29(d, J=8.4 Hz, 2H), 7.55(d, J=8.4 Hz, 2H), 11.11(s, 1H). (DMSO-d$_6$) |
| 24 | 6-CH$_3$ | CH$_2$ | 4-benzoylphenyl | HCl | 240–244 | 3432, 2995, 1702, 1686, 1539, 1314, 1281, 1039, 700 | 1.99(d, J=11.3 Hz, 2H), 2.27(s, 3H), 2.90(m, 2H), 3.42(m, 2H), 3.65(m, 2H), 4.27(m, 3H), 5.11(s, 2H), 7.10(s, 1H), 7.18(d, J=8.2 Hz, 1H), 7.29(d, J=8.2 Hz, 2H), 7.55(t, J=7.3 Hz, 2H), 7.66(m, 3H), 7.77(d, J=8.8 Hz, 2H), 7.86(d, J=8.4 Hz, 2H), 10.35(s, 1H), 11.61(s, 1H). (DMSO-d$_6$) |
| 25 | H | CH$_2$ | N-methylcarbazolyl | HCl | 191–193 | 3425, 3048, 1709, 1686, 1607, 1496, 1248, 1040, 771, 750 | 2.03(d, J=12.4 Hz, 2H), 2.93(m, 3H), 3.42(m, 2H), 3.69(m, 2H), 3.86(s, 3H), 4.22(s, 2H), 4.32(m, 1H), 5.17(s, 2H), 7.13(m, 1H), 7.20(d, J=7.3 Hz, 1H), 7.30(d, J=10.2 Hz, 2H), 7.43(m, 3H), 7.58(d, J=7.7 Hz, 1H), 8.06(d, J=8.6 Hz, 1H), 8.47(s, 1H), 11.09(s, 1H). (DMSO-d$_6$) |
| 26 | H | CH$_2$ | anthraquinonyl | HCl | 280–282 | 3466, 3078, 1679, 1591, 1551, 1332, 1293, 1201, 917, 725 | 2.03(d, J=12.1 Hz, 2H), 2.92(m, 2H), 3.43(m, 2H), 3.69(d, J=9.7 Hz, 2H), 4.29(m, 3H), 5.16(s, 2H), 7.14(m, 1H), 7.30(d, J=7.3 Hz, 2H), 7.39(d, J=7.3 Hz, 1H), 7.39(d, J=3.8 Hz, 3H), 7.92(m, 2H), 8.08(d, J=8.2 Hz, 1H), 8.21(m, 3H), 8.57(s, 1H), 10.30(s, 1H), 11.65(s, 1H). (DMSO-d$_6$) |
| 27 | H | CH$_2$ | 4-(N-ethyl-N-phenylamino)phenyl | HCl | 254–257 | 3432, 2980, 1714, 1689, 1508, 1492, 1258, 1204, 770, 753 | 1.09(t, J=7.0 Hz, 3H), 2.00(d, J=12.1 Hz, 2H), 2.90(m, J=11.3 Hz, 2H), 3.37(m, 2H), 3.63(q, J=7.0 Hz, 2H), 3.71(q, J=7.0 Hz, 2H), 4.15(s, 2H), 4.29(m, 1H), 5.16(s, 2H), 6.84(m, 3H), 7.01(d, J=9.0 Hz, 2H), 7.12(m, 1H), 7.20(m, 2H), 7.30(d, J=7.3 Hz, 1H), 7.39(d, J=3.8 Hz, 2H), 7.56(d, J=8.8 Hz, 2H), 10.23(s, 1H), 10.92(s, 1H). (DMSO-d$_6$) |
| 28 | 6-CH$_3$ | CH$_2$ | 4-(N-ethyl-N-phenylamino)phenyl | HCl | 226–230 | 2976, 1708, 1690, 1509, 1378, 1291, 1256, 1216, 1040, 766 | 1.09(t, J=7.0 Hz, 3H), 1.98(d, J=13.0 Hz, 2H), 2.27(s, 3H), 2.88(m, J=11.3 Hz, 2H), 3.41(m, 2H), 3.63(d, J=11.2 Hz, 2H), 3.70(q, J=7.0 Hz, 2H), 4.15(s, 2H), 4.26(m, 1H), 5.10(s, 2H), 6.84(m, 3H), 7.00(d, J=9.0 Hz, 2H), 7.10(m, 1H), 7.19(m, 2H), 7.25(m, 2H), 7.57(d, J=8.8 Hz, 2H), 10.24(s, 1H), 10.97(s, 1H). (DMSO-d$_6$) |

| | | | | | | |
|---|---|---|---|---|---|---|
| 29 | H | CH$_2$ | 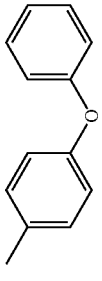 | HCl | 242–248 | 3044, 1703, 1686, 1506, 1487, 1392, 1226, 1040, 751, 694 | 2.01(d, J=12.8 Hz, 2H), 2.90(m, J=12.1 Hz, 2H), 3.41(m, 2H), 3.63(m, 2H), 4.18(s, 2H), 4.29(m, 1H), 5.16(s, 2H), 6.96(m, 2H), 7.03(m, 2H), 7.12(m, 2H), 7.35(m, 5H), 7.67(d, J=8.8 Hz, 2H), 10.26(s, 1H), 11.13(s, 1H). (DMSO-d$_6$) |
| 30 | H | CH$_2$ | 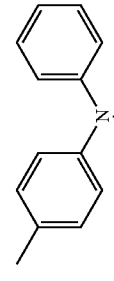 | HCl | 171–173 | 3399, 2976, 1707, 1655, 1498, 1321, 1254, 1117, 753 | 1.02(d, J=6.6 Hz, 6H), 1.92(d, J=12.4 Hz, 2H), 2.86(m, J=10.6 Hz, 2H), 3.18(m, J=11.5 Hz, 2H), 3.50(m, J=11.5 Hz, 2H), 3.65(s, 2H), 4.14(m, 1H), 4.78(hp, J=6.6 Hz, 1H), 5.14(s, 2H), 6.90(d, J=7.2 Hz, 1H), 7.12(m, 6H), 7.30(m, 6H), 8.61(s, 1H), 9.85(s, 1H). (DMSO-d$_6$) |
| 31 | H | CH$_2$CH$_2$ | 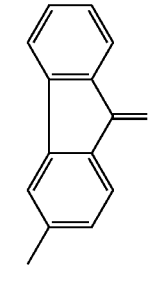 | HCl | 240–242 | — | 2.03(d, J=12.5 Hz, 2H), 2.85(m, J=12.3 Hz, 2H), 3.04(m, 2H), 3.24(m, J=12.1 Hz, 2H), 3.44(m, 2H), 3.60(d, J=11.4 Hz, 2H), 4.29(m, 1H), 5.16(s, 2H), 7.13(m, 1H), 7.30(d, J=6.8 Hz, 1H), 7.38(m, 3H), 7.62(m, 4H), 8.07(s, 1H), 10.15(s, 1H), 10.97(s, 1H). (DMSO-d$_6$) |
| 32 | 6-Cl | CH$_2$ | 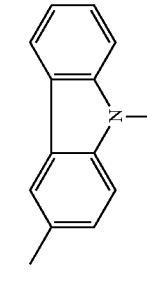 | HCl | 265–268 | 2970, 1712, 1691, 1492, 1376, 1294, 1201, 1043 | 1.28(t, J=7.0 Hz, 3H), 2.01(d, J=12.4 Hz, 2H), 2.90(m, 2H), 3.43(m, 2H), 3.68(m, 2H), 4.27(m, 3H), 4.41(q, J=7.0 Hz, 2H), 5.16(s, 2H), 7.17(t, J=7.4 Hz, 1H), 7.44(m, 4H), 7.61(m, 3H), 8.05(d, J=7.9 Hz, 1H), 8.47(s, 1H), 10.33(s, 1H), 11.16(s, 1H). (DMSO-d$_6$) |
| 33 | H | CH$_2$ | 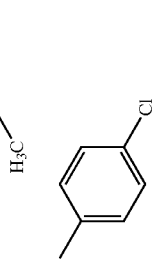 | HCl | 272–276 | 3454, 3057, 1701, 1610, 1552, 1492, 1394, 1292, 1254, 1024 | 1.99(d, J=12.4 Hz, 2H), 2.90(m, J=11.5 Hz, 2H), 3.40(m, 2H), 3.63(d, J=11.0 Hz, 2H), 4.20(s, 2H), 4.28(m, 1H), 5.15(s, 2H), 7.12(m, 1H), 7.29(d, J=7.3 Hz, 1H), 7.40(m, 4H), 7.69(d, J=8.8 Hz, 2H), 10.28(s, 1H), 11.35(s, 1H). (DMSO-d$_6$) |
| 34 | 6-Cl | CH$_2$ | 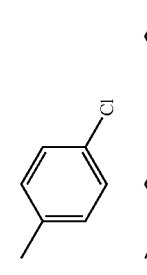 | HCl | 279–282 | 3026, 1713, 1698, 1612, 1553, 1491, 1294, 1253, 1199, 1042 | 1.99(d, J=12.7 Hz, 2H), 2.86(m, 2H), 3.41(m, 2H), 3.62(d, J=10.4 Hz, 2H), 4.18(s, 2H), 4.27(m, 1H), 5.16(s, 2H), 7.40(m, 5H), 7.68(d, J=8.8 Hz, 2H), 10.26(s, 1H), 11.24(s, 1H).(DMSO-d$_6$) |
| 35 | 8-CH$_3$ | CH$_2$ | 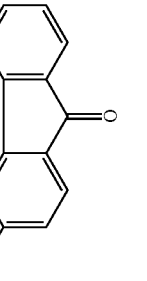 | HCl | 233–236 | 3410, 3014, 1701, 1609, 1561, 1450, 1371, 1285, 1237, 1109, 916, 768, 731 | 2.13(d, J=12.8 Hz, 2H), 2.40(s, 3H), 2.91(m, 2H), 3.42(m, 2H), 3.63(d, J=10.2 Hz, 2H), 3.84(m, 1H), 4.25(s, 2H), 5.09(s, 2H), 7.10(m, 2H), 7.25(d, J=6.8 Hz, 1H), 7.38(t, J=7.4 Hz, 1H), 7.62(m, 5H), 8.07(s, 1H), 10.27(s, 1H), 11.75(s, 1H). (DMSO-d$_6$) |

| | | | | | | |
|---|---|---|---|---|---|---|
| 36 | 6-Cl | CH$_2$ | H |  | 245–249 | 3421, 1701, 1609, 1560, 1371, 1298, 1201 | 2.01(d, J=11.8 Hz, 2H), 2.88(m, 2H), 3.42(m, 2H), 3.66(d, J= 11.8 Hz, 2H), 4.30(m, 3H), 5.16(s, 2H), 7.39(m, 4H), 7.60(m, 5H), 8.08(s, 1H), 10.39(s, 1H), 11.75(s, 1H),(DMSO-d$_6$) |
| 37 | 8-CH$_3$ | CH$_2$ | H | 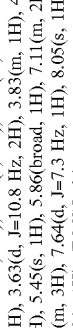 | 207–212 | 3435, 1679, 1390, 1263, 774 | 2.13(d, J=13.3 Hz, 2H), 2.40(s, 3H), 2.91(m, 2H), 3.36(m, 2H), 3.63(d, J=10.8 Hz, 2H), 3.83(m, 1H), 4.18(s, 2H), 5.09(s, 2H), 5.45(s, 1H), 5.86(broad, 1H), 7.11(m, 2H), 7.33(m, 3H), 7.55(m, 3H), 7.64(d, J=7.3 Hz, 1H), 8.05(s, 1H), 10.19(s, 1H), 11.22(s, 1H). (DMSO-d$_6$) |
| 38 | H | CH$_2$ | H |  | >225 (dec). | 3406, 3059, 1702, 1604, 1461, 1395, 1205, 1042, 769, 739 | 2.01(d, J=12.8 Hz, 2H), 2.91(m, 2H), 3.42(m, 2H), 3.66(d, J= 9.6 Hz, 2H), 4.22(s, 2H), 4.29(m, 1H), 5.16(s, 2H), 5.45(s, 1H), 5.92(broad, 1H), 7.12(m, 1H), 7.32(m, 5H), 7.55(d, J= 7.2 Hz, 1H), 7.62(d, J=8.1 Hz, 1H), 7.72(m, 2H), 7.96(s, 1H), 10.27 (s, 1H), 11.17(s, 1H). (DMSO-d$_6$) |
| 39 | 6-Cl | CH$_2$ | H | 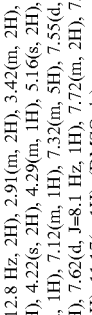 | 219–222 | 3422, 3045, 1701, 1559, 1491, 1295, 1200, 1042 | 2.01(d, J=11.9 Hz, 2H), 2.88(m, 2H), 3.39(m, 2H), 3.66(d, J= 9.8 Hz, 2H), 4.27(m, 3H), 5.16(s, 2H), 5.45(s, 1H), 5.86(broad, 1H), 7.36(m, 5H), 7.54(m, 3H), 7.64(d, J=7.2 Hz, 1H), 8.06(s, 1H), 10.28(s, 1H), 11.17(s, 1H). (DMSO-d$_6$) |
| 40 | 8-CH$_3$ | CH$_2$ | H |  | 229–232 | 3449, 2976, 1710, 1685, 1490, 1384, 1326, 1225, 953, 745 | 1.28(t, J=7.0 Hz, 3H), 2.13(d, J=12.8 Hz, 2H), 2.40(s, 3H), 2.92 (m, 2H), 3.40(m, 2H), 3.64(d, J=11.0 Hz, 2H), 3.84(m, 1H), 4.17 (s, 2H), 4.41(q, J=7.0 Hz, 2H), 5.09(s, 2H), 7.13(m, 3H), 7.25(d, J=7.3 Hz, 1H), 7.44(m, 1H), 7.60(m, 1H), 8.05(d, J=7.7 Hz, 1H), 8.43(s, 1H), 10.18(s, 1H), 11.09(s, 1H). (DMSO-d$_6$) |
| 41 | 8-CH$_3$ | CH$_2$ | H | 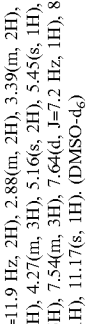 | 264–274 | 3449, 1698, 1703, 1610, 1556, 1327, 1119, 1065, 952, 844 | 2.1 (d, J=12.7 Hz, 2 H) 2.4(s, 3 H) 2.9(m, 2 H) 3.4(m, 2 H) 3.6(d, J=12.0 Hz, 2 H) 3.8(t, J=11.5 Hz, 1 H) 4.1(s, 2 H) 5.1(s, 2 H) 7.1 (m, 2 H) 7.2(d, J=7.1 Hz, 1 H) 7.7(d, J=8.5 Hz, 2 H) 7.8(s, 2 H) 10.2(s, 1 H) 11.1(s, 1 H). (DMSO-d$_6$) |
| 42 | 8-CH$_3$ | CH$_2$ | H |  | 232–239 | 3190, 1696, 1599, 1556, 951, 773, 726, 694 | 2.1(d, J=13.7 Hz, 2 H) 2.4(s, 3 H) 3.0(m, 2 H) 3.2(s, 2 H) 3.6(m, 2 H) 3.8(m, 1 H) 4.1(s, 2 H) 5.0(s, 2 H) 7.1(m, 3 H) 7.2(d, J= 7.8 Hz, 1 H) 7.3(t, J=6.5 Hz, 2 H) 7.6(d, J=8.1 Hz, 2 H) 10.1(s, 1 H) 10.6(s, 1 H). (DMSO-d$_6$) |

| # | R1 | X | Ar | Salt | mp | IR | NMR |
|---|---|---|---|---|---|---|---|
| 43 | H | CH₂ | 4-CF₃-C₆H₄ | HCl | 276–284 | 3407, 3055, 1708, 1610, 1555, 1324, 1112, 1065, 948, 845 | 2.0(d, J=13.9 Hz, 2 H) 2.9(q, J=12.0 Hz, 2 H) 3.3(m, 2 H) 3.6(d, J=12.2 Hz, 2 H) 4.2(s, 2 H) 4.3(d, J=12.2 Hz, 1 H) 5.1(s, 2 H) 7.1(m, 1 H) 7.2(d, J=7.3 Hz, 1 H) 7.3(d, J=3.7 Hz, 2 H) 7.6(d, J=8.8 Hz, 2 H) 7.8(m, 2 H) 10.2(s, 1 H) 10.9(s, 1 H). (DMSO-d₆) |
| 44 | 6-Cl | CH₂ | C₆H₅ | HCl | 265–277 | 3001, 2494, 1712, 1696, 1602, 1559, 1259, 1041, 966, 760 | 2.0(d, J=13.9 Hz, 2 H) 2.9(m, 2 H) 3.3(m, 2 H) 3.6(d, J=12.2 Hz, 2 H) 4.1(s, 2 H) 4.3(m, 1 H) 5.1(s, 2 H) 7.1(t, J=7.3 Hz, 1 H) 7.3(m, 2 H) 7.4(m, 3 H) 7.6(d, J=7.6 Hz, 2 H) 10.1(s, 1 H) 10.6(s, 1 H). (DMSO-d₆) |
| 45 | 6-Cl | CH₂ | 4-CF₃-C₆H₄ | HCl | 284–285 | 2993, 2500, 1707, 1611, 1557, 1325, 1112, 1064, 949, 845 | 2.0(d, J=12.9 Hz, 2 H) 2.9(q, J=13.2 Hz, 2 H) 3.3(m, 2 H) 3.6(d, J=13.2 Hz, 2 H) 4.2(s, 2 H) 4.3(m, 1 H) 5.1(s, 2 H) 7.4(m, 3 H) 7.7(m, 2 H) 7.8(m, 2 H) 10.2(s, 1 H) 11.0(s, 1 H). (DMSO-d₆) |
| 46 | H | CH₂ | C₆H₅ | HCl | 262–272 | 3405, 3068, 1707, 1609, 1557, 1325, 1043, 947, 761 | 2.0(d, J=13.4 Hz, 2 H) 2.9(m, 2 H) 3.3(m, 2 H) 3.6(d, J=11.7 Hz, 2 H) 4.1(s, 2 H) 4.3(m, 1 H) 5.1(s, 2 H) 7.1(dd, J=7.3, 5.9 Hz, 2 H) 7.3(m, 5 H) 7.6(d, J=8.5 Hz, 2 H) 10.1(s, 1 H) 10.6(s, 1 H). (DMSO-d6) |
| 47 | 8-CH₃ | CH₂ | 4-Cl-C₆H₄ | HCl | 245–253 | 3277, 2991, 1726, 1681, 1597, 1541, 1492, 1280, 1255, 1201 | 2.1(d, J=13.2 Hz, 2 H) 2.4(s, 3 H) 2.9(m, 2 H) 3.3(m, 2 H) 3.6(d, J=2.9 Hz, 2 H) 3.8(m, 1 H) 4.1(s, 2 H) 5.0(s, 2 H) 7.1(m, 2 H) 7.2(d, J=7.1 Hz, 2 H) 7.3(d, J=7.1 Hz, 2 H) 7.6(m, 2 H) 10.2 (s, 1 H) 10.8(s, 1 H). (DMSO-d₆) |
| 48 | H | CH₂ | 4-CN-C₆H₄ | HCl | 268–282 | 3401, 2992, 2217, 1708, 1600, 1538, 1391, 1042, 950, 842 | 2.0(d, J=12.7 Hz, 2 H) 2.9(m, 2 H) 3.3(m, 2 H) 3.4(m, 3 H) 3.7(d, J=11.5 Hz, 2 H) 4.3(m, 1 H) 5.1(s, 2 H) 7.1(m, 1 H) 7.3(d, J=7.8 Hz, 1 H) 7.4(m, 2 H) 7.8(m, 4 H) 10.2(s, 1 H) 11.1(s, 1 H). (DMSO-d6) |
| 49 | 8-CH₃ | CH₂ | 4-CN-C₆H₄ | HCl | 229–234 | 3448, 2978, 2223, 1707, 1600, 1541, 1035, 839 | 2.1(d, J=13.4 Hz, 2 H) 2.4(s, 3 H) 2.9(m, 2 H) 3.3(m, 2 H) 3.8(t, J=11.0 Hz, 1 H) 4.1(s, 2H) 5.1(s, 2H) 7.1(m, 2 H) 7.2(d, J=6.4 Hz, 1 H) 7.7(m, 4 H) 10.2(s, 1 H) 11.1(s, 1 H). (DMSO-d6) |
| 50 | 6-Cl | CH₂ | 4-CN-C₆H₄ | HCl | 274–278 | 3414, 2986, 2219, 1721, 1602, 1541, 1313, 1200, 1040, 842 | 2.0(d, J=12.6 Hz, 2 H) 2.9(m, 2 H) 3.3(m, 2 H) 4.2(s, 2 H) 4.3(m, 1H) 5.1(s, 2 H) 7.4(m, 3 H) 7.8(s, 4 H) 10.2(s, 1H) 11.0(s, 1 H). (DMSO-d6) |

| # | R | X | Structure | Salt | mp (°C) | IR | NMR |
|---|---|---|---|---|---|---|---|
| 51 | H | CH$_2$ | 4-acetylphenyl | HCl | >280 | 3448, 3044, 1708, 1600, 1395, 1261, 1043, 948, 842, 771 | 2.0(d, J=13.5 Hz, 2 H) 2.5(s, 3 H) 2.9(m, 2 H) 3.3(m, 2 H) 3.6(d, J=11.4 Hz, 2 H) 4.1(s, 2 H) 4.3(m, 1 H) 5.1(s, 2 H) 7.1(m, 1 H) 7.2(d, J=7.3 Hz, 1 H) 7.3(m, 2 H) 7.7(d, J=8.8 Hz, 2 H) 7.9(d, J=8.8 Hz, 2 H) 10.2(s, 1 H) 10.8(s, 1 H). (DMSO-d6) |
| 52 | 8-CH$_3$ | CH$_2$ | 4-phenoxyphenyl | HCl | 162–167 | 3414, 3039, 1710, 1691, 1506, 1487, 1228 | 2.1(d, J=13.0 Hz, 2 H) 2.3(s, 3 H) 2.9(q, J=11.9 Hz, 2 H) 3.2(m, 2 H) 3.6(d, J=11.1 Hz, 2H) 3.8(t, J=11.3 Hz, 1H) 4.0(s, 2H) 5.0(s, 2 H) 6.9(m, 4 H) 7.0(m, 3 H) 7.2(d, J=7.0 Hz, 1 H) 7.3(t, J=8.4 Hz, 2 H) 7.6(d, J=8.9 Hz, 2 H) 10.1(s, 1 H) 10.6(s, 1 H) (DMSO-d6) |
| 53 | 6-Cl | CH$_2$ | 4-acetylphenyl | HCl | 244–286 | 3579, 3475, 2992, 1717, 1667, 1600, 1545, 1263, 1041, 948 | 2.0(d, J=13.7 Hz, 2 H) 2.5(s, 3 H) 2.9(m, 2 H) 3.4(m, 2 H) 3.7(d, J=11.9 Hz, 2 H) 4.2(s, 2 H) 4.3(m, 1 H) 5.1(s, 2 H) 7.4(m, 3 H) 7.7(d, J=8.6 Hz, 2 H) 8.0(d, J=8.6 Hz, 2 H) 10.2(s, 1 H) 11.0(s, 1H). (DMSO-d6) |
| 54 | 8-CH$_3$ | CH$_2$ | 4-acetylphenyl | HCl | >280 | 3422, 2967, 1701, 1676, 1590, 1407, 1256, 950, 835, 773 | 2.1(d, J=14.5 Hz, 2 H) 2.4(s, 3 H) 2.5(s, 3H) 2.9(m, 2 H) 3.3(t, J=13.5 Hz, 2 H) 3.6(d, J=12.3 Hz, 2 H) 3.8(t, J=11.4 Hz, 1 H) 4.1(s, 2H) 5.1(s, 2H) 7.1(m, 2H) 7.2(d, J=7.3 Hz, 1 H) 7.7(d, J=8.8 Hz, 2 H) 7.9(d, J=8.8 Hz, 2 H) 10.2(s, 1 H) 10.9(s, 1 H). (DMSO-d6) |
| 55 | 6-Cl | CH$_2$ | 4-phenoxyphenyl | HCl | 262–267 | 2990, 1714, 1560, 1488, 1231, 1039, 950, 871, 751 | 2.0(d, J=13.2 Hz, 2 H) 2.9(m, 2 H) 3.3(m, 2 H) 3.6(d, 2 H) 4.1(s, 2 H) 4.3(m, 1 H) 5.1(s, 2 H) 7.0(m, 4 H) 7.1(t, J=7.4 Hz, 1 H) 7.3(m, 5 H) 7.6(d, J=9.0 Hz, 2 H) 10.2(s, 1 H) 10.6(s, 1 H) (DMSO-d6) |
| 56 | 8-CH$_3$ | CH$_2$ | 4-phenoxyphenyl | HCl | 217 | 3432, 2894, 1701, 1649, 1597, 1541, 1281, 1033, 925, 857 | 2.1(d, J=13.4 Hz, 2 H) 2.4(s, 3 H) 2.9(m, 2 H) 3.3(m, 2 H) 3.6(d, J=11.4 Hz, 2H) 3.8(m, 1 H) 4.1(s, 2 H) 5.0(s, 2 H) 7.1(m, 2 H) 7.2(d, J=7.5 Hz, 1 H) 7.5(m, 2 H) 7.6(dd, J=6.9, 2.1 Hz, 2 H) 7.7 (dd, J=8.2, 1.3 Hz, 2 H) 7.8(s, 4 H) 10.2(s, 1 H) 10.9 (s, 1 H). (DMSO-d6) |
| 57 | 6-Cl | CH$_2$ | 4-phenoxyphenyl | HCl | 256–259 | 3449, 3051, 1708, 1599, 1541, 1315, 1203, 1041, 949, 702 | 2.0(d, J=13.2 Hz, 2 H) 2.9(m, 2 H) 3.3(m, 2 H) 3.6(d, J=9.9 Hz, 2 H) 4.2(s, 2 H) 4.2(m, 1 H) 5.1(s, 2 H) 7.3(m, 3 H) 7.5(t, J=7.3 Hz, 2 H) 7.6(t, J=7.9 Hz, 1 H) 7.7(m, 4 H) 10.2(s, 1 H) 10.9(s, 1 H). (DMSO-d6) |

| | | | | | | |
|---|---|---|---|---|---|---|
| 58 | 6-CH₃ | CH₂ | H | 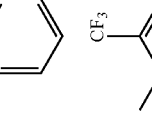 | — | 3177, 3045, 1701, 1595, 1492, 1215, 1046, 966, 808 | 146–148 | 1.9(d, J=13.7 Hz, 2 H) 2.3(s, 3 H) 2.4(m, 2 H) 2.9(m, J=12.4, 4.0 Hz, 2 H) 3.1(m, 2 H) 3.2(s, 2 H) 3.8(m, 1 H) 5.1(s, 2 H) 6.9(m, 2 H) 7.1(d, J=8.4 Hz, 1 H) 7.3(d, 8.8 Hz, 2 H) 7.6(d, J=8.8 Hz, 2 H) 9.2(s, 1 H). (CDCl₃-d) |
| 59 | 6-CH₃ | CH₂ | H |  | — | 169–173 | 3302, 3068, 1730, 1706, 1609, 1508, 1329, 1213, 1067, 846 | 1.9(d, J=11.7 Hz, 2 H) 2.3(s, 3 H) 2.4(m, 2 H) 2.9(qd, J=12.6, 4.1 Hz, 2 H) 3.1(d, J=1.5 Hz, 2 H) 3.2(s, 2 H) 3.8(t, J=12.0 Hz, 1 H) 5.1(s, 2 H) 6.9(m, 2 H) 7.1(d, J=9.0 Hz, 1 H) 7.6(d, J=8.8 Hz, 2 H) 7.8(d, J=9.0 Hz, 2 H) 9.4(s, 1 H). (CDCl₃-d) |
| 60 | 6-CH₃ | CH₂ | H |  | — | 154–157 | 3550, 2799, 1697, 1601, 1522, 1443, 1213, 1047, 817, 764 | 1.9(d, J=11.7 Hz, 2 H) 2.3(s, 3 H) 2.4(t, J=11.2 Hz, 2 H) 2.9(qd, J=12.4, 3.6 Hz, 2 H) 3.1(d, J=11.7 Hz, 2 H) 3.2(s, 2 H) 3.8(tt, J=12.0, 3.7 Hz, 1 H) 5.1(s, 2 H) 6.9(d, J=8.4 Hz, 2 H) 7.0(s, 1 H) 7.1(m, 2 H) 7.4(m, 2 H) 7.6(d, J=7.6 Hz, 2 H) 9.2(s, 1H). (CDCl₃-d) |
| 61 | 8-CH₃ | CH₂ | H |  | HCl | 249–253 | 3449, 2922, 2849, 1695, 1611, 1550, 1257, 1037, 952, 832 | 1.3(m, 4 H) 1.7(m, 6 H) 2.1(d, J=12.1 Hz, 2 H) 2.3(s, 3 H) 2.4(s, 1 H) 2.9(m, 2 H) 3.2(t, J=11.6 Hz, 2H) 3.6(d, J=10.8 Hz, 2 H) 3.8(t, J=10.6 Hz, 1 H) 4.0(s, 2 H) 5.0(s, 2H) 7.0(m, 2 H) 7.1(m, 3 H) 7.4(d, J=8.4 Hz, 2 H) 10.0(br, 1 H) 10.4(s, 1 H). (DMSO-d6) |
| 62 | 6-Cl | CH₂ | H |  | HCl | 249–256 | 2929, 1692, 1607, 1547, 1293, 1201, 1043, 830 | 1.3(m, 4 H) 1.7(m, 6 H) 2.0(d, J=15.7 Hz, 2 H) 2.4(m, 1 H) 2.9 (q, J=12.5 Hz, 2 H) 3.3(t, J=11.9 Hz, 2 H) 3.6(d, J=10.3 Hz, 2 H) 4.1(s, 2 H) 4.2(t, J=12.1 Hz, 1 H) 5.1(s, 2 H) 7.1(d, J=8.6 Hz, 2 H) 7.4(m, 3 H) 7.5(d, J=8.6 Hz, 2 H) 10.1(br, 1 H) 10.5(s, 1 H). (DMSO-d6) |
| 63 | H | CH₂ | H |  | HCl | 211–216 | 3260, 3058, 1681, 1610, 1296, 1036, 954, 772 | 1.9(d, J=13.7 Hz, 2 H) 2.8(m, 2 H) 3.1(m, 2 H) 3.3(d, J=10.6 Hz, 2 H) 3.9(s, 2 H) 4.2(t, J=10.3 Hz, 1 H) 5.1(s, 2 H) 7.1(t, J=7.1 Hz, 1 H) 7.4(m, 8 H) 7.6(m, 2 H) 7.7(d, J=7.1 Hz, 2 H) 10.1(br, 1 H) 10.8(s, 1 H). (DMSO-d6) |

| | | | | | | |
|---|---|---|---|---|---|---|
| 64 | 8-CH₃ | CH₂ | H | ![benzoyl-o-tolyl] | HCl | 168–176 | 3413, 2961, 1686, 1606, 1282, 1033, 951, 775 | 2.0(d, J=13.4 Hz, 2 H) 2.3(s, 3 H) 2.8(m, 2 H) 3.0(m, 2 H) 3.3(d, J=10.8 Hz, 2 H) 3.7(t, J=12.2 Hz, 1 H) 3.8(s, 2 H) 5.0(s, 2H) 7.0 (m, 2 H) 7.2(d, J=17.7 Hz, 1 H) 7.3(t, J=7.5 Hz, 1 H) 7.4(m, 4 H) 7.6(m, 2 H) 7.7(d, J=7.7 Hz, 2 H) 10.0(s, 1 H) 10.7(s, 1 H). (DMSO-d6) |
| 65 | 6-Cl | CH₂ | H | ![benzoyl-o-tolyl] | HCl | 167–178 | 3259, 1686, 1491, 1299, 1205, 1041, 956, 770 | 1.9(d, J=12.8 Hz, 2 H) 2.7(m, 2 H) 3.1(m, 2 H) 3.3(d, J=10.6 Hz, 2 H) 3.9(s, 2 H) 4.2(m, 1 H) 5.1(s, 2 H) 7.4(m, 5 H) 7.5(m, 3 H) 7.6(m, 2 H) 7.7(d, J=8.1 Hz, 2 H) 10.0(s, 1 H) 10.8(s, 1 H). (DMSO-d6) |
| 66 | 6-CH₃ | CH₂ | H | ![benzoyl-o-tolyl] | — | 167–170 | 3448, 2938, 1702, 1634, 1509, 1445, 1156, 1045 | 1.8(d, J=9.3 Hz, 2 H) 2.3(s, 3 H) 2.5(m, 2 H) 2.9(qd, J=12.6, 3.5 Hz, 2 H) 3.0(d, J=11.2 Hz, 2 H) 3.2(s, 2 H) 4.3(tt, J=12.8, 4.6 Hz, 1 H) 5.0(s, 2 H) 7.0(m, 2 H) 7.1(m, 1 H) 7.5(m, 2 H) 7.6(m, 4 H) 7.8(m, 2 H) 8.7(d, J=8.1 Hz, 1 H) 11.9(s, 1 H). (CDCl₃-d) |
| 67 | 6-CH₃ | CH₂ | H | ![phenoxy-tolyl] | HCl | 234–237 | 3148, 2970, 2449, 1691, 1541, 1507, 1233, 1038 | 2.0(d, J=14.1 Hz, 2 H) 2.2(s, 3 H) 2.9(m, 2 H) 3.3(m, 2 H) 3.6(d, J=12.1 Hz, 2 H) 4.1(m, 2 H) 4.2(m, 1 H) 5.1(s, 2 H) 7.0(m, 6 H) 7.2(m, 2 H) 7.3(t, J=7.8 Hz, 2 H) 7.6(d, J=9.0 Hz, 2 H) 10.1(s, 1 H) 10.6(s, 1 H). (DMSO-d6) |
| 68 | 6-CH₃ | CH₂ | H | ![acetyl-tolyl] | HCl | 273–277 | 2927, 1705, 1666, 1594, 1595, 1508, 1267, 1117, 946, 839 | 2.0(d, J=13.2 Hz, 2 H) 2.2(s, 3 H) 2.5(m, 3 H) 2.9(m, 2 H) 3.4(m, 2 H) 3.6(d, J=12.1 Hz, 2 H) 4.2(m, 3 H) 5.1(s, 2 H) 7.1(s, 1 H) 7.2(m, 2 H) 7.7(d, J=8.8 Hz, 2 H) 7.9(d, J=8.8 Hz, 2 H) 10.2(br, 1 H) 10.9(s, 1 H). (DMSO-d6) |

| # | R | X | Structure | Salt | mp (°C) | IR | NMR |
|---|---|---|---|---|---|---|---|
| 69 | H | CH$_2$ | fluorenol with 2-methyl | HCl | 270–273 | 3328, 3071, 2547, 1715, 1691, 1606, 1259, 1045, 775 | 2.0(d, J=11.5 Hz, 2 H) 2.9(m, 2 H) 3.4(m, 2 H) 3.7(d, J=12.3 Hz, 2 H) 4.2(s, 2 H) 4.3(m, 1 H) 5.1(s, 2 H) 5.4(s, 1 H) 7.1(m, 1 H) 7.3(m, 2 H) 7.5(dd, J=8.2, 1.8 Hz, 1 H) 7.6(m, 2 H) 7.6(d, J=7.1 Hz, 1 H) 8.0(d, J=1.6 Hz, 1 H) 10.1(s, 1 H) 10.7(s, 1 H). (DMSO-d6) |
| 70 | 6-Cl | CH$_2$ | fluorenone with 2-methyl | HCl | >300 (Dec) | 2999, 1707, 1603, 1561, 1490, 1463, 1298, 1200 | 2.0(d, J=11.7 Hz, 2 H) 2.8(m, 2 H) 3.1(m, 2 H) 3.5(d, 2 H) 4.3 (m, 3 H) 5.2(s, 2 H) 7.3(m, 1 H) 7.4(m, 3 H) 7.6(m, 2 H) 7.7(m, 3 H) 8.0(s, 1 H) 11.4(s, 1 H). (DMSO-d6) |
| 71 | 6-CH$_3$ | CH$_2$ | fluorenone with 2-methyl | HCl | 281–285 | 2985, 1701, 1604, 1561, 1466, 1300, 1262 | 2.0(d, J=11.7 Hz, 2 H) 2.3(s, 3 H) 2.9(m, 2 H) 3.2(m, 2 H) 3.6(d, 2H) 4.2(s, 2 H) 5.1(s, 2 H) 7.1(s, 1 H) 7.3(m, 3 H) 7.6(m, 2 H) 7.7(m, 3 H) 8.0(s, 1 H) 10.3(s, 1 H) 11.4(s, 1 H). (DMSO-d6) |
| 72 | 8-CH$_3$ | CH$_2$ | fluorenone with 2-methyl | HCl | >300 (dec) | 3448, 1686, 1603, 1561, 1463, 1304, 1276 | 2.0(d, J=11.9 Hz, 2 H) 2.4(s, 3 H) 2.9(m, 2 H) 3.3(m, 2 H) 3.6(d, 2 H) 3.8(m, 1 H) 4.2(s, 2 H) 5.1(s, 2 H) 7.1(s, 2 H) 7.3(m, 3 H) 7.6(m, 2 H) 7.7(m, 3 H) 8.0(s, 1 H) 10.3(s, 1 H) 11.4(s, 1 H). (DMSO-d6) |
| 73 | 6-Cl | CH$_2$ | fluorenol with 2-methyl | HCl | 286–289 | 3423, 3000, 1707, 1603, 1560, 1491, 1460, 1201, 1041 | 2.0(d, J=12.3 Hz, 2 H) 2.9(m, 2 H) 3.3(m, 2 H) 3.7(d, J=11.2 Hz, 2 H) 4.1(m, 2 H) 4.3(m, 1 H) 5.1(s, 2 H) 5.4(s, 1 H) 7.2(t, J=7.3 Hz, 1 H) 7.3(t, J=7.4 Hz, 1 H) 7.4(m, 3 H) 7.5(m, 2 H) 7.7(t, J=8.8 Hz, 2 H) 7.9(s, 1 H) 10.2(s, 1 H) 10.7(s, 1 H). (DMSO-d6) |
| 74 | 6-CH$_3$ | CH$_2$ | fluorenol with 2-methyl | HCl | 196–199 | 3392, 3045, 1695, 1560, 1458, 1295, 1217, 1040 | 2.0(d, J=12.1 Hz, 2 H) 2.3(s, 3 H) 2.9(m, 2 H) 3.4(m, 2 H) 3.7(d, J=11.4 Hz, 2 H) 4.3(m, 2 H) 5.1(s, 2 H) 5.5(s, 1 H) 5.9(br, 1 H) 7.1(s, 1 H) 7.2(d, J=8.4 Hz, 1 H) 7.3(m, 2 H) 7.3(t, J=7.0 Hz, 1 H) 7.6(d, J=7.1 Hz, 1 H) 7.6(d, J=7.9 Hz, 2 H) 7.7(m, 2 H) 8.0(s, 1 H) 10.3(s, 1 H) 11.2(s, 1 H). (DMSO-d6) |

| # | R | X | Ar | Salt | mp (°C) | IR | NMR |
|---|---|---|---|---|---|---|---|
| 75 | 8-CH₃ | CH₂ | 9-hydroxyfluorenyl (with methyl) | HCl | 283–285 | 3260, 1688, 1618, 1563, 1467, 1384, 1309, 1280 | 2.1(d, J=13.5 Hz, 2 H) 2.4(s, 3 H) 2.9(m, 2 H) 3.3(m, 2 H) 3.6(d, J=11.0 Hz, 2 H) 3.8(t, J=11.7 Hz, 1 H) 4.1(s, 2 H) 5.1(s, 2 H) 5.4(s, 1 H) 7.1(m, 2 H) 7.2(td, J=7.4, 1.2 Hz, 2 H) 7.5(d, J=6.8 Hz, 2 H) 7.7(m, 2 H) 7.9(d, J=1.5 Hz, 1 H) 10.1(s, 1 H) 10.7(s, 1 H) (DMSO-d6) |
| 76 | 6-CH₃ | CH₂ | 9-hydroxyfluorenyl (with methyl) | HCl | 238–241 | 3399, 1693, 1618, 1559, 1295, 1217, 1041 | 2.0(d, J=13.2 Hz, 2 H) 2.2(s, 3 H) 2.9(m, 2 H) 3.3(m, 2 H) 3.7(d, J=11.0 Hz, 2 H) 4.1(s, 2 H) 4.2(m, 1 H) 5.0(s, 2 H) 5.4(s, 1 H) 7.0(s, 1 H) 7.1(d, J=8.4 Hz, 1 H) 7.3(m, 3 H) 7.4(d, J=8.2 Hz, 1 H) 7.5(m, 2 H) 7.6(d, J=7.3 Hz, 1 H) 8.0(s, 1 H) 10.1(s, 1 H) 10.7(s, 1 H) (DMSO-d6) |
| 77 | 7-F | CH₂ | 4-cyclohexylphenyl | HCl | 273 | 2922, 1719, 1691, 1609, 1512, 1387, 1200, 1042, 830 | 1.2(m 1 H) 1.4(m, 4 H) 1.7(d, J=11.1 Hz, 1 H) 1.8(m, 4 H) 2.0(d, J=11.6 Hz, 2 H) 2.5(m, 1 H) 2.9(d, J=10.6 Hz, 2 H) 3.4(m, 2 H) 3.6(m, 2 H) 4.2(s, 2 H) 4.3(m, 1 H) 5.2(s, 2 H) 7.0(t, J=8.3 Hz, 1 H) 7.2(d, J=8.1 Hz, 2 H) 7.4(m, 2 H) 7.5(d, J=8.1 Hz, 2 H) 10.2(s, 1 H) 10.9(s, 1H). (DMSO-d6) |
| 78 | 5-F | CH₂ | 9-ethylcarbazolyl | HCl | 266 | 1717, 1693, 1625, 1479, 1306, 1242, 1207, 1067, 781, 749 | 1.3(t, J=7.1 Hz, 3 H) 2.1(d, J=12.1 Hz, 2 H) 2.9(d, J=10.1 Hz, 2 H) 3.4(m, 2 H) 3.7(m, 2 H) 4.2(s, 2 H) 4.4(q, J=7.1 Hz, 2 H) 5.3(s, 2 H) 7.1(t, J=8.6 Hz, 1 H) 7.2(t, J=7.3 Hz, 1 H) 7.3(d, J=8.1 Hz, 1 H) 7.5(m, 2 H) 7.6(m, 3 H) 8.1(d, J=7.6 Hz, 1 H) 8.5(s, 1 H) 10.3(s, 1 H) 11.0(s, 1 H)(DMSO-d6) |
| 79 | 6-OCH₃ | CH₂ | 9-ethylcarbazolyl | HCl | 258 | 2944, 1673, 1503, 1491, 1283, 1229, 1036, 809, 739 | 1.3(t, J=7.1 Hz, 3 H) 2.0(d, J=11.6 Hz, 2 H) 2.9(d, J=10.6 Hz, 2 H) 3.4(m, 2H) 3.7(m, 2H) 3.8(s, 3H) 4.2(s, 2H) 4.3(m, 1 H) 4.4(q, J=6.9 Hz, 2 H) 5.1(s, 2 H) 6.9(m, 2 H) 7.2(t, J=7.7 Hz, 1 H) 7.4(d, J=8.6 Hz, 1 H) 7.5(t, J=7.6 Hz, 1 H) 7.6(m, 3 H) 8.1(d, J=7.6 Hz, 1 H) 8.5(s, 1 H) 10.3(s, 1 H) 11.0(s, 1 H). (DMSO-d6) |
| 80 | 7-CH₃ | CH₂ | 9-ethylcarbazolyl | HCl | 263 | 2973, 1712, 1491, 1385, 1299, 1227, 1037, 806, 737 | 1.3(t, J=6.8 Hz, 3 H) 2.0(d, J=12.6 Hz, 2 H) 2.4(s, 3 H) 3.0(d, J=14.1 Hz, 2 H) 3.5(m, 2 H) 3.7(m, 2 H) 4.2(s, 2 H) 4.3(m, 1 H) 4.4(q, J=6.9 Hz, 2 H) 5.1(s, 2 H) 7.0(d, J=8.1 Hz, 1 H) 7.2(m, 3 H) 7.5(t, J=7.6 Hz, 1 H) 7.6(m, 3 H) 8.1(d, J=8.1 Hz, 1 H) 8.5(s, 1 H) 10.3(s, 1 H) 11.0(s, 1 H). (DMSO-d6) |

| # | R | X | Structure | Salt | MS | IR | NMR |
|---|---|---|---|---|---|---|---|
| 81 | 5-Cl | CH₂ | N-ethylcarbazole (methyl-substituted) | HCl | | 1692, 1589, 1462, 1301, 1229, 1047, 783 | 1.3(t, J=6.8 Hz, 3 H) 2.1(d, J=11.1 Hz, 2 H) 2.9(m, 2 H) 3.4(m, 2 H) 3.7(d, J=11.6 Hz, 2 H) 4.2(s, 2 H) 4.3(m, 1 H) 4.4q, J=6.6 Hz, 2 H) 5.3(s, 2 H) 7.2(t, J=7.3 Hz, 1 H) 7.3(d, J=7.1 Hz, 1 H) 7.5(m, 3 H) 7.6(m, 3 H) 8.1(d, J=7.6 Hz, 1 H) 8.5(s, 1 H) 10.2(s, 1 H) 10.9(s, 1 H). (DMSO-d6) |
| 82 | 5-F | CH₂ | phenoxyphenyl (methyl-substituted) | HCl | 234 | 2989, 1719, 1624, 1507, 1488, 1229, 1071, 779 | 2.0(d, J=12.6 Hz, 2 H) 2.9(d, J=11.1 Hz, 2 H) 3.4(m, 2 H) 3.6(m, 2H) 4.2(s, 2 H) 4.3(t, J=11.6 Hz, 1 H) 5.3(s, 2 H) 7.0(d, J=8.1 Hz, 2 H) 7.0(m, 3 H) 7.1(t, J=7.3 Hz, 1 H) 7.3(d, J=8.6 Hz, 1 H) 7.4(t, J=8.1 Hz, 2 H) 7.5(m, 1 H) 7.7(d, J=9.1 Hz, 2 H) 10.3(s, 1 H) 11.1(s, 1 H). (DMSO-d6) |
| 83 | 6-OCH₃ | CH₂ | fluorenone (methyl-substituted) | — | 237 | 3293, 1701, 1507, 1465, 1294, 1218, 1040 | 1.9(d, J=12.1 Hz, 2 H) 2.5(t, J=11.6 Hz, 2 H) 2.9(m, 2 H) 3.1(d, J=11.6 Hz, 2 H) 3.2(s, 2 H) 3.8(m, 4 H) 5.1(s, 2 H) 6.7 (d, J=2.0 Hz, 1 H) 6.9(m, 1 H) 7.0(m, 1 H) 7.3(t, J=7.6 Hz, 1 H) 7.4(d, J=8.1 Hz, 1 H) 7.5(t, J=7.6 Hz, 1 H) 7.6(m, 3 H) 8.0(s, 1 H) 9.5(s, 1 H) (CDCl₃-d) |
| 84 | 8-OCH₃ | CH₂ | dibenzofuran (methyl-substituted) | — | 223 | 1718, 1483, 1286, 1223, 1191, 1079, 1037 | 2.0(d, J=11.6 Hz, 2 H) 2.4(t, J=10.9 Hz, 2 H) 2.9(qd, J=12.3, 4.0 Hz, 2H) 3.1(d, J=11.6 Hz, 2 H) 3.2(s, 2H) 3.8(m, 1 H) 3.9(s, 3 H) 5.0(s, 2 H) 6.9(d, J=7.1 Hz, 1 H) 7.1(m, 1 H) 7.3(t, J=7.6 Hz, 1 H) 7.5(t, J=7.6 Hz, 1 H) 7.6(m, 3 H) 8.0(d, J=7.1 Hz, 1 H) 8.4(d, J=2.0 Hz, 1 H) 9.4(s, 1 H) (CDCl₃-d) |
| 85 | 7-Cl | CH₂ | dibenzofuran (methyl-substituted) | — | 88 | 3270, 1719, 1676, 1604, 1508, 1483, 1195, 1048, 749 | 1.9(d, J=12.1 Hz, 2 H) 2.5(t, J=11.1 Hz, 2 H) 2.9(qd, J=12.5, 4.0 Hz, 2H) 3.1(d, J=11.6 Hz, 2 H) 3.2 (s, 2H) 3.8(m, 1 H) 5.1(s, 2 H) 7.1(t, J=7.1 Hz, 1 H) 7.3(t, J=7.8 Hz, 1 H) 7.5(t, J=7.8 Hz, 1 H) 7.6(m, 3 H) 8.0(d, J=7.1 Hz, 1 H) 8.4(d, J=2.0 Hz, 1 H) 9.3(s, 1 H) (CDCl₃-d) |
| 86 | 6-F | CH₂ | fluorenone (methyl-substituted) | — | 237 | 3270, 1706, 1509, 1271, 1206, 1109, 1042, 764 | 1.9(d, J=12.1 Hz, 2 H) 2.5(t, J=11.6 Hz, 2 H) 2.9(m, 2 H) 3.1(d, J=11.6 Hz, 2H) 3.2(s, 2 H) 3.8(t, J=11.9 Hz, 1 H) 5.1(s, 2 H) 6.9 (d, J=6.6 Hz, 2 H) 7.0(m, 1 H) 7.1(t, J=7.1 Hz, 1 H) 7.3(t, J= 7.3 Hz, 1 H) 7.4(d, J=7.6 Hz, 1 H) 7.5(t, J=7.3 Hz, 1 H) 7.6(d, J= 7.6 Hz, 1 H) 7.6(m, 2 H) 8.0(s, 1 H) 9.4 (s, 1 H) (CDCl₃-d) |
| 87 | 7-F | CH₂ | fluorenyl-OH (methyl-substituted) | — | 136 | 3399, 1719, 1618, 1509, 1199, 1042, 769 | 1.9(d, J=12.1 Hz, 2 H) 2.4(t, J=11.9 Hz, 2 H) 2.9(m, 2 H) 3.1(m, 2H) 3.2(s, 2 H) 3.8(qd, J=12.1, 3.8 Hz, 1 H) 5.1(s, 2 H) 5.6(s, 1 H) 6.8(m, 2 H) 7.1(m, 1 H) 7.3(t, J=6.8 Hz, 2 H) 7.4(s, 2 H) 7.6 (m, 3 H) 8.0(d, J=2.0 Hz, 1 H) 9.2(s, 1 H). (CDCl₃-d) |

| # | R | X | Ar | — | Yield | IR | NMR |
|---|---|---|---|---|---|---|---|
| 88 | 5-CH₃ | CH₂ | carbazole (N-H) | — | 213 | 3247, 1701, 1476, 1245, 1204, 1033, 730 | 1.9(d, J=11.6 Hz, 2 H) 2.3(s, 3 H) 2.4(t, J=11.4 Hz, 2 H) 2.9(qd, J=12.3, 4.0 Hz, 2 H) 3.1(d, J=11.6 Hz, 2 H) 3.2(s, 2 H) 3.8(ddd, J=11.9, 8.1, 3.8 Hz, 1 H) 5.1(s, 2H) 6.9(t, J=7.8 Hz, 2H) 7.2(m, 2H) 7.4(m, 3 H) 7.5(dd, J=8.6, 2.0 Hz, 1 H) 8.1(d, J=7.6 Hz, 1 H) 8.3(s, 1 H) 8.4(s, 1 H) 9.2(s, 1 H). (CDCl₃-d) |
| 89 | 5-F | CH₂ | carbazole (N-H) | — | 195 | 3278, 1718, 1654, 1624, 1479, 1242, 1204, 1067, 772 | 1.9(d, J=13.6 Hz, 2 H) 2.4(m, 2 H) 2.9(qd, J=12.3, 3.5 Hz, 2 H) 3.2(d, J=11.6 Hz, 2 H) 3.2(s, 2 H) 3.9(m, 1 H) 5.2(s, 2 H) 6.9(d, J=9.1 Hz, 2 H) 7.2(ddd, J=8.0, 5.2, 3.0 Hz, 1 H) 7.3(m, 1 H) 7.4(m, 3 H) 7.5(dd, J=8.8, 2.3 Hz, 1 H) 8.1(d, J=7.6 Hz, 1 H) 8.1(s, 1 H) 8.4(s, 1 H) 9.2(s, 1 H). (CDCl₃-d) |
| 90 | 6-OCH₃ | CH₂ | carbazole (N-H) | — | 135 | 3293, 1701, 1502, 1289, 1215, 1042, 805, 746, 726 | 1.9(d, J=10.6 Hz, 2 H) 2.4(t, J=11.1 Hz, 2 H) 2.9(qd, J=12.5, 3.5 Hz, 2 H) 3.1(d, J=11.6 Hz, 2 H) 3.2(s, 2 H) 3.8(s, 3 H) 3.8(m, 1 H) 5.1(s, 2 H) 6.7(d, J=2.5 Hz, 1 H) 6.9(m, 1 H) 7.0(d, J=9.1 Hz, 1 H) 7.2(ddd, J=7.8, 5.6, 2.3 Hz, 1 H) 7.4(m, 3 H) 7.5(dd, J=8.6, 2.0 Hz, 1 H) 8.1(d, J=8.1 Hz, 1 H) 8.3(s, 1 H) 8.4(d, J=2.0 Hz, 1 H) 9.2(s, 1 H). (CDCl₃-d) |
| 91 | — | CH₂ | carbazole (N-CH₂CH₃) | — | 100 | 2920, 1719, 1676, 1604, 1478, 1257, 1086, 772, 749 | 1.4(t, J=7.1 Hz, 3 H) 1.9(d, J=12.1 Hz, 2 H) 2.4(t, J=11.4 Hz, 2 H) 2.9(m, 2 H) 3.2(d, J=11.6 Hz, 2 H) 3.2(s, 2 H) 3.9(m, 4 H) 4.4(q, J=7.1 Hz, 2 H) 5.2(s, 2 H) 6.7(d, J=8.6 Hz, 1 H) 7.2(t, J=7.3 Hz, 1 H) 7.3(t, J=8.3 Hz, 1 H) 7.4(m, 2 H) 7.5(m,1 H), 7.6(dd, J=7.3 Hz, 1 H) 8.1(d, J=8.1 Hz, 1 H) 8.4 (d, J=2.0 Hz, 1 H) 9.2(s, 1 H). (CDCl₃-d) |
| 92 | 5-OCH₃ | CH₂ | phenoxyphenyl | — | 73 | 2943, 1719, 1605, 1509, 1478, 1257, 1082, 772 | 1.9(d, J=11.6 Hz, 2 H) 2.4(m, 2 H) 2.9(m, 2 H) 3.1(d, J=11.1 Hz, 2 H) 3.2(m, 2 H) 3.8(m, 1 H) 3.9(m, 3 H) 5.2 (m, 2 H) 6.7 (m, 2 H) 7.0(m, 4 H) 7.1(m, 1 H) 7.3(m, 3 H) 7.6(m, 2 H) 9.1(s, 1 H). (CDCl₃-d) |
| 93 | 7-CH₃ | CH₂ | fluorenyl (OH) | — | 136 | 3406, 2935, 1686, 1500, 1459, 1289, 1215, 1043 | 1.9(d, J=11.1 Hz, 2 H) 2.4(m, 2 H) 2.9(qd, J=12.4, 3.8 Hz, 2 H) 3.1(d, J=11.6 Hz, 2 H) 3.2(s, 2 H) 3.8(m, 4 H) 5.1(s, 2 H) 5.3(s, 1 H) 6.7(d, J=2.5 Hz, 1 H) 6.9(m, 1 H) 7.0(d, J=8.6, 2.0 Hz, 1 H) 7.2(m, 1 H) 7.4(m, 3 H) 7.5(dd, J=8.6, 2.0 Hz, 1 H) 8.1(d, J=7.6 Hz, 1 H) 8.3(s, 1 H) 8.4(d, J=2.0 Hz, 1 H) 9.2(s, 1 H). (CDCl₃-d) |

| # | | | Structure | mp | IR | NMR |
|---|---|---|---|---|---|---|
| 94 | 8-OCH₃ | CH₂ | 3-methyl-9H-fluoren-9-ol | — | 3422, 1701, 1522, 1491, 1286, 1225, 1036, 768, 737 | 2.0(d, J=9.6 Hz, 2 H) 2.3(t, J=11.9 Hz, 2 H) 2.8(m, 2 H) 3.1(d, J=11.1 Hz, 2 H) 3.1(s, 2 H) 3.8(m, 1 H) 3.9(s, 3 H) 5.0 (s, 2 H) 5.6(s, 1 H) 6.8(d, J=7.1 Hz, 1 H) 6.9(d, J=8.1 Hz, 1 H) 7.1(t, J=7.8 Hz, 1 H) 7.4(m, 2 H) 7.5(dd, J=8.1, 2.0 Hz, 1 H) 7.6(m, 2H) 7.7 (d, J=7.6 Hz, 1 H) 8.0(s, 1 H) 9.3(s, 1 H). (CDCl₃-d) |
| 95 | 5-CH₃ | CH₂ | dibenzofuran-methyl | — | 3330, 1719, 1685, 1526, 1482, 1193, 1041, 773 | 1.9(d, J=12.1 Hz, 2 H) 2.3(s, 3 H) 2.4(m, 2 H) 3.0(qd, J=12.5, 3.5 Hz, 2 H) 3.1(d, J=11.6 Hz, 2 H) 3.2(s, 2 H) 3.8(qd, J=12.1, 3.8 Hz, 1 H) 5.1(s, 2 H) 6.9(m, 2 H) 7.3(m, 1 H) 7.3(t, J=7.1 Hz, 1 H) 7.5(t, J=7.8 Hz, 1 H) 7.6(m, 3 H) 8.0.d. J=7.6 Hz, 1 H) 8.4(d, J=2.0 Hz, 1 H) 9.3(s, 1 H). (CDCl₃-d) |
| 96 | 7-CH₃ | CH₂ | N-ethyl-4-methyl-N-phenylaniline | — | 1718, 1686, 1520, 1492, 1383, 1309, 1247, 1210, 1044 | 1.2(t, J=7.1 Hz, 3 H) 1.9(d, J=10.6 Hz, 2 H) 2.4(m, 5 H) 2.9(qd, J=12.5, 4.0 Hz, 2 H) 3.1(d, J=11.6 Hz, 2 H) 3.2(s, 2 H) 3.8(q, J=7.1 Hz, 2 H) 3.8(m, 1 H) 5.1(s, 2 H) 6.9(m, 5 H) 7.0(m, 3 H) 7.2(m, 2 H) 7.5(d, J=8.6 Hz, 2 H) 9.1(s, 1 H). |
| 97 | 8-Cl | CH₂ | 3-methyl-9H-carbazole | — | 3289, 1735, 1663, 1527, 1494, 1460, 1225, 1183, 1041 | 2.1(s, 2 H) 2.4(t, J=10.9 Hz, 2 H) 2.9(qd, J=12.4, 3.8 Hz, 2 H) 3.1 (d, J=11.6 Hz, 2 H) 3.2(s, 2 H) 3.9(tq, J=11.7, 3.8 Hz, 1 H) 5.0(s, 2 H) 7.1(m, 2 H) 7.2(m, 1 H) 7.4(m, 4 H) 7.6(dd, J=8.6, 2.0 Hz, 1 H) 8.1(s, 1 H) 8.4(d, J=7.6 Hz, 1 H) 8.4(d, J=2.0 Hz, 1 H) 9.3 (s, 1H). (CDCl₃-d) |
| 98 | 8-OCH₃ | CH₂ | N-ethyl-4-methyl-N-phenylaniline | — | 3422, 2980, 1701, 1608, 1510, 1492, 1388, 1287, 1252, 1088, 1029 | 1.2(t, J=7.1 Hz, 3 H) 2.2(d, J=12.1 Hz, 2 H) 2.9(m, 2 H) 3.3(m, 2 H) 3.7(d, J=11.1 Hz, 2 H) 3.8(q, J=7.1 Hz, 2 H) 4.0(s, 3 H) 4.1 (m, 1 H) 4.2(s, 2 H) 5.2(s, 2 H) 6.9(m, 4 H) 7.1(d, J=8.6 Hz, 2 H) 7.2(m, 2 H) 7.3(m, 2 H) 7.6(d, J=8.6 Hz, 2 H) 10.2(s, 1 H) 11.0(s, 1 H). (CDCl₃-d) |
| 99 | H | CH₂ | 1-methyl-9H-fluoren-9-ol | 209–210 | 3356, 1715, 1686, 1608, 1498, 1467, 1389, 1291, 1204, 1043, 738 | 2.0(d, J=9.7 Hz, 2 H) 2.5(t, J=12.3 Hz, 2 H) 3.0(m, 2 H) 3.2 (d, J=11.0 Hz, 2 H) 3.3(s, 2 H) 3.9(m, 1 H) 5.1(s, 2 H) 5.6 (d, J=9.7 Hz, 1 H) 7.1(m, 2 H) 7.2(d, J=8.1 Hz, 1 H) 7.4(m, H) 7.7(d, J=7.3 Hz, 1 H) 7.8(t, J=7.8 Hz, 1 H) 8.0(d, J=7.3 Hz, 1 H) 8.3(d, J=8.4 Hz, 1 H) 9.7(s, 1 H) |

| 100 | H | CH$_2$ | | | 2.0(d, J=13.4 Hz, 2 H) 2.9(m, 2 H) 3.4(m, 2 H) 3.6(d, J=11.2 Hz, 2 H) 4.1(s, 2 H) 4.3(m, 1 H) 5.1(s, 2 H) 5.7(s, 1 H) 7.1(m, 1 H) 7.2(m, 2H) 7.3(m, 4H) 7.5(m, 1 H) 7.6(m, 1 H) |
|---|---|---|---|---|---|
| | | | | 240–249 | 3292, 3041 2638, 1700, 1397, 1204, 1041, 745 |
| | | | | | 10.1(s, 1 H) 10.6(s, 1 H) |

N-[4-Chloro-2-(2-chloro-benzoyl)-phenyl]-2-[4-(6-methyl-2-oxo-4H-benzo[d][1,3]oxazin-1-yl)-piperidin-1-yl]-acetamide.

Ex. 101

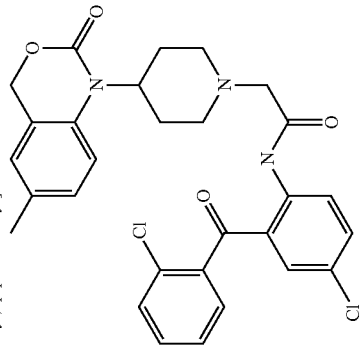

1H-NMR
1.8 (d, J=11.9 Hz, 2 H) 2.1 (s, 3 H) 2.5 (t, J=11.8 Hz, 2 H) 2.8 (m, 2 H) 3.1 (d, J=11.0 Hz, 2 H) 3.3 (s, 2 H) 4.4 (t, J=12.6 Hz, 1 H) 5.0 (s, 2 H) 6.4 (d, J=8.4 Hz, 1 H) 6.9 (s, 1 H) 7.5 (m, 6 H) 7.6 (d, J=8.2 Hz, 1 H) 8.9 (d, J=8.8 Hz, 1 H) 12.7(s, 1 H) (CDCl$_3$-d)
IR (KBr)
1705, 1648, 1561, 1500, 1284, 1220, 1093, 1041, 961, 821, 753
M.P.: 228–232° C.

N-[4-Chloro-2-(2-chloro-benzoyl)-phenyl]-2-[4-(2-oxo-4H-benzo[d][1,3]oxazin-1-yl)-piperidin-1-yl]-acetamide hydrochloride.

Ex. 102

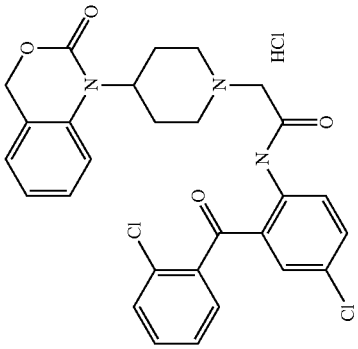

1H-NMR
2.0 (d, J=13.7 Hz, 2 H) 2.9 (m, 2 H) 3.3 (m, 2 H) 3.5 (m, 2 H) 4.1 (s, 2 H) 4.2 (m, 1 H) 5.1 (s, 2H) 7.1 (s, 1 H) 7.2 (d, J=7.0 Hz, 1 H) 7.3 (s, 3H) 7.5 (m, 1H) 7.6 (m, 3 H) 7.7 (d, J=8.2 Hz, 1 H) 7.8 (m, 1 H) 10.2 (s, 1 H) 11.0 (s, 1 H) (DMSO-D6)
IR (KBr)
3386, 1702, 1686, 1523, 1288, 1238, 1041, 960, 761
M.P.: 175–184° C.

N-[4-Chloro-2-(2-chloro-benzoyl)-phenyl]-2-[4-(8-methyl-2-oxo-4H-benzo[d][1,3]oxazin-1-yl)-piperidin-1-yl]-acetamide hydrochloride.

| | |
|---|---|
| Ex. 103 | 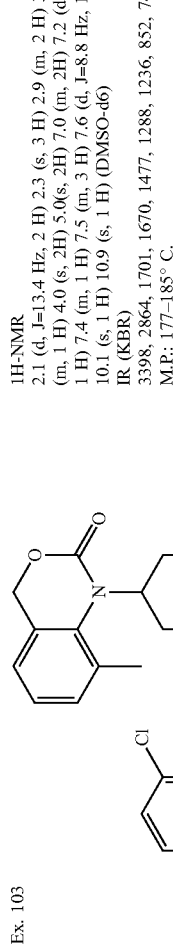<br>N-[4-Chloro-2-(2-chloro-benzoyl)-phenyl]-2-[4-(6-chloro-2-oxo-4H-benzo[d][1,3]oxazin-1-yl)-piperidin-1-yl]-acetamide hydrochloride. | 1H-NMR 2.1 (d, J=13.4 Hz, 2 H) 2.3 (s, 3 H) 2.9 (m, 2 H) 3.2 (m, 2 H) 3.5 (m, 2 H) 3.8 (m, 1 H) 4.0 (s, 2H) 5.0(s, 2H) 7.0 (m, 2H) 7.2 (d, J=7.5 Hz, 1 H) 7.3 (s, 1 H) 7.4 (m, 1 H) 7.5 (m, 3 H) 7.6 (d, J=8.8 Hz, 1 H) 7.8 (d, J=8.4 Hz, 1 H) 10.1 (s, 1 H) 10.9 (s, 1 H) (DMSO-d6)<br>IR (KBR)<br>3398, 2864, 1701, 1670, 1477, 1288, 1236, 852, 748<br>M.P.: 177–185° C. |
| Ex. 104 | 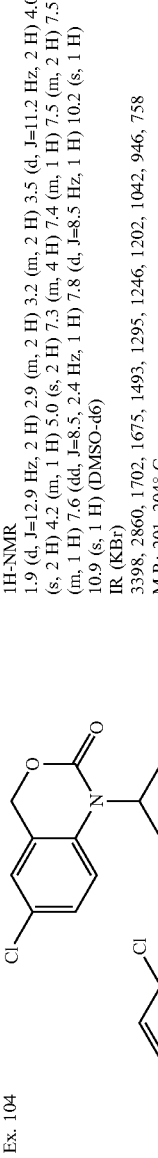<br>2-[4-(7-Methyl-2-oxo-4H-benzo[d][1,3]oxazin-1-yl)-piperidin-1-yl]-N-thiazol-2-yl-acetamide. | 1H-NMR 1.9 (d, J=12.9 Hz, 2 H) 2.9 (m, 2 H) 3.2 (m, 2 H) 3.5 (d, J=11.2 Hz, 2 H) 4.0 (s, 2 H) 4.2 (m, 1 H) 5.0 (s, 2 H) 7.3 (m, 4 H) 7.4 (m, 1 H) 7.5 (m, 2 H) 7.5 (m, 1 H) 7.6 (dd, J=8.5, 2.4 Hz, 1 H) 7.8 (d, J=8.5 Hz, 1 H) 10.2 (s, 1 H) 10.9 (s, 1 H) (DMSO-d6)<br>IR (KBr)<br>3398, 2860, 1702, 1675, 1493, 1295, 1246, 1202, 1042, 946, 758<br>M.P.: 201–204° C. |

-continued
| | | |
|---|---|---|
| Ex. 105 | 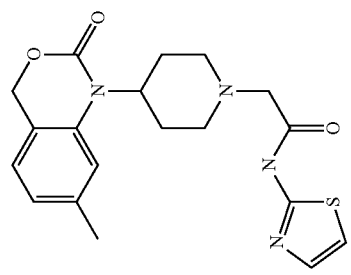 | 1H-NMR 1.9 (d, J=12.6 Hz, 2 H) 2.4 (s, 3 H) 2.5 (m, 2 H) 2.9 (m, J=12.5, 4.0 Hz, 2 H) 3.1 (d, J=11.6 Hz, 2 H) 3.3 (s, 2 H) 3.9 (m, 1 H) 5.0 (s, 2 H) 6.9 (s, 1 H) 6.9 (d, J=7.6 Hz, 1 H) 7.0 (d, J=3.5 Hz, 1 H) 7.0 (d, J=7.6 Hz, 1 H) 7.5 (d, J=3.5 Hz, 1 H) 10.4 (s, 1 H) (CDCl$_3$-d) IR (KBr) 2920, 1718, 1618, 1528, 1458, 1383, 1294, 1208, 1143, 1045 M.P.: 193° C. |
| | 2-[4-(6-Fluoro-2-oxo-4H-benzo[d][1,3]oxazin-1-yl)-piperidin-1-yl]-N-thiazol-2-yl-acetamide. | |
| Ex. 106 | 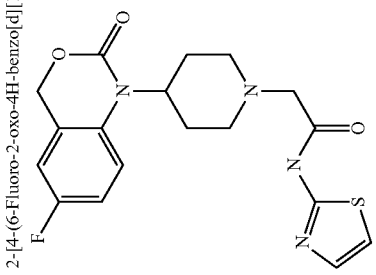 | 1H-NMR 1.9 (d, J=13.6 Hz, 2 H) 2.5 (td, J=12.1, 2.0 Hz, 2 H) 2.8 (qd, J=12.6, 3.8 Hz, 2 H) 3.1(d, J=11.6 Hz, 2 H) 3.3 (s, 2 H) 3.9 (m, 1 H) 5.1 (s, 2 H) 6.9 (d, J=7.1 Hz, 1 H) 7.0 (d, J=3.5 Hz, 1 H) 7.1 (m, 2 H) 7.5 (d, J=3.5 Hz, 1 H) 10.3 (s, 1 H) (CDCl$_3$-d) IR (KBr) 2935, 1701, 1528, 1500, 1458, 1271, 1207, 1145, 1045, 730 M.P.: 67° C. |
| | N-Dibenzothiophen-2-yl-2-[4-(5-methoxy-2-oxo-4H-benzo[d][1,3]oxazin-1-yl)-piperidin-1-yl]-acetamide. | |

-continued
| Ex. 107 | 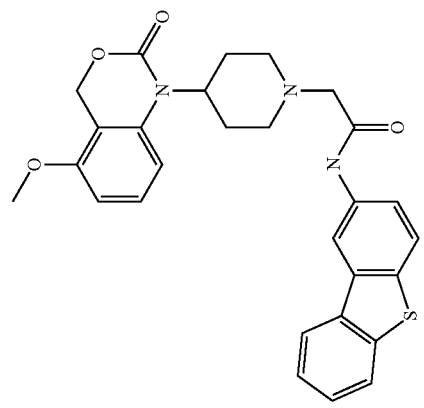 2-[4-(7-Chloro-2-oxo-4H-benzo[d][1,3]oxazin-1-yl)-piperidin-1-yl]-N-dibenzothiophen-2-yl-acetamide. | 1H-NMR 1.9 (d, J=12.1 Hz, 2 H) 2.4 (m, 2 H) 3.0 (m, 2 H) 3.1 (d, J=11.6 Hz, 2 H) 3.2 (s, 2 H) 3.8(m, 4 H) 5.2 (s, 2 H) 6.7 (t, J=8.3 Hz, 2 H) 7.3 (t, J=8.3 Hz, 1 H) 7.5 (m, 2 H) 7.6 (dd, J=8.6, 2.0 Hz, 1 H) 7.8 (m, 2 H) 8.2 (m, 1 H) 8.6 (d, J=2.0 Hz, 1 H) 9.3 (s, 1 H) (CDCl$_3$-d) IR (KBr) 2935, 1719, 1605, 1509, 1477, 1257, 1141, 1084, 766, 733 M.P.: 210° C. |
| --- | --- | --- |
| Ex. 108 | 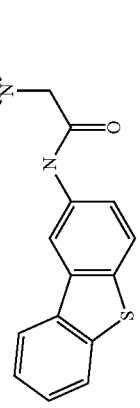 2-[4-(5-Hydroxy-2-oxo-4H-benzo[d][1,3]oxazin-1-yl)-piperidin-1-yl]-N-(4-phenoxy-phenyl)-acetamide. | 1H-NMR 1.9 (d, J=11.1 Hz, 2 H) 2.5 (t, J=11.1 Hz, 2 H) 2.9 (qd, J=12.4, 3.8 Hz, 2 H) 3.1 (d, J=11.6 Hz, 2 H) 3.2 (s, 2 H) 3.8 (ddd, J=12.1, 8.1, 4.0 Hz, 1 H) 5.1 (s, 2 H) 7.1 (m, 3 H) 7.5(dd, J=6.1, 3.0 Hz, 2 H) 7.6 (d, J=8.6 Hz, 1 H) 7.8 (m, 2 H) 8.2(dd, J=5.8, 3.3 Hz, 1 H) 8.6(s, 1 H) 9.3(s, 1 H) (CDCl$_3$-d) IR (KBr) 3300, 1718, 1682, 1509, 1472, 1431, 1293, 1199, 1043, 806, 760, 726 M.P.: 236° C. |

| | -continued |
|---|---|
| Ex. 109 | 2.1 (m, 2 H) 3.0 (d, J=12.1 Hz, 2 H) 3.5 (m, 2 H) 3.7(d, J=10.1 Hz, 2 H) 4.2 (s, 2H) 4.3 (m, 1 H) 5.2 (s, 2H) 6.7 (d, J=8.1 Hz, 1 H) 6.9 (m, 1H) 7.1 (d, J=8.6 Hz, 2 H) 7.1(d, J=9.1 Hz, 2 H) 7.2 (m, 2 H) 7.5 (t, J=8.1 Hz, 2 H) 7.7(d, J=8.6 Hz, 2 H) 10.2 (s, 1 H) 10.9 (s, 1 H) (DMSO-d6)<br>IR (KBr)<br>3192, 1701, 1609, 1560, 1508, 1476, 1229, 1071, 954, 779, 696<br>M.P.: 256° C.<br>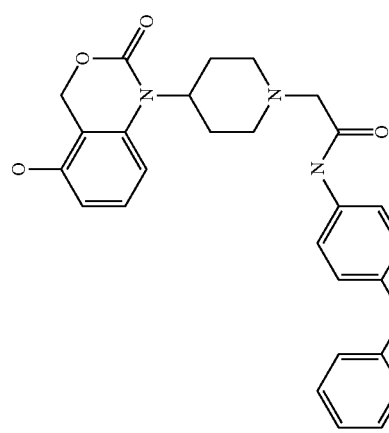<br>1-{1-[2-(3,4-Dihydro-1H-isoquinolin-2-yl)-2-oxo-ethyl]-piperidin-4-yl}-1,4-dihydro-benzo[d][1,3]oxazin-2-one hydrochloride. |
| Ex. 110 | 1H-NMR<br>2.0 (d, J=12.7 Hz, 2 H) 2.8 (t, J=6.0 Hz, 1 H) 2.9 (m, 3 H) 3.3 (m, 2 H) 3.6 (m, 3 H) 3.7 (t, J=6.0 Hz, 1 H) 4.3 (m, 1 H) 4.4 (s, 2 H) 4.6 (m, 2 H) 5.2 (s, 2 H) 7.1 (t, J=7.4 Hz, 1 H) 7.2 (m, 4 H) 7.3 (d, J=7.1 Hz, 1 H) 7.4 (m, 2H) 10.0 (s, 1 H) (DMSO-d6)<br>IR (KBr)<br>3048, 2878, 1687, 1658, 1606, 1464, 1397, 1043, 771<br>M.P.: 226–230° C.<br>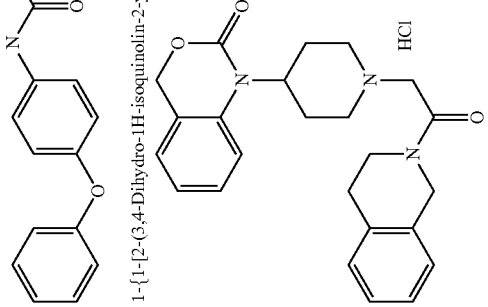<br>2-[4-(6-Fluoro-2-oxo-4H-benzo[d][1,3]oxazin-1-yl)-piperidin-1-yl)-N-quinolin-6-yl-acetamide. |

| Ex. 111 | 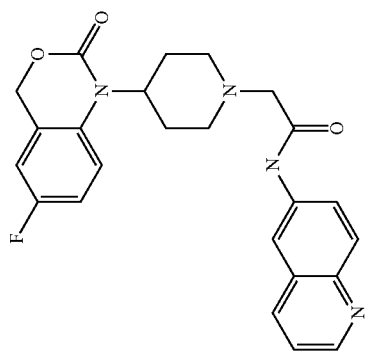 | 1H-NMR 1.9 (d, J=12.1 Hz, 2 H) 2.5 (t, J=11.1 Hz, 2 H) 2.9 (qd, J=12.5, 4.0 Hz, 2 H) 3.1 (d, J=11.6 Hz, 2 H) 3.3 (s, 2H) 3.8 (m, 1 H) 5.1 (s, 2 H) 6.9 (dd, J=7.6, 2.5 Hz, 1 H) 7.0 (m, 2 H) 7.4 (dd, J=8.1, 4.0 Hz, 1 H) 7.8 (dd, J= 8.8, 2.3 Hz, 1 H) 8.1 (d, J=9.1 Hz, 1 H) 8.1 (d, J=8.6 Hz, 1 H) 8.3 (d, J=2.0 Hz, 1 H) 8.8 (m, 1 H) 9.4 (s, 1 H). (CDCl$_3$-d) IR (KBr) 1701, 1500, 1458, 1272, 1205, 1044, 768 M.P.: 84° C. |
|---|---|---|
| | 2-[4-(6-Methoxy-2-oxo-4H-benzo[d][1,3]oxazin-1-yl)-piperidin-1-yl]-N-quinolin-6-yl-acetamide. | |
| Ex. 112 | | 1H-NMR 1.9 (d, J=12.1 Hz, 2 H) 2.5 (m, 2 H) 2.9 (qd, J=12.5, 4.0 Hz, 2 H) 3.1 (d, J=11.6 Hz, 2 H) 3.2 (s, 2 H) 3.8 (m, 4H) 5.1 (s, 2 H) 6.7 (d, J=2.5 Hz, 1 H) 6.9 (m, 1 H) 7.0 (d, J=9.1 Hz, 1 H) 7.4 (dd, J=8.3, 4.3 Hz, 1 H) 7.8 (dd, J=9.1, 2.0 Hz, 1 H) 8.1 (d, J=9.1 Hz, 1 H) 8.1 (d, J=7.6 Hz, 1 H) 8.4 (d, J=2.5 Hz, 1 H) 8.8 (m, 1 H) 9.4 (s, 1 H). (CDCl$_3$-d) IR (KBr) 3385, 1701, 1560, 1501, 1459, 1278, 1215, 1042 M.P.: 73° C. |
| | 2-[4-(6-Chloro-2-oxo-4H-benzo[d][1,3]oxazin-1-yl)-piperidin-1-yl]-N-quinolin-6-yl-acetamide | |

| | | |
|---|---|---|
| Ex. 113 | [structure: 6-chloro-2-oxo-4H-benzo[d][1,3]oxazin-1-yl piperidine connected via acetamide to quinolin-6-yl] | 1H-NMR 1.9 (d, J=10.1 Hz, 2 H) 2.5 (m, 2 H) 2.9 (qd, J=12.5, 4.0 Hz, 2 H) 3.1 (d, J=11.6 Hz, 2H) 3.3 (s, 2H) 3.8 (m, 1 H) 5.1 (s, 2H) 7.1 (s, 1 H) 7.1 (m, 2 H) 7.4 (dd, J=8.6, 4.0 Hz, 1 H) 7.8 (dd, J=9.1, 2.5 Hz, 1 H) 8.1 (d, J=9.1 Hz, 1 H) 8.2 (d, J=8.1 Hz, 1 H) 8.4 (d, J=2.5 Hz, 1 H) 8.8 (d, J=2.5 Hz, 1 H) 9.4 (s, 1 H). (CDClhd 3-d) IR (KBr) 3410, 1718, 1604, 1527, 1497, 1379, 1199, 1043 M.P.: 87° C. |
| | 2-[4-(6-Fluoro-2-oxo-4H-benzo[d][1,3]oxazin-1-yl]-piperidin-1-yl]-N-(2-methyl-benzothiazol-5-yl)-acetamide | |
| Ex. 114 | [structure: 6-fluoro-2-oxo-4H-benzo[d][1,3]oxazin-1-yl piperidine connected via acetamide to 2-methyl-benzothiazol-5-yl] | 1H-NMR 1.9 (dd, J=12.4, 1.8 Hz, 2 H) 2.4 (td, J=12.1, 2.0 Hz, 2 H) 2.8 (s, 3 H) 2.9 (m, 2 H) 3.1 (d, J=12.1 Hz, 2 H) 3.2 (s, 2 H) 3.8 (qd, J=12.1, 3.8 Hz, 1 H) 5.1 (s, 2 H) 6.9 (dd, J=7.6, 2.5 Hz, 1 H) 7.0 (m, 2 H) 7.5 (dd, J=8.6, 2.0 Hz, 1 H) 7.8 (d, J=8.6 Hz, 1 H) 8.3 (d, J=2.0 Hz, 1 H) 9.3 (s, 1 H). (CDCl$_3$-d) IR (KBr) 1701, 1501, 1459, 1271, 1206, 1045 M.P.: 99° C. |
| | 2-[4-(6-Chloro-2-oxo-4H-benzo[d][1,3]oxazin-1-yl)-piperidin-1-yl]-N-(2-methyl-benzothiazol-5-yl)-acetamide. | |

-continued

| Ex. 115 | 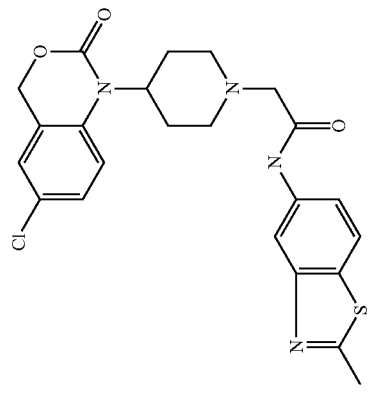 2-[4-(6-Methoxy-2-oxo-4H-benzo[d][1,3]oxazin-1-yl]-N-(2-methyl-benzothiazol-5-yl)-acetamide | 1H-NMR<br>1.9 (d, J=11.6 Hz, 2 H) 2.5 (td, J=12.1, 2.5 Hz, 2 H) 2.8 (s, 3 H) 2.9 (qd, J=12.5, 4.0 Hz, 2 H) 3.1 (d, J=11.6 Hz, 2 H) 3.2 (s, 2 H) 3.8 (m, 1 H) 5.1 (s, 2 H) 7.0 (s, 1 H) 7.1 (m, 2 H) 7.5 (dd, J=8.6, 2.0 Hz, 1 H) 7.8 (d, J=8.6 Hz, 1 H) 8.4 (s, 1 H) 9.3 (s, 1 H). (CDCl₃-d)<br>IR (KBr)<br>1718, 1605, 1509, 1465, 1379, 1292, 1200, 1043<br>M.P.: 97° C. |
| --- | --- | --- |
| Ex. 116 | 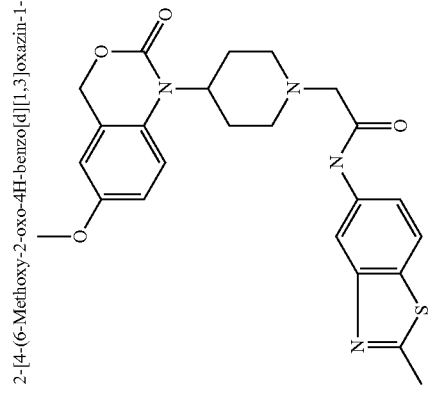 N-(3-Dimethylamino-phenyl)-2-[4-(2-oxo-4H-benzo[d][1,3]oxazin-1-yl)-piperidin-1-yl]-acetamide. | 1H-NMR<br>1.9 (d, J=11.6 Hz, 2 H) 2.5 (m, 2 H) 2.8 (s, 3 H) 2.9 (qd, J=12.5, 4.3 Hz, 2H) 3.1 (d, J=11.1 Hz, 2H) 3.2 (s, 2 H) 3.8 (s, 3 H) 3.8 (m, 1 H) 5.1 (s, 2H) 6.7 (d, J=2.5 Hz, 1 H) 6.9 (m, 1 H) 7.0 (d, J=9.1 Hz, 1 H) 7.6 (dd, J=8.6, 2.0 Hz, 1 H) 7.8 (d, J=8.6 Hz, 1 H) 8.3 (d, J=2.0 Hz, 1 H) 9.3 (s, 1 H). (CDCl₃-d)<br>IR (KBr)<br>1701, 1505, 1464, 1279, 1214, 1043<br>M.P.: 91° C. |

-continued
| Ex. 117 | 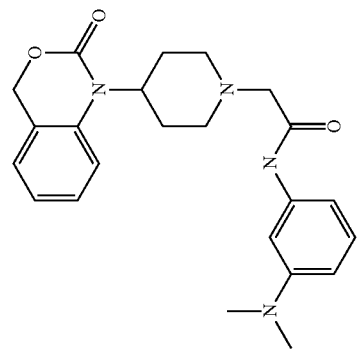 | 1H-NMR<br>1.9 (d, J=11.9 Hz, 2 H) 2.4 (t, J=11.8 Hz, 2 H) 2.9 (tq, J=12.4, 3.9 Hz, 2 H) 3.0 (s, 6 H) 3.1 (d, J=11.7 Hz, 2 H) 3.2 (s, 2 H) 3.8 (m, 1 H) 5.1 (s, 2 H) 6.5 (dd, J=8.4, 2.4 Hz, 1 H) 6.9 (d, J=7.9 Hz, 1 H) 7.1(m, 5 H) 7.4 (t, J=7.8 Hz, 1 H) 9.0 (s, 1 H) (CDCl$_3$-d)<br>IR (KBr)<br>3410, 2913, 1719, 1686, 1528, 1498, 1466, 1287, 1203, 1048, 764<br>M.P.: 148–153° C. |
N-(4-Dimethylamino-phenyl)-2-[4-(2-oxo-4H-benzo[d][1,3]oxazin-1-yl)-piperidin-1-yl]-acetamide.
| Ex. 118 | | 1H-NMR<br>1.9 (d, J=13.7 Hz, 2 H) 2.4 (t, J=12.1 Hz, 2 H) 2.9 (m, 2 H) 2.9 (s, 6 H) 3.1 (d, J=11.5 Hz, 2 H) 3.2 (s, 2 H) 3.8 (m, 1 H) 5.1 (s, 2 H) 6.7 (m, 2 H) 7.1 (m, 3 H) 7.4 (m, 1 H) 7.5 (m, 2 H) 8.9 (s, 1 H) (CDCl$_3$-d)<br>IR (KBr)<br>3392, 1718, 1525, 1499, 1292, 1205, 1134, 1046, 813, 768, 753<br>M.P.: 128° C. |
N-(3-Dimethylamino-phenyl)-2-[4-(8-methyl-2-oxo-4H-benzo[d][1,3]oxazin-1-yl)-piperidin-1-yl]-acetamide.

| | -continued | |
|---|---|---|
| Ex. 119 | 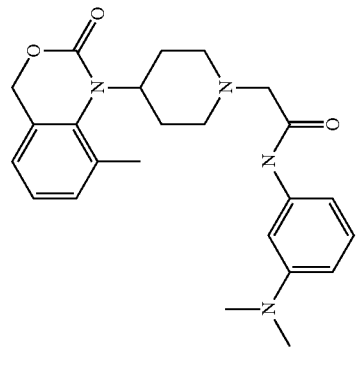 | 1H-NMR<br>2.0 (d, J=11.5 Hz, 2 H) 2.3 (t, J=11.4 Hz, 2 H) 2.4 (s, 3 H) 2.9 (m, 2 H) 3.0 (s, 6H) 3.1 (m, 2H) 3.4 (m, 1H) 5.0 (s, 2H) 6.5 (m, 1 H) 6.9 (d, J=8.1 Hz, 1 H) 7.0 (m, 2 H) 7.2 (m, 3 H) 9.0 (s, 1 H) (CDCl$_3$-d)<br>IR (KBr)<br>3346, 1719, 1677, 1611, 1500, 1474, 1283, 1217, 1036, 775<br>M.P.: 166° C. |
| | N-(4-Dimethylamino-phenyl)-2-[4-(8-methyl-2-oxo-4H-benzo[d][1,3]oxazin-1-yl)-piperidin-1-yl]-acetamide. | |
| Ex. 120 | | 1H-NMR<br>2.0 (d, J=11.9 Hz, 2 H) 2.3 (t, J=11.6 Hz, 2 H) 2.4 (s, 3 H) 2.9 (m, 2 H) 2.9 (s, 6 H) 3.1 (d, J=11.7 Hz, 2 H) 3.1 (s, 2 H) 3.4 (tt, J=11.7, 3.7 Hz, 1 H) 5.0 (s, 2 H) 6.7 (d, J=8.8 Hz, 2 H) 7.0 (m, 2 H) 7.2 (d, J=6.0 Hz, 1 H) 7.5 (d, J=9.0 Hz, 2 H) 8.9 (s, 1 H) (CDCl$_3$-d)<br>IR (KBr)<br>3346, 1719, 1672, 1524, 1283, 1219, 1036, 813<br>M.P.: 152° C. |
| | N-(3-Dimethylamino-phenyl)-2-[4-(6-methyl-2-oxo-4H-benzo[d][1,3]oxazin-1-yl)-piperidin-1-yl]-acetamide | |

-continued
Ex. 121
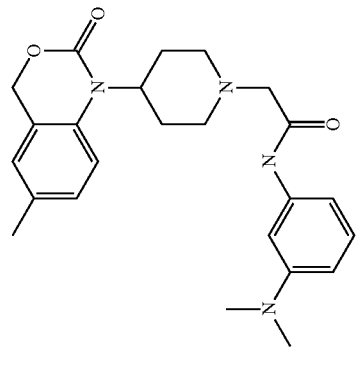
N-(4-Dimethylamino-phenyl)-2-[4-(6-methyl-2-oxo-4H-benzo[d][1,3]oxazin-1-yl)-piperidin-1-yl]-acetamide.
1H-NMR
1.9 (d, J=12.6 Hz, 2 H) 2.3 (s, 3 H) 2.4 (m, 2 H) 2.9 (m, 2 H) 3.0 (s, 6 H) 3.1 (d, J=12.3 Hz, 2 H) 3.2 (s, 2 H) 3.8 (m, 1 H) 6.5 (s, 1 H) 6.9 (d, J=19.0 Hz, 3 H) 7.2 (m, 3 H) 9.0 (s, 1 H) (CDCl$_3$-d)
IR (KBr)
3346, 1727, 1671, 1610, 1501, 1294, 1215, 1042, 806, 760
M.P.: 134–138° C.
Ex. 122
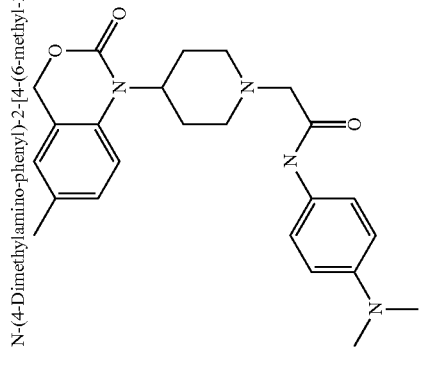
N-(4-Diethylamino-phenyl)-2-[4-(2-oxo-4H-benzo[d][1,3]oxazin-1-yl)-piperidin-1-yl]-acetamide.
1H-NMR
1.9 (d, J=11.9 Hz, 2 H) 2.3 (s, 3 H) 2.4 (s, 2 H) 2.8 (s, 2 H) 2.9 (s, 6 H) 3.1 (d, 2 H) 3.2 (s, 2 H) 3.8 (s, 1 H) 5.0 (s, 2 H) 6.7 (d, J=8.9 Hz, 2 H) 7.0 (m, 2 H) 7.1 (d, J=8.4 Hz, 1 H) 7.5 (d, J=8.9 Hz, 2 H) 8.9 (s, 1 H) (CDCl$_3$-d)
IR (KBr)
3278, 1719, 1523, 1509, 1214, 1045, 811, 763
M.P.: 120° C.

-continued

Ex. 123

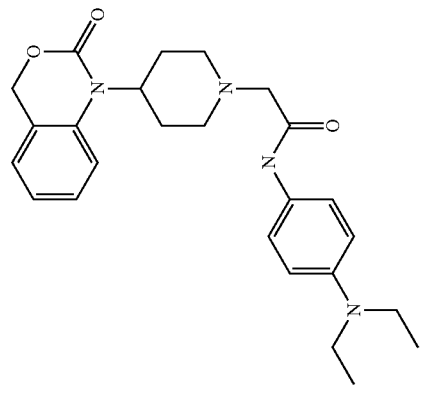

1H-NMR
1.1 (t, J=7.0 Hz, 6 H) 1.9 (d, J=12.3 Hz, 2 H) 2.4 (td, J=11.9, 2.0 Hz, 2 H) 2.9 (m, 2 H) 3.1 (d, J=11.7 Hz, 2 H) 3.2 (s, 2 H) 3.3 (q, J=7.1 Hz, 4 H) 3.8 (m, 1 H) 5.1 (s, 2 H) 6.7 (d, J=9.0 Hz, 2 H) 7.1 (m, 3 H) 7.4 (d, J=9.0 Hz, 1 H) 7.4 (d, J=9.0 Hz, 2 H) 8.9 (s, 1 H) (CDCl$_3$-d)
IR (KBr)
3338, 1720, 1677, 1523, 1499, 1261, 1203, 1049, 817, 753
M.P.: 129° C.

2-{2-[4-(2-Oxo-4H-benzo[d][1,3]oxazin-1-yl)-piperidin-1-yl]-acetylamino}-benzoic acid methyl ester.

Ex. 124

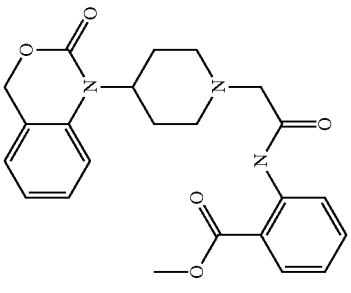

1H-NMR
1.9 (d, J=11.7 Hz, 2 H) 2.4 (td, J=11.6, 1.8 Hz, 2 H) 3.0 (qd, J=12.4, 3.9 Hz, 2 H) 3.1 (d, J=11.3 Hz, 2 H) 3.2 (s, 2 H) 4.0 (s, 3 H) 4.2 (qd, J=12.3, 3.8 Hz, 1 H) 5.1 (s, 2 H) 7.1 (q, J=7.1 Hz, 2 H) 7.2 (t, J=6.1 Hz, 1H) 7.3 (m, 1 H) 7.5 (d, J=8.2 Hz, 1 H) 7.5 (m, 1 H) 8.0 (dd, J=8.0, 1.6 Hz, 1 H) 8.8 (m, 1 H) 12.1 (s, 1 H) (CDCl$_3$-d)
IR (KBr)
3232, 1702, 1583, 1521, 1450, 1385, 1262, 1204, 1090, 1045, 772, 749
M.P.: 180° C.

2-{2-[4-(8-Methyl-2-oxo-4H-benzo[d][1,3]oxazin-1-yl)-piperidin-1-yl]-acetylamino}-benzoic acid methyl ester.

-continued

| Ex. 125 | 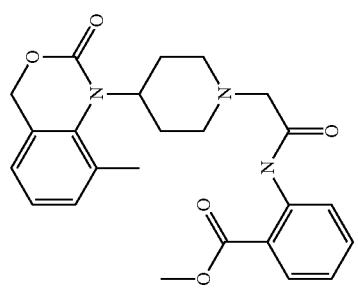 | 1H-NMR<br>1.9 (d, J=12.3 Hz, 2 H) 2.3 (t, J=12.7 Hz, 2 H) 2.4 (s, 3 H) 3.0 (m, 4 H) 3.2 (s, 2 H) 3.4 (m, 1H) 4.1 (s, 3 H) 5.0 (s, 2 H) 7.1 (m, 3 H) 7.2 (d, J=7.3 Hz, 1 H) 7.5 (m, 1 H) 8.0 (dd, J=8.0, 1.7 Hz, 1 H) 8.8 (d, J=8.4 Hz, 1 H) 12.2 (s, 1 H) (CDCl$_3$-d)<br>IR (KBr)<br>3202, 1727, 1705, 1508, 1449, 1270, 1215, 1089, 1033, 765<br>M.P.: 169° C.<br><br>N-(2-Methoxy-dibenzofuran-3-yl)-2-[4-(2-oxo-4H-benzo[d][1,3]oxazin-1-yl)-piperidin-1-yl]-acetamide hydrochloride |
| Ex. 126 | 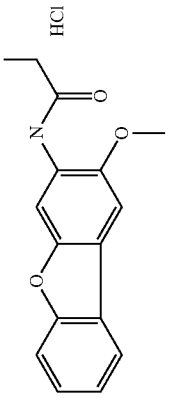 | 1H-NMR<br>2.1 (d, J=13.9 Hz, 2 H) 2.4 (s, 3 H) 2.9 (m, 2 H) 3.6 (d, J=11.2 Hz, 2 H) 3.8 (m, 1 H) 4.0 (m, 3 H) 4.2 (s, 2 H) 5.1 (s, 2 H) 7.1 (m, 2 H) 7.3 (d, J=7.5 Hz, 1 H) 7.4 (t, J=7.6 Hz, 1 H) 7.5 (t, J=7.8 Hz, 1 H) 7.7 (d, J=8.1 Hz, 1 H) 7.9 (s, 1 H) 8.1 (d, J=6.8 Hz, 1 H) 8.4 (s, 1 H) 10.2 (s, 1 H) (DMSO-d6)<br>IR (KBr)<br>3423, 1701, 1678, 1534, 1474, 1200, 1171, 1035, 760<br>M.P.: 272° C.<br><br>N-2-[4-(6-Chloro-2-oxo-4H-benzo[d][1,3]oxazin-1-yl)-piperidin-1-yl]N-(2-methoxy-dibenzofuran-3-yl-acetamide hydrochloride |

-continued

| | | |
|---|---|---|
| Ex. 127 | 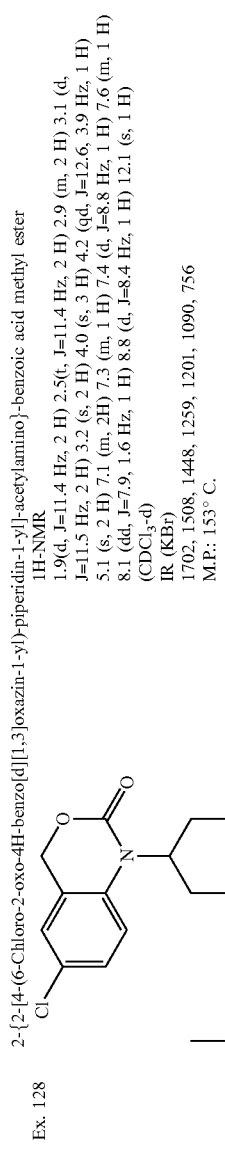 | 1H-NMR<br>2.0 (d, J=12.6 Hz, 2 H) 2.9 (m, 2 H) 3.3 (m, 2 H) 3.5 (m, 1 H) 3.7 (d, J=10.1 Hz, 2 H) 4.0 (s, 3 H) 4.3 (s, 2 H) 5.2 (s, 2 H) 7.4 (m, 5 H) 7.7 (d, J=8.1 Hz, 1 H) 7.9 (s, 1 H) 8.1 (d, J=7.7 Hz, 1 H) 8.4 (s, 1 H) 10.2 (s, 1 H) (DMSO-d6)<br>IR (KBr)<br>3422, 1701, 1541, 1459, 1299, 1196, 1166, 1036, 764<br>M.P.: 197° C. |
| Ex. 128 | 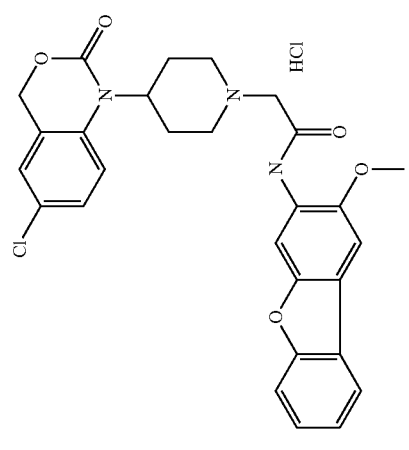 | 1H-NMR<br>1.9 (d, J=11.4 Hz, 2 H) 2.5 (t, J=11.4 Hz, 2 H) 2.9 (m, 2 H) 3.1 (d, J=11.5 Hz, 2 H) 3.2 (s, 2 H) 4.0 (s, 3 H) 4.2 (qd, J=12.6, 3.9 Hz, 1 H) 5.1 (s, 2H) 7.1 (m, 2H) 7.3 (m, 1 H) 7.4 (d, J=8.8 Hz, 1 H) 7.6 (m, 1 H) 8.1 (dd, J=7.9, 1.6 Hz, 1 H) 8.8 (d, J=8.4 Hz, 1 H) 12.1 (s, 1 H) (CDCl₃-d)<br>IR (KBr)<br>1702, 1508, 1448, 1259, 1201, 1090, 756<br>M.P.: 153° C. |

2-{2-[4-(6-Chloro-2-oxo-4H-benzo[d][1,3]oxazin-1-yl)-piperidin-1-yl]-acetylamino}-benzoic acid methyl ester 2-{2-[4-(6-Methyl-2-oxo-4H-benzo[d][1,3]oxazin-1-yl)-piperidin-1-yl]-acetylamino}-benzoic acid methyl ester -continued

| | | |
|---|---|---|
| Ex. 129 | 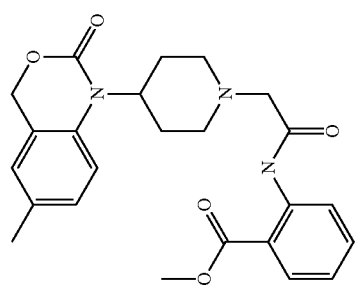 2-[4-(6-Chloro2-oxo-4H-benzo[d][1,3]oxazin-1-yl)-piperidin-1-yl] | 1H-NMR 1.9 (d, J=11.4 Hz, 2 H) 2.3 (s, 3 H) 2.4 (m, 2 H) 2.9 (qd, J=12.4, 3.8 Hz, 2 H) 3.1 (d, J=11.4 Hz, 2 H) 3.2 (s, 2 H) 4.0 (s, 3 H) 4.2 (m, 1 H) 5.0 (s, 2 H) 7.0 (s, 1 H) 7.1 (m, 2 H) 7.3 (d, J=8.4 Hz, 1 H) 7.6 (t, J=7.0 Hz, 1 H) 8.1 (dd, J=8.1, 1.6 Hz, 1 H) 8.8 (m, 1 H) 12.1 (s, 1 H) (CDCl₃-d) IR (KBr) 1701, 1509, 1448, 1265, 1219, 1091, 756 M.P.: 153° C. |
| Ex. 130 | 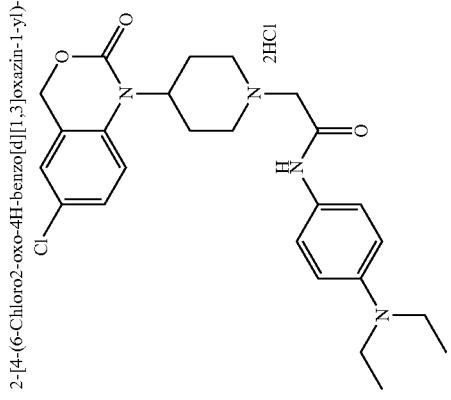 2-[4-(6-Chloro-2-oxo-4H-benzo[d][1,3]oxazin-1-yl)-piperidin-1-yl]-N-{4-[ethyl-(2-hydroxy-ethyl)-amino]-phenyl}-acetamide dihydrochloride | 1H-NMR 1.0 (t, J=7.0 Hz, 6 H) 2.0 (d, J=13.7 Hz, 2 H) 2.9 (m, 2 H) 3.4 (m, 6 H) 3.6 (d, J=13.0 Hz, 2 H) 4.3 (m, 3 H) 5.2 (s, 2 H) 7.4 (s, 3 H) 7.8 (s, 4 H) 10.3 (s, 1H) 11.5 (s, 1H) 12.9 (s, 1 H) (DMSO-d6) IR (KBr) 3427, 2980, 2423, 1708, 1515, 1494, 1373, 1317, 1297, 1200 M.P. |

2-[4-(6-Chloro-2-oxo-4H-benzo[d][1,3]oxazin-1-yl)-piperidin-1-yl]-N-(4-diethylamino-phenyl)-acetamide dihydrochloride -continued

| Ex. 131 | 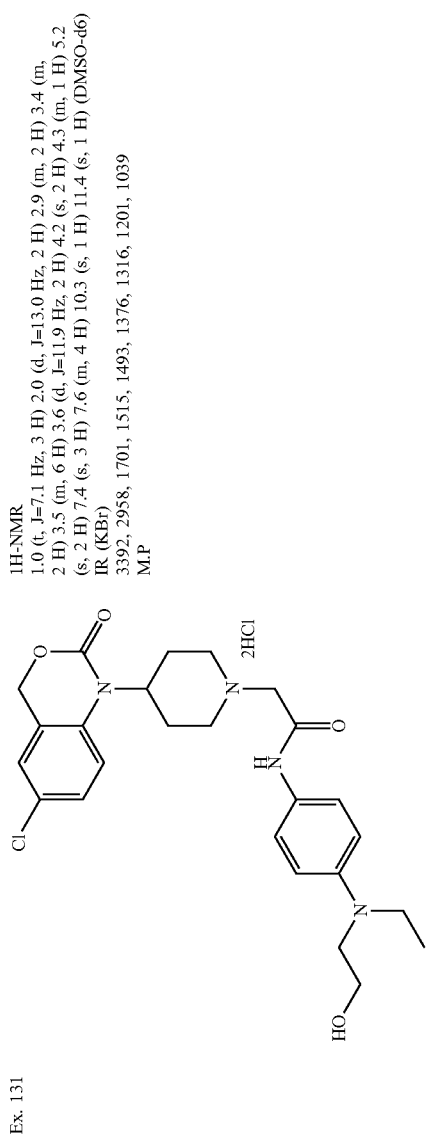 | 1H-NMR<br>1.0 (t, J=7.1 Hz, 3 H) 2.0 (d, J=13.0 Hz, 2 H) 2.9 (m, 2 H) 3.4 (m, 2 H) 3.5 (m, 6 H) 3.6 (d, J=11.9 Hz, 2 H) 4.2 (s, 2 H) 4.3 (m, 1 H) 5.2 (s, 2 H) 7.4 (s, 3 H) 7.6 (m, 4 H) 10.3 (s, 1 H) 11.4 (s, 1 H) (DMSO-d6)<br>IR (KBr)<br>3392, 2958, 1701, 1515, 1493, 1376, 1316, 1201, 1039<br>M.P |
|---|---|---|
| | N-{4-[ethyl-(2-hydroxy-ethyl)-amino]-phenyl}-2-[4-(6-methyl-2-oxo-4H-benzo[d][1,3]oxazin-1-yl)-piperidin-1-yl]-acetamide dihydrochloride | |
| Ex. 132 | 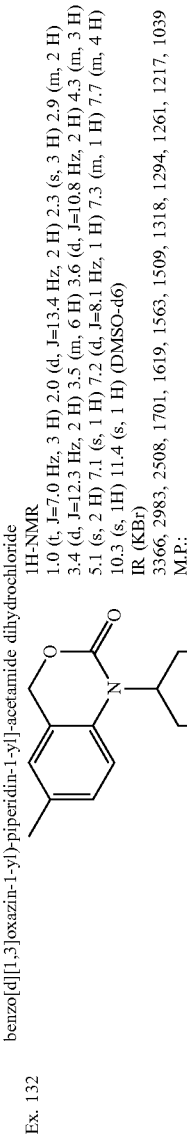 | 1H-NMR<br>1.0 (t, J=7.0 Hz, 3 H) 2.0 (d, J=13.4 Hz, 2 H) 2.3 (s, 3 H) 2.9 (m, 2 H) 3.4 (d, J=12.3 Hz, 2 H) 3.5 (m, 6 H) 3.6 (d, J=10.8 Hz, 2 H) 4.3 (s, 3 H) 5.1 (s, 2 H) 7.1 (s, 1 H) 7.2 (d, J=8.1 Hz, 1 H) 7.3 (m, 1 H) 7.7 (m, 4 H) 10.3 (s, 1H) 11.4 (s, 1 H) (DMSO-d6)<br>IR (KBr)<br>3366, 2983, 2508, 1701, 1619, 1563, 1509, 1318, 1294, 1261, 1217, 1039<br>M.P.: |
| | N-(4-Diethylamino-phenyl)-2-[4-(6-methyl-2-oxo-4H-benzo[d][1,3]oxazin-1-yl)-piperidin-1-yl]-acetamide dihydrochloride | |

-continued

| Ex. 133 | 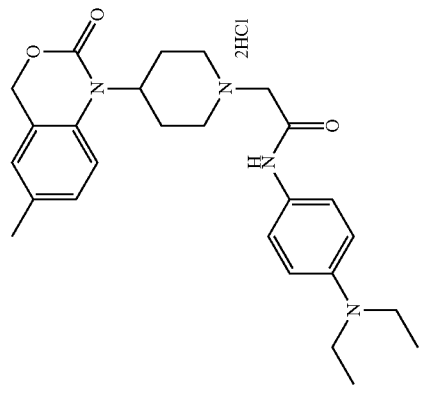 | 1H-NMR<br>1.0 (t, J=7.0 Hz, 6 H) 2.0 (d, J=12.1 Hz, 2 H) 2.3 (s, 3 H) 2.9 (m, 2 H) 3.5 (m, 6 H) 3.6 (d, J=11.0 Hz, 2 H) 4.3 (m, 3 H) 5.1 (s, 2 H) 7.1 (s, 1 H) 7.2 (d, J=8.6 Hz, 1 H) 7.3 (m, J=8.6 Hz, 1 H) 7.8 (m, 4 H) 10.3 (s, 1 H) 11.4 (s, 1 H) 12.9 (s, 1 H) (DMSO-d6)<br>IR (KBr)<br>3423, 2982, 1701, 1618, 1561, 1509, 1459, 1318, 1294, 1215, 1039<br>M.P.: |
|---|---|---|
| | N-(4-Diethylamino-phenyl)-2-[4-(8-methyl-2-oxo-4H-benzo[d][1,3]oxazin-1-yl)-piperidin-1-yl]-acetamide dihydrochloride | |
| Ex. 134 | 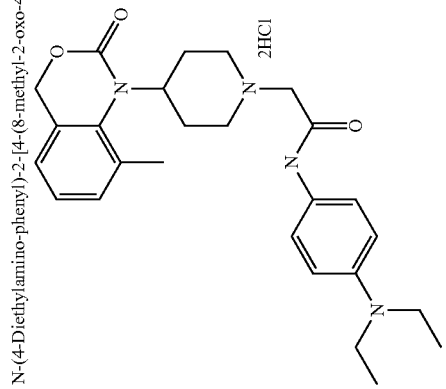 | 1H-NMR<br>1.0 (t, J=7.0 Hz, 6 H) 2.1 (d, J=13.5 Hz, 2 H) 2.4 (s, 3 H) 2.9 (m, 2 H) 3.3 (m, 4 H) 3.5 (m, 4 H) 3.8 (t, J=11.6 Hz, 1 H) 4.2 (s, 2 H) 5.1 (s, 2 H) 7.1 (m, 2 H) 7.3 (d, J=6.6 Hz, 1 H) 7.8 (s, 4 H) 10.2 (s, 1 H) 11.4 (s, 1 H) 12.8 (s, 1 H) (DMSO-d6)<br>IR (KBr)<br>3412, 2804, 1693, 1622, 1577, 1519, 1473, 1382, 1289, 1261, 1224, 1021<br>M.P. |
| | N-{4-[ethyl-(2-hydroxy-ethyl)-amino]-phenyl}-2-[4-(8-methyl-2-oxo-4H-benzo[d][1,3]oxazin-1-yl)-piperidin-1-yl]-acetamide dihydrochloride | |

-continued
| Ex. 135 | 1H-NMR<br>1.0 (t, J=7.0 Hz, 3 H) 2.1 (d, J=12.5 Hz, 2 H) 2.4 (s, 3 H) 2.9 (m, 2 H) 3.3 (m, 2 H) 3.6 (m, 9 H) 4.1 (s, 2 H) 5.1 (s, 2 H) 7.1 (m, 2 H) 7.3 (d, J=7.1 Hz, 1 H) 7.7 (s, 4 H) 10.2 (s, 1 H) 11.3 (s, 1 H) (DMSO-d6)<br>IR (KBr)<br>3387, 2983, 2624, 1701, 1566, 1515, 1383, 1320, 1281, 1219<br>M.P.: |
|---|---|
| 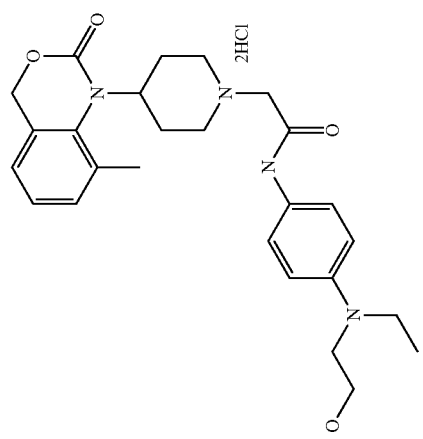<br>N-Benzo[1,3]dioxol-5-yl-2-[4-(2-oxo-4H-benzo[d][1,3]oxazin-1-yl)-piperidin-1-yl]-acetamide | |
| Ex. 136 | 1H-NMR<br>1.9 (d, J=13.4 Hz, 2 H) 2.4 (td, J=12.0, 2.0 Hz, 2 H) 2.9 (m, 2 H) 3.1 (d, J=9.5 Hz, 2 H) 3.2 (s, 2 H) 3.8 (tt, J=12.0, 4.0 Hz, 1 H) 5.1 (s, 2 H) 6.0 (s, 2H) 6.8 (d, J=8.2 Hz, 1 H) 6.9 (m, 1 H) 7.1 (m, 3 H) 7.4 (m, 2 H) 9.0 (s, 1 H) (CDCl3-d)<br>IR (KBr)<br>3417, 1719, 1686, 1542, 1491, 1241, 1204, 1034<br>M.P.: 183.8 |
| 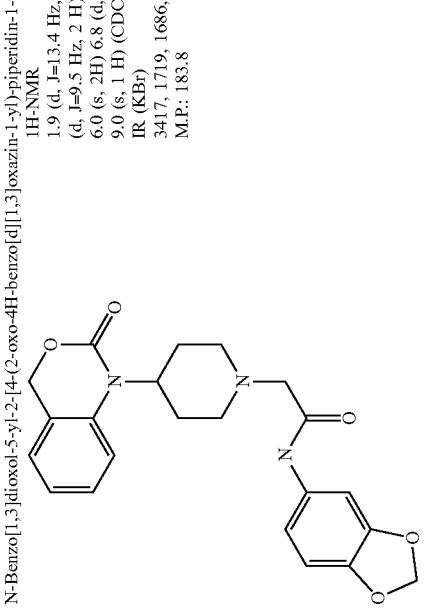<br>N-Benzo[1,3]dioxol-5-yl-2-[4-(6-methyl-2-oxo-4H-benzo[d][1,3]oxazin-1-yl)-piperidin-1-yl]-acetamide | |

-continued

| | |
|---|---|
| Ex. 137 | 1H-NMR<br>1.9 (d, J=10.4 Hz, 2 H) 2.3 (s, 3 H) 2.4 (t, J=11.4 Hz, 2 H) 2.9 (qd, J=12.3, 4.1 Hz, 2 H) 3.1 (d, J=11.9 Hz, 2 H) 3.2 (s, 2 H) 3.8 (tt, J=11.8, 3.7 Hz, 1 H) 5.1 (s, 2 H) 6.0 (s, 2 H) 6.8 (d, J=8.2 Hz, 1 H) 6.9 (m, 3 H) 7.1 (d, J=9.9 Hz, 1 H) 7.3 (d, J=2.0 Hz, 1 H) 9.1 (s, 1 H) (CDCl$_3$-d)<br>IR (KBr)<br>3408, 1709, 1531, 1484, 1211, 1029, 809<br>M.P.: 123.0 |
| 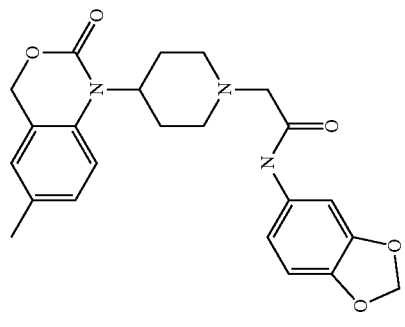<br>N-Benzo[1,3]dioxol-5-yl-2-[4-(6-chloro-2-oxo-4H-benzo[d][1,3]oxazin-1-yl)-piperidin-1-yl]-acetamide | 1H-NMR<br>1.9 (d, J=12.6 Hz, 2 H) 2.4 (m, 2 H) 2.9 (qd, J=12.3, 3.7 Hz, 2 H) 3.1 (d, J=11.5 Hz, 2 H) 3.2 (s, 2 H) 3.8 (tt, J=11.9, 3.8 Hz, 1 H) 5.1 (s, 2 H) 6.0 (s, 2 H) 6.8 (d, J=8.2 Hz, 1 H) 6.9 (m, 1 H) 7.0 (d, J=8.6 Hz, 1 H) 7.2 (d, J=2.4 Hz, 1 H) 7.3 (m, 2 H) 9.0 (s, 1 H) (CDCl$_3$-d)<br>IR (KBr)<br>3300, 1719, 1686, 1529, 1490, 1241, 1199, 1035<br>M.P.: 185.7–187.3 |
| Ex. 138 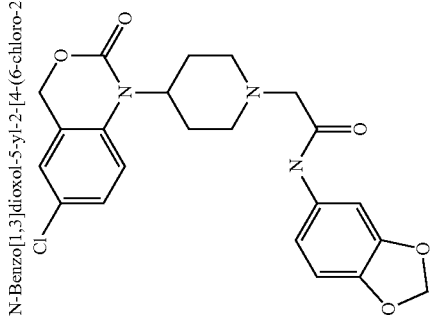<br>N-Benzo[1,3]dioxol-5-yl-2-[4-(8-methyl-2-oxo-4H-benzo[d][1,3]oxazin-1-yl)-piperidin-1-yl]-acetamide | |

| | -continued | |
|---|---|---|
| Ex. 139 | 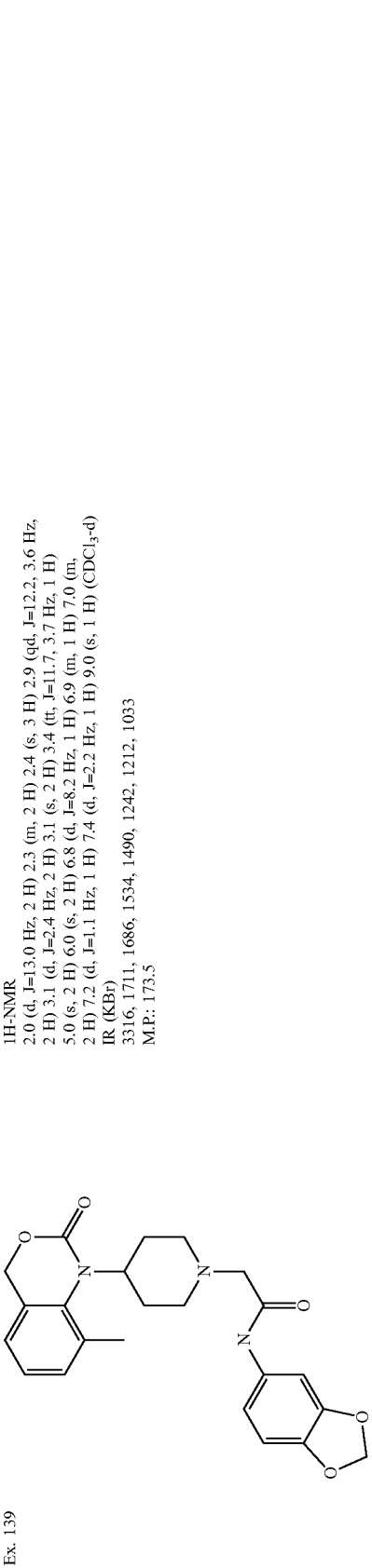<br>N-{4-[ethyl-(2-hydroxy-ethyl)-amino]-phenyl}-2-[4-(2-oxo-4H-benzo[d][1,3]oxazin-1-yl)-piperidin-1-yl]-acetamide dihydrochloride | 1H-NMR<br>2.0 (d, J=13.0 Hz, 2 H) 2.3 (m, 2 H) 2.4 (s, 3 H) 2.9 (qd, J=12.2, 3.6 Hz, 2 H) 3.1 (d, J=2.4 Hz, 2 H) 3.4 (tt, J=11.7, 3.7 Hz, 1 H) 5.0 (s, 2 H) 6.0 (s, 2 H) 6.8 (d, J=8.2 Hz, 1 H) 6.9 (m, 1 H) 7.0 (m, 2 H) 7.2 (d, J=1.1 Hz, 1 H) 7.4 (d, J=2.2 Hz, 1 H) 9.0 (s, 1 H) (CDCl$_3$-d)<br>IR (KBr)<br>3316, 1711, 1686, 1534, 1490, 1242, 1212, 1033<br>M.P.: 173.5 |
| Ex. 140 | 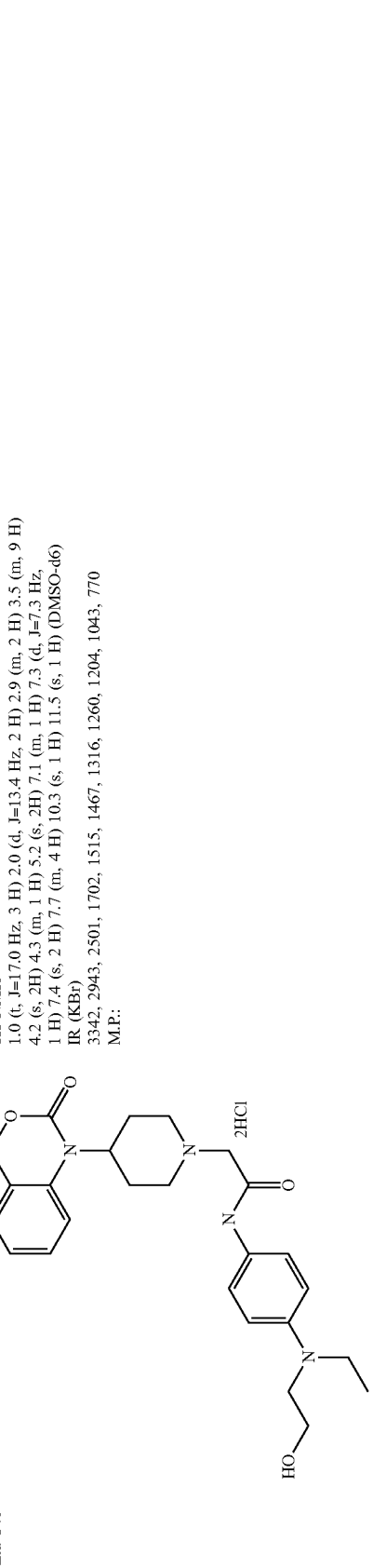<br>2-[4-(6-Chloro-2-oxo-4H-benzo[d][1,3]oxazin-1-yl)-piperidin-1-yl]-N-(4-dimethylamino-phenyl)-acetamide dihydrochloride | 1H-NMR<br>1.0 (t, J=17.0 Hz, 3 H) 2.0 (d, J=13.4 Hz, 2 H) 2.9 (m, 2 H) 3.5 (m, 9 H) 4.2 (s, 2H) 4.3 (m, 1 H) 5.2 (s, 2H) 7.1 (m, 1 H) 7.3 (d, J=7.3 Hz, 1 H) 7.4 (s, 2 H) 7.7 (m, 4 H) 10.3 (s, 1 H) 11.5 (s, 1 H) (DMSO-d6)<br>IR (KBr)<br>3342, 2943, 2501, 1702, 1515, 1467, 1316, 1260, 1204, 1043, 770<br>M.P.: |

-continued
| Ex. 141 | 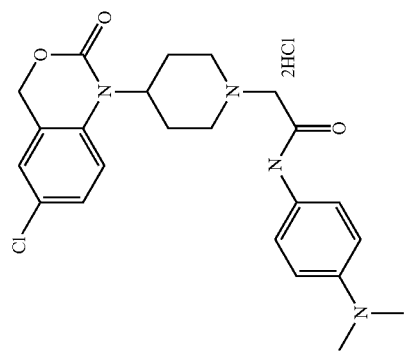 | 1H-NMR 2.0 (d, J=12.6 Hz, 2 H) 2.9 (m, 2 H) 3.0 (s, 6 H) 3.4 (d, J=11.9 Hz, 2 H) 3.6 (m, 2H) 4.2 (s, 2H) 4.3 (m, 1H) 5.2 (s, 2H) 7.4 (m, 4H) 7.6 (m, 3 H) 10.2 (s, 1 H) 11.1 (s, 1 H) (DMSO-d6) IR (KBr) 3448, 2958, 2400, 1716, 1701, 1518, 1495, 1200 M.P.: |

Example 142

N-(9-Hydroxy-9H-fluoren-3-yl)-2-[4-(4-methyl-2-oxo-4H-benzo[d][1,3]oxazin-1-yl)-piperidin-1-yl]-acetamide

Example 143

N-(9-Ethyl-9H-carbazol-3-yl)-2-[4-(4-methyl-2-oxo-4H-benzo[d][1,3]oxazin-1-yl)-piperidin-1-yl]-acetamide

Example 144

2-[4-(4-Methyl-2-oxo-4H-benzo[d][1,3]oxazin-1-yl)-piperidin-1-yl]-N-(4-phenoxy-phenyl)-acetamide

Example 145

2-{2-[4-(2-Oxo-4H-benzo[d][1,3]oxazin-1-yl)-piperidin-1-yl]-acetamino}-benzoic acid

Example 146

1-{1-[2-(6-Fluoro-2-methyl-3,4-dihydro-2H-quinoline-1-yl)-2-oxo-ethyl]-piperidin-4-yl}-1,4-dihydro-benzo[d][1,3]oxazin-2-one

Example 147

6-Chloro-1-{1-[2-(6-fluoro-2-methyl-3,4-dihydro-2H-quinoline-1-yl)-2-oxo-ethyl]-piperidin-4-yl}-1,4-dihydro-benzo[d][1,3]oxazin-2-one

Example 148

1-{1-[2-(6-Fluoro-2-methyl-3,4-dihydro-2H-quinoline-1-yl)-2-oxo-ethyl]-piperidin-4-yl}-6-methyl-1,4-dihydro-benzo[d][1,3]oxazin-2-one

Example 149

1-{1-[2-(6-Fluoro-2-methyl-3,4-dihydro-2H-quinoline-1-yl)-2-oxo-ethyl]-piperidin-4-yl}-8-methyl-1,4-dihydro-benzo[d][1,3]oxazin-2-one

Example 150

1-{1-[2-(6-Methoxy-2,2,4-trimethyl-3,4-dihydro-2H-quinoline-1-yl)-2-oxo-ethyl]-piperidin-4-yl}-1,4-dihydro-benzo[d][1,3]oxazin-2-one

Example 151

6-Chloro-1-{1-[2-(6-methoxy-2,2,4-trimethyl-3,4-dihydro-2H-quinoline-1-yl)-2-oxo-ethyl]-piperidin-4-yl}-1,4-dihydro-benzo[d][1,3]oxazin-2-one

Example 152

1-{1-[2-(6-Methoxy-2,2,4-trimethyl-3,4-dihydro-2H-quinoline-1-yl)-2-oxo-ethyl]-piperidin-4-yl}-8-methyl-1,4-dihydro-benzo[d][1,3]oxazin-2-one

Example 153

1-{1-[2-(6-Methoxy-2,2,4-trimethyl-3,4-dihydro-2H-quinoline-1-yl)-2-oxo-ethyl]-piperidin-4-yl}-6-methyl-1,4-dihydro-benzo[d][1,3]oxazin-2-one

Example 154

N-(9-Hydroxy-9H-fluoren-3-yl)-2-[4-(2-oxo-7-trifluormethyl-4H-benzo[d][1,3]oxazin-1-yl)-piperidin-1-yl]-acetamide

Example 155

N-(9H-carbazol-3-yl)-2-[4-(2-oxo-7-trifluormethyl-4H-benzo[d][1,3]oxazin-1-yl)-piperidin-1-yl]-acetamide

Example 156

2-[4-(2-Oxo-7-trifluormethyl-4H-benzo[d][1,3]oxazin-1-yl)-piperidin-1-yl]-N-(4-phenoxy-phenyl)-acetamide

Example 157

N-(9-Ethyl-9H-carbazol-3-yl)-2-[4-(2-oxo-7-trifluormethyl-4H-benzo[d][1,3]oxazin-1-yl)-piperidin-1-yl]-acetamide

Example 158

2-4-(6,7-Difluoro-2-oxo-4H-benzo[d][1,3]oxazin-1-yl)-piperidin-1-yl]-N-(9-hydroxy-9H-fluoren-3-yl)-acetamide

Example 159

N-(9H-carbazol-3-yl)-2-[4-(6,7-difluoro-2-oxo-4H-benzo[d][1,3]oxazin-1-yl)-piperidin-1-yl]-acetamide

Example 160

2-4-(6,7-Difluoro-2-oxo-4H-benzo[d][1,3]oxazin-1-yl)-piperidin-1-yl]-N-(4-phenoxy-phenyl)-acetamide

Example 161

2-4-(6,7-Difluoro-2-oxo-4H-benzo[d][1,3]oxazin-1-yl)-piperidin-1-yl]-N-(9-ethyl-9H-carbazol-3-yl)-acetamide

Example 162

2-[4-(4-Methyl-2-oxo-4H-benzo[d][1,3]oxazin-1-yl)-piperidin-1-yl]-N-(9-oxo-9H-fluoren-3-yl)-acetamide

Example 163

2-[4-(6-Chloro-2-oxo-4H-benzo[d][1,3]oxazin-1-yl)-piperidin-1-yl]-N-(3-dimethylamino-phenyl)-acetamide

Example 164

Example of formula per tablet:

| | |
|---|---|
| Compound according to Example 18 | 5 mg |
| Lactose | 60 mg |
| Crystalline cellulose | 25 mg |
| Povidone K 90 | 5 mg |
| Pregelanitized starch | 3 mg |
| Colloidal silica dioxide | 1 mg |
| Magnesium stearate | 1 mg |
| Total weight per tablet | 100 mg |

The above mentioned ingredients were mixed and compressed into a tablet by conventional methods known to those skilled in the art.

Pharmacological Data (a)

According to methods I and III Neuropeptide $Y_5$ and $Y_2$ Binding of the benzoxazine-derived compounds of general formula (I) has been determined. Some of the values are given in the following table 1.

TABLE 1

| Compound according to Example | Neuropeptide $Y_5$ Binding [$^{125}$I]-PYY$_{(3-36)}$ BIBP 3226 sat. Rat cortex $K_i$ (nM) | Neuropeptide $Y_2$ Binding [$^{125}$I]-PYY$_{(3-36)}$ Rat hypoccampus $K_i$ (nM) |
|---|---|---|
| 3 | 6.4 | >1000 |
| 4 | 7.3 | >1000 |
| 5 | 8.3 | >1000 |
| 6 | 18.4 | >1000 |
| 18 | 3.4 | >1000 |
| 20 | 0.87 | >1000 |

(b)

According to method II Neuropeptide $Y_5$ Binding of the benzoxazine-derived compounds of general formula (I) has been determined. Some of the values are given in the following table 2.

TABLE 2

| Compound according to Example | Neuropeptide $Y_5$ Binding [$^{125}$I]-PYY $Y_5$ Rat Recombinant Receptor Cell C6 IC$_{50}$(nM) |
|---|---|
| 107 | 23.5 |
| 111 | 7.7 |
| 112 | 41.8 |
| 114 | 40.7 |
| 116 | 106.0 |

(c)

According to the nocturnal feeding test described above, the effects of the benzoxazine-derived compounds of general formula (I) according to the present invention on food intake has been determined. Some of the results are given in the following table 3.

TABLE 3

| Compound according to Example | Dose (mg/kg) i.p. administration | Effect |
|---|---|---|
| 20 | 40 | Decreases food intake and reduces body weight of treated animals vs. control group |
| 18 | 40 | Decreases food intake and reduces body weight of treated animals vs. control group |
| 35 | 20 | Decreases food intake and reduces body weight of treated animals vs. control group |

The invention claimed is:

1. A benzoxazinone-derived compound of formula (I)

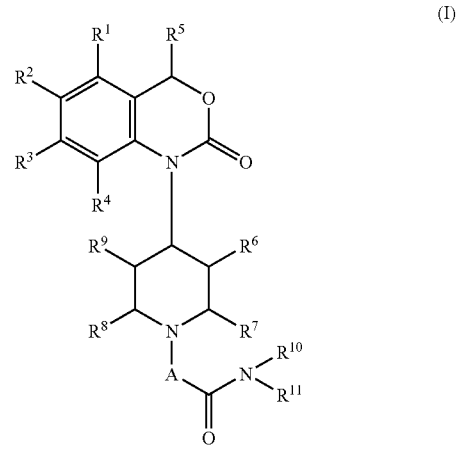

(I)

wherein
$R^1$, $R^2$, $R^3$, $R^4$ are each independently selected from the group consisting of hydrogen, halogen, an unbranched or branched, saturated or unsaturated, optionally at least mono-substituted aliphatic radical, a saturated or unsaturated, optionally at least mono-substituted, optionally at least one heteroatom as ring member containing alicyclic radical, wherein such alicyclic radical may be bonded via an optionally at least mono-substituted alkylene group and/or such alicyclic radical may be condensed with an optionally at least mono-substituted mono- or polycyclic ring-system, an optionally at least mono-substituted aryl or heteroaryl radical, wherein such aryl or heteroaryl radical may be bonded via an optionally at least mono-substituted alkylene group and/or such aryl or heteroaryl radical may be condensed with an optionally at least mono-substituted mono- or polycyclic ring-system, a nitro, cyano, —OR$^{12}$, —OC(=O)R$^{13}$, —SR$^{14}$, —SOR$^{14}$, —SO$_2$R$^{14}$, —NH—SO$_2$R$^{14}$, —SO$_2$NH$_2$ and —NR$^{15}$R$^{16}$ moiety, $R^5$ represents hydrogen, an unbranched or branched, saturated or unsaturated, optionally at least mono-substituted aliphatic radical or a saturated or unsaturated, optionally at least mono-substituted, optionally at least one heteroatom as ring member containing alicyclic radical, $R^6$, $R^7$, $R^8$, $R^9$ are each independently selected from the group consisting of hydrogen, an unbranched or branched, saturated or unsaturated, optionally at least mono-substituted aliphatic radical, a saturated or unsaturated, optionally at least mono-substituted, optionally at least one heteroatom as ring member containing alicyclic radical, a cyano and a $COOR^{17}$ moiety, A represents a bridge member —$CHR^{18}$— or —$CHR^{18}$—$CH_2$—, $R^{10}$ represents hydrogen, an unbranched or branched, saturated or unsaturated, optionally at least mono-substituted aliphatic radical, a saturated or unsaturated, optionally at least mono-substituted, optionally at least one heteroatom as ring member containing alicyclic radical or an optionally at least mono-substituted aryl or heteroaryl radical, wherein such aryl or heteroaryl radical may be bonded via an optionally at least mono-substituted alkylene group and/or such aryl or heteroaryl radical may be condensed with an optionally at least mono-substituted mono- or polycyclic ring-system, $R^{11}$ represents an unbranched or branched, saturated or unsaturated, optionally at least mono-substituted aliphatic radical, a saturated or unsaturated, optionally at least mono-substituted, optionally at least one heteroatom as ring member containing alicyclic radical, wherein such alicyclic radical may be bonded via an optionally at least mono-substituted alkylene group and/or such alicyclic radical may be condensed with an optionally at least mono-substituted mono- or polycyclic ring-system, or an optionally at least mono substituted aryl or heteroaryl radical, wherein such aryl or heteroaryl radical may be bonded via an optionally at least mono-substituted alkylene group and/or such aryl or heteroaryl radical may be condensed with an optionally at least mono-substituted mono- or polycyclic ring-system, or $R^{10}$ and $R^{11}$ together with the bridging nitrogen atom form an optionally at least mono-substituted, saturated, unsaturated or aromatic heterocyclic ring, wherein such heterocyclic ring may contain at least one further heteroatom, and wherein each of these further heteroatoms is selected from the group consisting of N, O, and S and/or such heterocyclic ring may be condensed with an optionally at least mono-substituted mono- or polycyclic ring-system, $R^{12}$ represents hydrogen, an unbranched or branched, saturated or unsaturated, optionally at least mono-substituted aliphatic radical, a saturated or unsaturated, optionally at least mono-substituted, optionally at least one heteroatom as ring member containing alicyclic radical, wherein such alicyclic radical may be bonded via an optionally at least mono-substituted alkylene group and/or such alicyclic radical may be condensed with an optionally at least mono-substituted mono- or polycyclic ring-system, or an optionally at least mono-substituted aryl- or heteroaryl radical, wherein such aryl or heteroaryl radical may be bonded via an optionally at least mono-substituted alkylene group and/or such aryl or heteroaryl radical may be condensed with an optionally at least mono-substituted mono- or polycyclic ring-system, $R^{13}$ represents hydrogen, an unbranched or branched, saturated or unsaturated, optionally at least mono-substituted aliphatic radical, a saturated or unsaturated, optionally at least mono-substituted, optionally at least one heteroatom as ring member containing alicyclic radical, wherein such alicyclic radical may be bonded via an optionally at least mono-substituted alkylene group and/or such alicyclic radical may be condensed with an optionally at least mono-substituted mono- or polycyclic ring-system, or an optionally at least mono-substituted aryl or heteroaryl radical, wherein such aryl or heteroaryl radical may be bonded via an optionally at least mono-substituted alkylene group and/or such aryl or heteroaryl radical may be condensed with an optionally at least mono-substituted mono- or polycyclic ring-system, $R^{14}$ represents an unbranched or branched, saturated or unsaturated, optionally at least mono-substituted aliphatic radical, a saturated or unsaturated, optionally at least mono-substituted, optionally at least one heteroatom as ring member containing alicyclic radical, wherein such alicyclic radical may be bonded via an optionally at least mono-substituted alkylene group and/or such alicyclic radical may be condensed with an optionally at least mono-substituted mono- or polycyclic ring-system, or an optionally at least mono-substituted aryl or heteroaryl radical, wherein such aryl or heteroaryl radical may be bonded via an optionally at least mono-substituted alkylene group and/or such aryl or heteroaryl radical may be condensed with an optionally at least mono-substituted mono- or polycyclic ring-system, $R^{15}$ and $R^{16}$ each are independently selected from the group consisting of hydrogen, an unbranched or branched, saturated or unsaturated, optionally at least mono-substituted aliphatic radical, a saturated or unsaturated, optionally at least mono-substituted, optionally at least one heteroatom as ring member containing alicyclic radical, wherein such alicyclic radical may be bonded via an optionally at least mono-substituted alkylene group and/or such alicyclic radical may be condensed with an optionally at least mono-substituted mono- or polycyclic ring-system, or an optionally at least mono-substituted aryl- or heteroaryl radical, wherein such aryl or heteroaryl radical which may be bonded via an optionally at least mono-substituted alkylene group and/or such aryl or heteroaryl radical may be condensed with an optionally at least mono-substituted mono- or polycyclic ring-system, or $R^{15}$ and $R^{16}$ together with the bridging nitrogen atom form a saturated, unsaturated or aromatic heterocyclic ring, wherein such heterocyclic ring may be at least mono-substituted and/or such heterocyclic ring may contain one or more further heteroatoms and wherein each of these further heteroatom is selected from the group consisting of N, O and S and/or such heterocyclic ring may be condensed with an optionally at least mono-substituted mono- or polycyclic ring-system, $R^{17}$ represents hydrogen, an unbranched or branched, saturated or unsaturated, optionally at least mono-substituted aliphatic radical, a saturated or unsaturated, optionally at least mono-substituted, optionally at least one heteroatom as ring member containing alicyclic radical or an optionally at least mono-substituted aryl or heteroaryl radical, wherein such aryl or heteroaryl radical may be bonded via an optionally at least mono-substituted alkylene group and/or such aryl or heteroaryl radical may be condensed with an optionally at least mono-substituted mono- or polycyclic ring-system, $R^{18}$ represents hydrogen, an unbranched or branched, saturated or unsaturated, optionally at least mono-substituted aliphatic radical, a saturated or unsaturated, optionally at least mono-substituted, optionally at least one heteroatom as ring member containing alicyclic radical or an optionally at least mono-substituted aryl or heteroaryl radical, wherein such aryl or heteroaryl radical may be bonded via an optionally at least mono-substituted alkylene group and/or such aryl or heteroaryl radical may be condensed with an optionally at least mono-substituted mono- or polycyclic ring-system, optionally in form of one of its stereoisomers, its racemate or in form of a mixture of at least two of its stereoisomers, in any mixing ration, or a physiologically acceptable salt thereof, or a solvate, respectively, wherein a mono- or polycyclic ring-system means a 5- or 6-membered monocyclic hydrocarbon ring-system or a hydrocarbon ring-system comprising two 5- or 6-membered rings that are condensed, wherein each of the rings may be saturated, unsaturated or aromatic and may contain one or more heteroatoms as ring members, wherein such heteroatoms may be identical or different and are selected from the group consisting of N, O, S and P.

2. Compounds according to claim 1, characterized in that $R^1$, $R^2$, $R^3$, $R^4$ are each independently selected from the group consisting of H, F, Cl, Br, an unbranched or branched, saturated or unsaturated, optionally at least mono-substituted $C_{1-6}$-aliphatic radical, a saturated or unsaturated, optionally at least mono-substituted, optionally at least one heteroatom as ring member containing $C_{3-8}$-alicyclic radical, wherein such alicyclic radical may be bonded via an optionally at least mono-substituted $C_{1-6}$-alkylene group and/or such alicyclic radical may be condensed with an optionally at least mono-substituted mono- or polycyclic ring-system, an optionally at least mono-substituted, 5- or 6-membered aryl or heteroaryl radical, wherein such aryl or heteroaryl radical may be bonded via an optionally at least mono-substituted $C_{1-6}$-alkylene group and/or such aryl or heteroaryl radical may be condensed with an optionally at least mono-substituted mono- or polycyclic ring-system, a nitro, cyano, $-OR^2$, $-OC(=O)R^{13}$, $-SR^{14}$, $-SOR^{14}$, $-SO_2R^{14}$, $-NH-SO_2R^{14}$, $-SO_2NH_2$ and $-NR^{15}R^{16}$ moiety, $R^5$ represents hydrogen, an unbranched or branched, saturated or unsaturated, optionally at least mono-substituted $C_{1-6}$-aliphatic radical or a saturated or unsaturated, optionally at least mono-substituted, optionally at least one heteroatom as ring member containing $C_{3-8}$-alicyclic radical, $R^6$, $R^7$, $R^8$, $R^9$ are each independently selected from the group consisting of hydrogen, an unbranched or branched, saturated or unsaturated, optionally at least mono-substituted $C_{1-6}$-aliphatic radical, a saturated or unsaturated, optionally at least mono-substituted, optionally at least one heteroatom as ring member containing $C_{3-8}$-alicyclic radical, a cyano and $COOR^{17}$ moiety, A represents a bridge member $-CHR^{18}-$ or $-CHR^{18}-CH_2-$, $R^{10}$ represents hydrogen, an unbranched or branched, saturated or unsaturated, optionally at least mono-substituted $C_{1-6}$-aliphatic radical, a saturated or unsaturated, optionally at least mono-substituted, optionally at least one heteroatom as ring member containing $C_{3-8}$-alicyclic radical or an optionally at least mono-substituted, 5- or 6-membered aryl or heteroaryl radical, wherein such aryl- or heteroaryl radical may be bonded via an optionally at least mono-substituted $C_{1-6}$-alkylene group and/or such aryl or heteroaryl radical may be condensed with an optionally at least mono-substituted mono- or polycyclic ring-system, $R^{11}$ represents an unbranched or branched, saturated or unsaturated, optionally at least mono-substituted $C_{1-6}$-aliphatic radical, a saturated or unsaturated, optionally at least mono-substituted, optionally at least one heteroatom as ring member containing $C_{3-8}$-alicyclic radical, wherein such alicyclic radical may be bonded via an optionally at least mono-substituted $C_{1-6}$-alkylene group and/or such alicyclic radical may be condensed with an optionally at least mono-substituted mono- or polycyclic ring-system or an optionally at least mono substituted 5- or 6-membered aryl or heteroaryl radical, wherein such aryl or heteroaryl radical may be bonded via an optionally at least mono-substituted $C_{1-6}$-alkylene group and/or such aryl- or heteroaryl radical may be condensed with an optionally at least mono-substituted mono- or polycyclic ring-system, or $R^{10}$ and $R^{11}$ together with the bridging nitrogen atom form an optionally at least mono-substituted, saturated, unsaturated or aromatic, 5- or 6-membered heterocyclic ring, wherein such heterocyclic ring may contain at least one further heteroatom as a ring member and/or such heterocyclic ring may be condensed with an optionally at least mono-substituted mono- or polycyclic ringsystem, $R^{12}$ represents hydrogen, an unbranched or branched, saturated or unsaturated, optionally at least mono-substituted $C_{1-6}$-aliphatic radical, a saturated or unsaturated, optionally at least mono-substituted, optionally at least one heteroatom as ring member containing $C_{3-8}$-alicyclic radical wherein such alicyclic radical may be bonded via an optionally at least mono-substituted $C_{1-6}$-alkylene group and/or such alicyclic radical may be condensed with an optionally at least mono-substituted mono- or polycyclic ring-system, or an optionally at least mono-substituted, 5- or 6-membered aryl or heteroaryl radical, wherein such aryl or heteroaryl radical may be bonded via an optionally at least mono-substituted $C_{1-6}$-alkylene group and/or such aryl or heteroaryl radical may be condensed with an optionally at least mono-substituted mono- or polycyclic ring-system, $R^{13}$ represents hydrogen, an unbranched or branched, saturated or unsaturated, optionally at least mono-substituted $C_{1-6}$-aliphatic radical, a saturated or unsaturated, optionally at least mono-substituted, optionally at least one heteroatom as ring member containing $C_{3-8}$-alicyclic radical, which such alicyclic radical may be bonded via an optionally at least mono-substituted $C_{1-6}$-alkylene group and/or such alicyclic radical may be condensed with an optionally at least mono-substituted mono- or polycyclic ring-system, or an optionally at least mono-substituted, 5- or 6-membered aryl or heteroaryl radical, wherein such aryl or heteroaryl radical which may be bonded via an optionally at least mono-substituted $C_{1-6}$-alkylene group and/or may be condensed with an optionally at least mono-substituted mono- or polycyclic ring-system, $R^{14}$ represents an unbranched or branched, saturated or unsaturated, optionally at least mono-substituted $C_{1-6}$-aliphatic radical, a saturated or unsaturated, optionally at least mono-substituted, optionally at least one heteroatom as ring member containing C_{3-8}-alicyclic radical, wherein such alicyclic radical may be bonded via an optionally at least mono-substituted C_{1-6}-alkylene group and/or such alicyclic radical may be condensed with an optionally at least mono-substituted mono- or polycyclic ring-system, or an optionally at least mono-substituted, 5- or 6-membered aryl or heteroaryl radical, wherein such aryl or heteroaryl radical may be bonded via an optionally at least mono-substituted C_{1-6}-alkylene group and/or such aryl or heteroaryl radical may be condensed with an optionally at least mono-substituted mono- or polycyclic ring-system, R$^{15}$ and R$^{16}$ each are independently selected from the group consisting of hydrogen, an unbranched or branched, saturated or unsaturated, optionally at least mono-substituted C_{1-6}-aliphatic radical, a saturated or unsaturated, optionally at least mono-substituted, optionally at least one heteroatom as ring member containing C_{3-8}-alicyclic radical, wherein such alicyclic radical may be bonded via an optionally at least mono-substituted C_{1-6}-alkylene group and/or such alicyclic radical may be condensed with an optionally at least mono-substituted mono- or polycyclic ring-system, or an optionally at least mono-substituted, 5- or 6-membered aryl or heteroaryl radical, wherein such aryl or heteroaryl radical which may be bonded via an optionally at least mono-substituted C_{1-6}-alkylene group and/or such aryl or heteroaryl radical may be condensed with an optionally at least mono-substituted mono- or polycyclic ring-system, or R$^{15}$ and R$^{16}$ together with the bridging nitrogen atom form a saturated, unsaturated or aromatic, 5- or 6-membered heterocyclic ring, which heterocyclic ring may be at least mono-substituted and/or contain at least one further heteroatom as a ring member, R$^{17}$ represents hydrogen, an unbranched or branched, saturated or unsaturated, optionally at least mono-substituted C_{1-6}-aliphatic radical, a saturated or unsaturated, optionally at least mono-substituted, optionally at least one heteroatom as ring member containing C_{3-8}-alicyclic radical or an optionally at least mono-substituted, 5- or 6-membered aryl or heteroaryl radical, wherein such aryl or heteroaryl radical may be bonded via an optionally at least mono-substituted C_{1-6}-alkylene group and/or such aryl or heteroaryl radical may be condensed with an optionally at least mono-substituted mono- or polycyclic ring-system, R$^{18}$ represents hydrogen, an unbranched or branched, saturated or unsaturated, optionally at least mono-substituted C_{1-6}-aliphatic radical, a saturated or unsaturated, optionally at least mono-substituted, optionally at least one heteroatom as ring member containing C_{3-8}-alicyclic radical or an optionally at least mono-substituted, 5- or 6-membered aryl or heteroaryl radical, wherein such aryl or heteroaryl radical may be bonded via an optionally at least mono-substituted C_{1-6}-alkylene group and/or such aryl or heteroaryl radical may be condensed with an optionally at least mono-substituted mono- or polycyclic ring-system.

3. Compounds according to claim 1, characterized in that R$^1$, R$^2$, R$^3$, R$^4$ are each independently selected from the group consisting of H, F, Cl, Br, a saturated, branched or unbranched, optionally at least mono-substituted, C_{1-3}-aliphatic radical, a saturated, optionally at least mono-substituted, optionally at least one heteroatom as ring member containing C_5- or C_6-alicyclic radical, which may be bonded via a, optionally at least mono-substituted C$^1$- or C_2-alkylene group, a nitro, cyano, —OR$^{12}$, —OC(=O)R$^{13}$, —SR$^{14}$ and —NR$^{15}$R$^{16}$ moiety.

4. Compounds according to claim 1, characterized in that R$^5$ represents H or a branched or unbranched C_{1-3}-alkyl radical.

5. Compounds according to claim 1, characterized in that R$^6$, R$^7$, R$^8$, R$^9$ are each independently selected from the group consisting of H, a branched or unbranched C_{1-3}-alkyl radical, cyano and a COOR$^{17}$ group.

6. Compounds according to claim 1, characterized in that R$^{10}$ represents hydrogen or a branched or unbranched C_{1-4}-alkyl radical.

7. Compounds according to claim 1, characterized in that R$^{11}$ is selected from the group consisting of unsubstituted phenyl, phenyl optionally at least mono-substituted with a branched or unbranched C_{1-4}-alkyl-radical, a branched or unbranched C_{1-4}-alkoxy-radical, a branched or unbranched C_{1-4}-perfluoroalkyl-radical, a branched or unbranched C_{1-4}-perfluoroalkoxy-radical, F, Cl, Br, cyclohexyl, phenyl, phenoxy, phenylthio, benzoyl, cyano, —C(=O)C_{1-2}-alkyl, —C(=O)OC_{1-2}-alkyl, carboxy, —CH(OH)(phenyl), —NR$^A$R$^B$ wherein R$^A$, R$^B$ are each independently selected from the group consisting of H, a branched or unbranched C_{1-4}-alkyl-radical, —CH_2—CH_2—OH and an unsubstituted phenyl radical, an unsubstituted thiazole radical, a group of general formula (A)

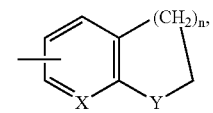

(A)

wherein
n is 1 or 2,
X represents CH or N,
Y represents CH_2, O, N—R$^C$, CH—OH or C(=O),
R$_C$ is H or a branched or unbranched C_{1-4}-alkyl radical, a group of formula (B),

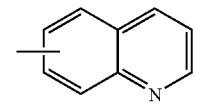

(B)

a group of formula (C),

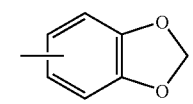

(C)

a group of general formula (D),

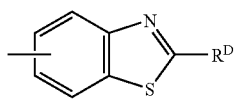

wherein $R_D$ is H or a branched or unbranched $C_{1-4}$-alkyl radical
and a group of general formula (E),

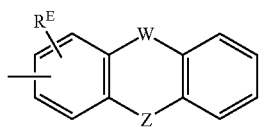

wherein
$R^E$ represents H, a branched or unbranched $C_{1-4}$-alkyl radical or a branched or unbranched $C_{1-4}$-alkoxy radical,
W represents a bond between the two aromatic rings, $CH_2$, CH—OH or C(=O),
Z represents $CH_2$, O, S, CH—OH, C(=O) or N—$R_F$ where $R_F$ represents H or a branched or unbranched $C_{1-4}$-alkyl-radical.

8. Compounds according to claim 1, characterized in that $R^{10}$ and $R^{11}$ together with the bridging nitrogen atom form a saturated, 6-membered heterocyclic ring, which is at least mono-substituted with a methyl radical and/or condensed with an unsubstituted or at least mono-substituted phenyl or cyclohexyl-radical, said phenyl or cyclohexyl radical preferably being at least mono-substituted with F and/or $OCH_3$.

9. Compounds according to claim 1, characterized in that $R^{12}$ represents H, a $C_{1-4}$-alkyl radical, cyclohexyl or a phenyl radical.

10. Compounds according to claim 1, characterized in that $R^{13}$ represents H, a $C_{1-4}$-alkyl radical, cyclohexyl or a phenyl radical.

11. Compounds according to claim 1, characterized in that $R^{14}$ represents H, a $C_{1-4}$-alkyl radical, cyclohexyl or a phenyl radical.

12. Compounds according to claim 1, characterized in that $R^{15}$ and $R^{16}$ are each independently selected from the group consisting of H, a $C_{1-4}$-alkyl radical, cyclohexyl and a phenyl radical.

13. Compounds according to claim 1, characterized in that $R^{17}$ represents H, a $C_{1-4}$-alkyl radical, cyclohexyl or a phenyl radical.

14. Compounds according to claim 1, characterized in that $R^{18}$ represents H, a $C_{1-4}$-alkyl radical or a phenyl radical.

15. Compounds according to claim 1, characterized in that at least two of the residues $R^1$, $R^2$, $R^3$, $R^4$, do not represent hydrogen.

16. Compounds according to claim 1, characterized in that $R^5$ is $CH_3$ or $C_2H_5$.

17. Compounds according to claims 1:

[1] 2-[4-(2-oxo-4H-benzo[d][1,3]oxazin-1-yl)-piperidin-1-yl]-N-(9-oxo-9H-fluoren-2-yl)-acetamide,

[2] 2-[4-(2-oxo-4H-benzo[d][1,3]oxazin-1-yl)-piperidin-1-yl]-N-(9-oxo-9H-fluoren-3-yl)-acetamide),

[3] 2-[4-(2-oxo-4H-benzo[d][1,3]oxazin-1-yl)-piperidin-1-yl]-N-(9-oxo-9H-fluoren-3-yl)-acetamide hydrochloride,

[4] N-(4-benzoyl-phenyl)-2-[4-(2-oxo-4H-benzo[d][1,3]oxazin-1-yl)-piperidin-1-yl]-acetamide,

[5] N-(4-benzoyl-phenyl)-2-[4-(2-oxo-4H-benzo[d][1,3]oxazin-1-yl)-piperidin-1-yl]-acetamide hydrochloride,

[6] 2-[4-(2-oxo-4H-benzo[d][1,3]oxazin-1-yl)-piperidin-1-yl]-N-(5-oxo-5,6,7,8-tetrahidro-naphthalene-2-yl)-acetamide hydrochloride,

[7] 2-[4-(2-oxo-4H-benzo[d][1,3]oxazin-1-yl)-piperidin-1-yl]-N-(9-oxo-9H-fluoren-4-yl)-acetamide hydrochloride,

[8] N-(3-benzoyl-phenyl)-2-[4-(2-oxo-4H-benzo[d][1,3]oxazin-1-yl)-piperidin-1-yl]-acetamide hydrochloride,

[9] 2-[4-(2-oxo-4H-benzo[d][1,3]oxazin-1-yl)-piperidin-1-yl]-N-(1-oxo-indan-5-yl)-acetamide,

[10] 2-[4-(2-oxo-4H-benzo[d][1,3]oxazin-1-yl)-piperidin-1-yl]-N-(1-oxo-indan-5-yl)-acetamide hydrochloride,

[11] N-Indan-5-yl-2-[4-(2-oxo-4H-benzo[d][1,3]oxazin-1-yl)-piperidin-1-yl]-acetamide hydrochloride,

[12] N-(2-Methoxy-dibenzofuran-3-yl)-2-[4-(2-oxo-4H-benzo[d][1,3]oxazin-1-yl)-piperidin-1-yl]-acetamide hydrochloride),

[13] N-(4-Cyclohexyl-phenyl)-2-[4-(2-oxo-4H-benzo[d][1,3]oxazin-1-yl)-piperidin-1-yl]-acetamide hydrochloride,

[14] 1-{1-[2-(3,4-Dihidro-2H-quinolin-1-yl)-2-oxo-ethyl]piperidin-4-yl}-1,4-dihydro-benzo[d][1,3]oxazin-2-one hydrochloride,

[15] 2-[4-(2-oxo-4H-benzo[d][1,3]oxazin-1-yl)-piperidin-1-yl]-N-(9-oxo-9H-fluoren-3-yl)-2-phenyl-acetamide hydrochloride, [16] 2-[4-(2-oxo-4H-benzo[d][1,3]oxazin-1-yl)-piperidin-1-yl]-N-(9-oxo-9H-fluoren-3-yl)-propionamide hydrochloride,

[17] N-(9-Ethyl-9H-carbazol-3-yl)-2-[4-(2-oxo-4H-benzo[d][1,3]oxazin-1-yl)-piperidin-1-yl]-acetamide,

[18] N-(9-Ethyl-9H-carbazol-3-yl)-2-[4-(2-oxo-4H-benzo[d][1,3]oxazin-1-yl)-piperidin-1-yl]-acetamide hydrochloride,

[19] 2-[4-(6-methyl-2-oxo-4H-benzo[d][1,3]oxazin-1-yl)-piperidin-1-yl]-N-(9-oxo-9H-fluoren-3-yl)-acetamide,

[20] 2-[4-(6-methyl-2-oxo-4H-benzo[d][1,3]oxazin-1-yl)-piperidin-1-yl]-N-(9-oxo-9H-fluoren-3-yl)-acetamide hydrochloride,

[21] N-(9-Ethyl-9H-carbazol-3-yl)-2-[4-(6-methyl-2-oxo-4H-benzo[d][1,3]oxazin-1-yl)-piperidin-1-yl]-acetamide hydrochloride,

[22] N-(4-Cyclohexyl-phenyl)-2-[4-(6-methyl-2-oxo-4H-benzo[d][1,3]oxazin-1-yl)-piperidin-1-yl]-acetamide,

[23] N-(4-Cyclohexyl-phenyl)-2-[4-(6-methyl-2-oxo-4H-benzo[d][1,3]oxazin-1-yl)-piperidin-1-yl]-acetamide hydrochloride,

[24] N-(4-benzoyl-phenyl)-2-[4-(6-methyl-2-oxo-4H-benzo[d][1,3]oxazin-1-yl)-piperidin-1-yl]-acetamide hydrochloride,

[25] N-(9-Methyl-9H-carbazol-3-yl)-2-[4-(2-oxo-4H-benzo[d][1,3]oxazin-1-yl)-piperidin-1-yl]-acetamide hydrochloride,

[26] N-(9,10-Dioxo-9,10-dihydro-anthracene-2-yl)-2-[4-(2-oxo-4H-benzo[d][1,3]oxazin-1-yl)-piperidin-1-yl]-acetamide hydrochloride,

[27] N-[4-(Ethyl-phenyl-amino)-phenyl]-2-[4-(2-oxo-4H-benzo[d][1,3]oxazin-1-yl)-piperidin-1-yl]-acetamide hydrochloride,

[28] 2-[4-(6-Methyl-2-oxo-4H-benzo[d][1,3]oxazin-1-yl)-piperidin-1-yl]-N-[4-methyl-phenyl-amino)-phenyl]-acetamide hydrochloride,

[29] 2-[4-(2-oxo-4H-benzo[d][1,3]oxazin-1-yl)-piperidin-1-yl]-N-[4-phenoxy-phenyl]-acetamide hydrochloride,

[30] N-[4-(Isopropyl-phenyl-amino)-phenyl]-2-[4-(2-oxo-4H-benzo[d][1,3]oxazin-1-yl)-piperidin-1-yl]-acetamide hydrochloride,

[31] 3-[4-(2-Oxo-4H-benzo[d][1,3]oxazin-1-yl)-piperidin-1-yl]-N-(9-oxo-9H-fluoren-3-yl)-propionamide hydrochloride,

[32] 2-[4-(6-Chloro-2-oxo-4H-benzo[d][1,3]oxazin-1-yl)-piperidin-1-yl]-N-(9-ethyl-9H-carbazol-3-yl)-acetamide hydrochloride,

[33] N-(4-Chloro-phenyl)-2-[4-(2-oxo-4H-benzo[d][1,3]oxazin-1-yl)-piperidin-1-yl]-acetamide hydrochloride,

[34] 2-[4-(6-Chloro-2-oxo-4H-benzo[d][1,3]oxazin-1-yl)-piperidin-1-yl]-N-(4-chloro-phenyl)-acetamide hydrochloride,

[35] 2-[4-(8-Methyl-2-oxo-4H-benzo[d][1,3]oxazin-1-yl)-piperidin-1-yl]-N-(9-oxo-9H-fluoren-3-yl)-acetamide hydrochloride,

[36] 2-[4-(6-Chloro-2-oxo-4H-benzo[d][1,3]oxazin-1-yl)-piperidin-1-yl]-N-(9-oxo-9H-fluoren-3-yl)-acetamide hydrochloride,

[37] N-(9-Hydroxy-9H-fluoren-3-yl)-2-[4-(8-methyl-2-oxo-4H-benzo[d][1,3]oxazin-1-yl)-piperidin-1-yl]-acetamide hydrochloride,

[38] N-(9-Hydroxy-9H-fluoren-2-yl)-2-[4-(2-oxo-4H-benzo[d][1,3]oxazin-1-yl)-piperidin-1-yl]-acetamide hydrochloride,

[39] 2-[4-(6-Chloro-2-oxo-4H-benzo[d][1,3]oxazin-1-yl)-piperidin-1-yl]-N-(9-hydroxy-9H-fluoren-3-yl)-acetamide hydrochloride,

[40] N-(9-Ethyl-9H-carbazol-3-yl)-2-[4-(8-methyl-2-oxo-4H-benzo[d][1,3]oxazin-1-yl)-piperidin-1-yl]-acetamide hydrochloride,

[41] 2-[4-(8-Methyl-2-oxo-4H-benzo[d][1,3]oxazin-1-yl)-piperidin-1-yl]-N-(4-trifluoromethyl-phenyl)-acetamide hydrochloride,

[42] 2-[4-(8-Methyl-2-oxo-4H-benzo[d][1,3]oxazin-1-yl)-piperidin-1-yl]-N-phenyl-acetamide hydrochloride,

[43] 2-[4-(2-oxo-4H-benzo[d][1,3]oxazin-1-yl)-piperidin-1-yl]-N-(4-trifluoromethyl-phenyl)-acetamide hydrochloride,

[44] 2-[4-(6-Chloro-2-oxo-4H-benzo[d][1,3]oxazin-1-yl)-piperidin-1-yl]-N-phenyl-acetamide hydrochloride,

[45] 2-[4-(6-Chloro-2-oxo-4H-benzo[d][1,3]oxazin-1-yl)-piperidin-1-yl]-N-(4-trifluoromethyl-phenyl)-acetamide hydrochloride,

[46] 2-[4-(2-oxo-4H-benzo[d][1,3]oxazin-1-yl)-piperidin-1-yl]-N-phenyl-acetamide hydrochloride,

[47] N-(4-Chloro-phenyl)-2-[4-(8-Methyl-2-oxo-4H-benzo[d][1,3]oxazin-1-yl)-piperidin-1-yl]-acetamide hydrochloride,

[48] N-(4-Cyano-phenyl)-2-[4-(2-oxo-4H-benzo[d][1,3]oxazin-1-yl)-piperidin-1-yl]-acetamide hydrochloride,

[49] N-(4-Cyano-phenyl)-2-[4-(8-methyl-2-oxo-4H-benzo[d][1,3]oxazin-1-yl)-piperidin-1-yl]-acetamide hydrochloride,

[50] 2-[4-(6-Chloro-2-oxo-4H-benzo[d][1,3]oxazin-1-yl)-piperidin-1-yl]-N-(4-cyano-phenyl)-acetamide hydrochloride,

[51] N-(4-Acethyl-phenyl)-2-[4-(2-oxo-4H-benzo[d][1,3]oxazin-1-yl)-piperidin-1-yl]-acetamide hydrochloride,

[52] 2-[4-(8-Methyl-2-oxo-4H-benzo[d][1,3]oxazin-1-yl)-piperidin-1-yl]-N-(4-phenoxy-phenyl)-acetamide hydrochloride,

[53] N-(4-Acethyl-phenyl)-2-[4-(6-chloro-2-oxo-4H-benzo[d][1,3]oxazin-1-yl)-piperidin-1-yl]-acetamide hydrochloride,

[54] N-(4-Acethyl-phenyl)-2-[4-(8-methyl-2-oxo-4H-benzo[d][1,3]oxazin-1-yl)-piperidin-1-yl]-acetamide hydrochloride,

[55] 2-[4-(6-Chloro-2-oxo-4H-benzo[d][1,3]oxazin-1-yl)-piperidin-1-yl]-N-(4-phenoxy-phenyl)-acetamide hydrochloride,

[56] N-(4-Benzoyl-phenyl)-2-[4-(8-methyl-2-oxo-4H-benzo[d][1,3]oxazin-1-yl)-piperidin-1-yl]-acetamide hydrochloride,

[57] N-(4-Benzoyl-phenyl)-2-[4-(6-chloro-2-oxo-4H-benzo[d][1,3]oxazin-1-yl)-piperidin-1-yl]-acetamide hydrochloride,

[58] N-(2-Chloro-phenyl)-2-[4-(6-methyl-2-oxo-4H-benzo[d][1,3]oxazin-1-yl)-piperidin-1-yl]-acetamide,

[59] 2-[4-(6-Methyl-2-oxo-4H-benzo[d][1,3]oxazin-1-yl)-piperidin-1-yl]-N-(2-trifluoromethyl-phenyl)-acetamide,

[60] 2-[4-(6-Methyl-2-oxo-4H-benzo[d][1,3]oxazin-1-yl)-piperidin-1-yl]-N-phenyl-acetamide,

[61] N-(4-Cyclohexyl-phenyl)-2-[4-(8-methyl-2-oxo-4H-benzo[d][1,3]oxazin-1-yl)-piperidin-1-yl]-acetamide hydrochloride,

[62] 2-[4-(6-Chloro-2-oxo-4H-benzo[d][1,3]oxazin-1-yl)-piperidin-1-yl]-N-(4-cyclohexyl-phenyl)-acetamide hydrochloride,

[63] N-(2-Benzoyl-phenyl)-2-[4-(2-oxo-4H-benzo[d][1,3]oxazin-1-yl)-piperidin-1-yl]-acetamide hydrochloride,

[64] N-(2-Benzoyl-phenyl)-2-[4-(8-methyl-2-oxo-4H-benzo[d][1,3]oxazin-1-yl)-piperidin-1-yl]-acetamide hydrochloride,

[65] N-(2-Benzoyl-phenyl)-2-[4-(6-chloro-2-oxo-4H-benzo[d][1,3]oxazin-1-yl)-piperidin-1-yl]-acetamide hydrochloride,

[66] N-(2-Benzoyl-phenyl)-2-[4-(6-methyl-2-oxo-4H-benzo[d][1,3]oxazin-1-yl)-piperidin-1-yl]-acetamide,

[67] 2-[4-(6-Methyl-2-oxo-4H-benzo[d][1,3]oxazin-1-yl)-piperidin-1-yl]-N-(4-phenoxy-phenyl)-acetamide hydrochloride,

[68] N-(4-Acethyl-phenyl)-2-[4-(6-methyl-2-oxo-4H-benzo[d][1,3]oxazin-1-yl)-piperidin-1-yl]-acetamide hydrochloride,

[69] N-(9-Hydroxy-9H-fluoren-3-yl)-2-[4-(2-oxo-4H-benzo[d][1,3]oxazin-1-yl)-piperidin-1-yl]-acetamide hydrochloride,

[70] 2-[4-(6-Chloro-2-oxo-4H-benzo[d][1,3]oxazin-1-yl)-piperidin-1-yl]-N-(9-oxo-9H-fluoren-2-yl)-acetamide hydrochloride,

[71] 2-[4-(6-Methyl-2-oxo-4H-benzo[d][1,3]oxazin-1-yl)-piperidin-1-yl]-N-(9-oxo-9H-fluoren-2-yl)-acetamide hydrochloride,

[72] 2-[4-(8-Methyl-2-oxo-4H-benzo[d][1,3]oxazin-1-yl)-piperidin-1-yl]-N-(9-oxo-9H-fluoren-2-yl)-acetamide hydrochloride,

[73] 2-[4-(6-Chloro-2-oxo-4H-benzo[d][1,3]oxazin-1-yl)-piperidin-1-yl]-N-(9-hydroxy-9H-fluoren-2-yl)-acetamide hydrochloride,

[74] N-(9-Hydroxy-9H-fluoren-2-yl)-2-[4-(6-methyl-2-oxo-4H-benzo[d][1,3]oxazin-1-yl)-piperidin-1-yl]-acetamide hydrochloride,

[75] N-(9-Hydroxy-9H-fluoren-2-yl)-2-[4-(8-methyl-2-oxo-4H-benzo[d][1,3]oxazin-1-yl)-piperidin-1-yl]-acetamide hydrochloride,

[76] N-(9-Hydroxy-9H-fluoren-3-yl)-2-[4-(6-methyl-2-oxo-4H-benzo[d][1,3]oxazin-1-yl)-piperidin-1-yl]-acetamide hydrochloride,

[77] N-(4-Cyclohexyl-phenyl)-2-[4-(7-fluoro-2-oxo-4H-benzo[d][1,3]oxazin-1-yl)-piperidin-1-yl]-acetamide hydrochloride,

[78] N-(9-Ethyl-9H-carbazol-3-yl)-2-[4-(5-fluoro-2-oxo-4H-benzo[d][1,3]oxazin-1-yl)-piperidin-1-yl]-acetamide hydrochloride,

[79] N-(9-Ethyl-9H-carbazol-3-yl)-2-[4-(6-metoxy-2-oxo-4H-benzo[d][1,3]oxazin-1-yl)-piperidin-1-yl]-acetamide hydrochloride,

[80] N-(9-Ethyl-9H-carbazol-3-yl)-2-[4-(7-methyl-2-oxo-4H-benzo[d][1,3]oxazin-1-yl)-piperidin-1-yl]-acetamide hydrochloride,

[81] 2-[4-(5-Chloro-2-oxo-4H-benzo[d][1,3]oxazin-1-yl)-piperidin-1-yl]-N-(9-ethyl-9H-carbazol-3-yl)acetamide hydrochloride,

[82] 2-[4-(5-Fluoro-2-oxo-4H-benzo[d][1,3]oxazin-1-yl)-piperidin-1-yl]-N-(4-phenoxy-phenyl)-acetamide hydrochloride,

[83] 2-[4-(6-metoxy-2-oxo-4H-benzo[d][1,3]oxazin-1-yl)-piperidin-1-yl]-N-(9-oxo-9H-fluoren-3-yl)-acetamide,

[84] N-Dibenzofuran-2-yl-2-[4-(8-metoxy-2-oxo-4H-benzo[d][1,3]oxazin-1-yl)-piperidin-1-yl]-acetamide,

[85] 2-[4-(7-Chloro-2-oxo-4H-benzo[d][1,3]oxazin-1-yl)-piperidin-1-yl]-N-dibenzofuran-2-yl-acetamide,

[86] 2-[4-(6-Fluoro-2-oxo-4H-benzo[d][1,3]oxazin-1-yl)-piperidin-1-yl]-N-(9-oxo-9H-fluoren-3-yl)-acetamide,

[87] 2-[4-(7-Fluoro-2-oxo-4H-benzo[d][1,3]oxazin-1-yl)-piperidin-1-yl]-N-(9-hydroxy-9H-fluoren-3-yl)-acetamide,

[88] N-(9H-Carbazol-3-yl)-2-[4-(5-methyl-2-oxo-4H-benzo[d][1,3]oxazin-1-yl)-piperidin-1-yl]-acetamide,

[89] N-(9H-Carbazol-3-yl)-2-[4-(5-fluoro-2-oxo-4H-benzo[d][1,3]oxazin-1-yl)-piperidin-1-yl]-acetamide,

[90] N-(9H-carbazol-3-yl)-2-[4-(6-methoxy-2-oxo-4H-benzo[d][1,3]oxazin-1-yl)-piperidin-1-yl]-acetamide,

[91] N-(9H-Ethyl-9H-carbazol-3-yl)-2-[4-(5-methoxy-2-oxo-4H-benzo[d][1,3]oxazin-1-yl)-piperidin-1-yl]-acetamide,

[92] 2-[4-(5-methoxy-2-oxo-4H-benzo[d][1,3]oxazin-1-yl)-piperidin-1-yl]-N-(4-phenoxy-phenyl(-acetamide,

[93] N-(9H-Hydroxy-9H-fluoren-3-yl)-2-[4-(7-methyl-2-oxo-4H-benzo[d][1,3]oxazin-1-yl)-piperidin-1-yl]-acetamide,

[94] N-(9H-Hydroxy-9H-fluoren-3-yl)-2-[4-(8-methoxy-2-oxo-4H-benzo[d][1,3]oxazin-1-yl)-piperidin-1-yl]-acetamide,

[95] N-Dibenzofuran-2-yl-2-[4-(5-methyl-2-oxo-4H-benzo[d][1,3]oxazin-1-yl)-piperidin-1-yl]-acetamide,

[96] N-[4-(Ethyl-phenyl-amino)-phenyl]-2-[4-(7-methyl-2-oxo-4H-benzo[d][1,3]oxazin-1-yl)-piperidin-1-yl]-acetamide,

[97] N-(9H-Carbazol-3-yl)-2-[4-(8-chloro-2-oxo-4H-benzo[d][1,3]oxazin-1-yl)-piperidin-1-yl]-acetamide,

[98] N-[4-(Ethyl-phenyl-amino)-phenyl]-2-[4-(8-methoxy-2-oxo-4H-benzo[d][1,3]oxazin-1-yl)-piperidin-1-yl]-acetamide,

[99] N-(9-Hydroxy-9H-fluoren-4-yl)-2-[4-(2-oxo-4H-benzo[d][1,3]oxazin-1-yl)-piperidin-1-yl]-acetamide,

[100] N-[4-(Hydroxy-phenyl-methyl)-phenyl-2-[4-(2-oxo-4H-benzo[d][1,3]oxazin-1-yl)-piperidin-1-yl]-acetamide,

[101] N-[4-Chloro-2-(chloro-benzoyl)-phenyl]-2-[4-(6methyl-2-oxo-4H-benzo[d][1,3]oxazin-1-yl)-piperidin-1-yl]-acetamide,

[102] N-[4-Chloro-2-(2-chloro-benzoyl)-phenyl]-2-[4-(2-oxo-4H-benzo[d][1,3]oxazin-1-yl)-piperidin-1-yl]-acetamide hydrochloride,

[103] N-[4-Chloro-2-(2-chloro-benzoyl)-phenyl]-2-[4-(8-methyl-2-oxo-4H-benzo[d][1,3]oxazin-1-yl)-piperidin-1-yl]-acetamide hydrochloride,

[104] N-[4-Chloro-2-(2-chloro-benzoyl)-phenyl]-2-[4-(6-chloro-2-oxo-4H-benzo[d][1,3]oxazin-1-yl)-piperidin-1-yl]-acetamide hydrochloride,

[105] 2-[4-(7-Methyl-2-oxo-4H-benzo[d][1,3]oxazin-1-yl)-piperidin-1-yl]-N-thiazole-2-yl-acetamide,

[106] 2-[4-(6-Fluoro-2-oxo-4H-benzo[d][1,3]oxazin-1-yl)-piperidin-1-yl]-N-thiazole-2-yl-acetamide,

[107] N-dibenzothiophene-2-yl-2-[4-(5-methoxy-2-oxo-4H-benzo[d][1,3]oxazin-1-yl)-piperidin-1-yl]-acetamide,

[108] 2-[4-(7-Chloro-2-oxo-4H-benzo[d][1,3]oxazin-1-yl)-piperidin-1-yl]-N-dibenzothiophene-2-yl-acetamide,

[109] 2-[4-(5-Hydroxy-2-oxo-4H-benzo[d][1,3]oxazin-1-yl)-piperidin-1-yl]-N-(4-phenoxy-phenyl)-acetamide,

[110] 1-{2-[2-(3,4-Dihydro-1H-isoquinoline-2-yl)-2-oxo-ethyl]-piperidin-4-yl}-1,4-dihydro-benzo[d][1,3]oxazin-2-one hydrochloride,

[111] 2-[4-(6-Fluoro-2-oxo-4H-benzo[d][1,3]oxazin-1-yl)-piperidin-1-yl]-N-quinoline-6-yl-acetamide,

[112] 2-[4-(6-Methoxy-2-oxo-4H-benzo[d][1,3]oxazin-1-yl)-piperidin-1-yl]-N-quinoline-6-yl-acetamide,

[113] 2-[4-(6-Chloro-2-oxo-4H-benzo[d][1,3]oxazin-1-yl)-piperidin-1-yl]-N-quinoline-6-yl-acetamide,

[114] 2-[4-(6-Fluoro-2-oxo-4H-benzo[d][1,3]oxazin-1-yl)-piperidin-1-yl]-N-(2-methyl-benzothiazole-5-yl)-acetamide,

[115] 2-[4-(6-Chloro-2-oxo-4H-benzo[d][1,3]oxazin-1-yl)-piperidin-1-yl]-N-(2-methyl-benzothiazole-5-yl)-acetamide,

[116] 2-[4-(6-Methoxy-2-oxo-4H-benzo[d][1,3]oxazin-1-yl)-piperidin-1-yl]-N-(2-methyl-benzothiazole-5-yl)-acetamide,

[117] N-(3-Dimethylamino-phenyl)-2-[4-(2-oxo-4H-benzo[d][1,3]oxazin-1-yl)-piperidin-1-yl]-acetamide,

[118] N-(4-Dimethylamino-phenyl)-2-[4-(2-oxo-48 d][1,3]oxazin-1-yl)-piperidin-1-yl]-acetamide,

[119] N-(3-Dimethylamino-phenyl)-2-[4-(8-methyl-2-oxo-4H-benzo[d][1,3]oxazin-1-yl)-piperidin-1-yl]-acetamide,

[120] N-(4-Dimethylamino-phenyl)-2-[4-(8-methyl-2-oxo-4H-benzo[d][1,3]oxazin-1-yl)-piperidin-1-yl]-acetamide,

[121] N-(3-Dimethylamino-phenyl)-2-[4-(6-methyl-2-oxo-4H-benzo[d][1,3]oxazin-1-yl)-piperidin-1-yl]-acetamide,

[122] N-(4-Dimethylamino-phenyl)-2-[4-(6-methyl-2-oxo-4H-benzo[d][1,3]oxazin-1-yl)-piperidin-1-yl]-acetamide,

[123] N-(4-Dimethylamino-phenyl)-2-[4-(2-oxo-4H-benzo[d][1,3]oxazin-1-yl)-piperidin-1-yl]-acetamide,

[124] 2-{2-[4-(2-Oxo-4H-benzo[d][1,3]oxazin-1-yl)-piperidin-1-yl]-acethylamino}-benzoic acid methyl ester,

[125] 2-{2-[4-(8-Methyl-2-oxo-4H-benzo[d][1,3]oxazin-1-yl)-piperidin-1-yl]-acethylamino}-benzoic acid methyl ester,

[126] N-(2-Methoxy-dibenzofuran-3-yl)-2-[4-(2-oxo-4H-benzo[d][1,3]oxazin-1-yl)-piperidin-1-yl]-acetamide hydrochloride,

[127] N-(2-[4-(6-Chloro-2-oxo-4H-benzo[d][1,3]oxazin-1-yl)-piperidin-1-yl]-N-(2-methoxy-dibenzofuran-3-yl-acetamide hydrochloride,

[128] 2-{2-[4-(6-Chloro-2-oxo-4H-benzo[d][1,3]oxazin-1-yl)-piperidin-1-yl]-acethylamino}-benzoic acid methyl ester,

[129] 2-{2-[4-(6-Methyl-2-oxo-4H-benzo[d][1,3]oxazin-1-yl)-piperidin-1-yl]-acethylamino}-benzoic acid methyl ester,

[130] 2-[4-(6-Chloro-2-oxo-4H-benzo[d][1,3]oxazin-1-yl)-piperidin-1-yl]-N-(4-diethylamino-phenyl)-acetamide dihydrochloride,

[131] 2-[4-(6-Chloro-2-oxo-4H-benzo[d][1,3]oxazin-1-yl)-piperidin-1-yl]-N-{4-[ethyl-(2-hydroxy-ethyl)-amino]-phenyl}acetamide dihydrochloride,

[132] N-{4-[Ethyl-(2-hydroxy-ethyl)-amino]-phenyl}-2-[4-(6-methyl-2-oxo-4H-benzo[d][1,3]oxazin-1-yl)-piperidin-1yl]-acetamide dihydrochloride,

[133] N-(4-Diethylamino-phenyl)-2-[4-(6-methyl-2-oxo-4H-benzo[d][1,3]oxazin-1-yl)-piperidin-1-yl]-acetamide dihydrochloride,

[134] N-(4-Diethylamino-phenyl)-2-[4-(8-methyl-2-oxo-4H-benzo[d][1,3]oxazin-1-yl)-piperidin-1-yl]-acetamide dihydrochloride,

[135] N-(4-[ethyl-(2-hydroxy-ethyl)-amino]-phenyl)-2-[4-(8-methyl-2-oxo-4H-benzo[d][1,3]oxazin-1-yl)-piperidin-1-yl]-acetamide dihydrochloride,

[136] N-Benzo[1,3]dioxol-5-yl-2-[4-(2-oxo-4H-benzo[d][1,3]oxazin-1-yl)-piperidin-1-yl]-acetamide,

[137] N-Benzo[1,3]dioxol-5-yl-2-[4-(6-methyl-2-oxo-4H-benzo[d][1,3]oxazin-1-yl)-piperidin-1-yl]-acetamide,

[138] N-Benzo[1,3]dioxol-5-yl-2-[4-(6-chloro-2-oxo-4H-benzo[d][1,3]oxazin-1-yl)-piperidin-1-yl]-acetamide,

[139] N-Benzo[1,3]dioxol-5-yl-2-[4-(8-methyl-2-oxo-4H-benzo[d][1,3]oxazin-1-yl)-piperidin-1-yl]-acetamide,

[140] N-{4-[ethyl-(2-hydroxy-ethyl)-amino]-phenyl}-2-[4-(2-oxo-4H-benzo[d][1,3]oxazin-1-yl)-piperidin-1-yl]-acetamide dihydrochloride,

[141] 2-[4-(6-Chloro-2-oxo-4H-benzo[d][1,3]oxazin-1-yl)-piperidin-1-yl]-N-(4-dimethylamino-phenyl)-acetamide dihydrochloride,

[142] N-(9-Ethyl-9H-carbazol-3-yl)-2-[4-(4-methyl-2-oxo-4H-benzo[d][1,3]oxazin-1-yl)-piperidin-1-yl]-acetamide,

[143] N-(9-Ethyl-9H-carbazol-3-yl)-2-[4-(4-methyl-2-oxo-4H-benzo[d][1,3]oxazin-1-yl)-piperidin-1-yl]-acetamide,

[144] 2-[4-(4-Methyl-2-oxo-4H-benzo[d][1,3]oxazin-1-yl)-piperidin-1-yl]-N-(4-phenoxy-phenyl)-acetamide,

[145] 2-{2-[4-(2-Oxo-4H-benzo[d][1,3]oxazin-1-yl)-piperidin-1-yl]-acetamino}-benzoic acid,

[146] 1-{1-[2-(6-Fluoro-2-methyl-3,4-dihydro-2H-quinoline-1-yl)-2-oxo-ethyl]-piperidin-4-yl}-1,4-dihydro-benzo[d][1,3]oxazin-2-one,

[147] 6-Chloro-1-{1-[2-(6-Fluoro-2-methyl-3,4-dihydro-2H-quinoline-1-yl)-2-oxo-ethyl]-piperidin-4-yl}-1,4-dihydro-benzo[d][1,3]oxazin-2-one,

[148] 1-{1-[2-(6-Fluoro-2-methyl-3,4-dihydro-2H-quinoline-1-yl)-2-oxo-ethyl]-piperidin-4-yl}-6-methyl-1,4-dihydro-benzo[d][1,3]oxazin-2-one,

[149] 1-{1-[2-(6-Fluoro-2-methyl-3,4-dihydro-2H-quinoline-1-yl)-2-oxo-ethyl]-piperidin-4-yl}-8-methyl-1,4-dihydro-benzo[d][1,3]oxazin-2-one,

[150] 1-{1-[2-(6-Methoxy-2,2,4-trimethyl-3,4-dihydro-2H-quinoline-1-yl)-2-oxo-ethyl]-piperidin-4-yl}-1,4dihydro-benzo[d][1,3]oxazin-2-one;

[151] 6-Chloro-1-{1-[2-(6-methoxy-2,2,4-trimethyl-3,4-dihydro-2H-quinoline-1-yl)-2-oxo-ethyl]-piperidin-4-yl}-1,4-dihydro-benzo[d][1,3]oxazin-2-one,

[152] 1-{1-[2-(6-Methoxy-2,2,4-trimethyl-3,4-dihydro-2H-quinoline-1-yl)-2-oxo-ethyl]-piperidin-4-yl}-8-methyl-1,4-dihydro-benzo[d][1,3]oxazin-2-one,

[153] 1-{1-[2-(6-Methoxy-2,2,4-trimethyl-3,4-dihydro-2H-quinoline-1-yl)-2-oxo-ethyl]-piperidin-4-yl}-6-methyl-1,4-dihydro-benzo[d][1,3]oxazin-2-one,

[154] N-(9-Hydroxy-9H-fluoren-3-yl)-2-[4-(2-oxo-7-trifluormethyl-4H-benzo[d][1,3]oxazin-1-yl)-piperidin-1-yl]-acetamide,

[155] N-(9-carbazol-3-yl)-2-[4-(2-oxo-7-trifluormethyl-4H-benzo[d][1,3]oxazin-1-yl)-piperidin-1-yl]-acetamide,

[156] 2-[4-(2-Oxo-7-trifluormethyl-4H-benzo[d][1,3]oxazin-1-yl)-piperidin-1-yl]-N-(4-phenoxy-phenyl)-acetamide,

[157] N-(9-Ethyl-9H-carbazol-3-yl)-2-[4-(2-oxo-7-trifluormethyl-4H-benzo[d][1,3]oxazin-1-yl)-piperidin-1-yl]-acetamide,

[158] 2-4-(6,7-Difluoro-2-oxo-4H-benzo[d][1,3]oxazin-1-yl)-piperidin-1-yl]-N-(9-hydroxy-9H-fluoren-3-yl)-acetamide,

[159] N-(9H-carbazol-3-yl)-2-[4-(6,7-difluoro-2-oxo-4H-benzo[d][1,3]oxazin-1-yl)-piperidin-1-yl]-acetamide,

[160] 2-4-(6,7-Difluoro-2-oxo-4H-benzo[d][1,3]oxazin-1-yl)-piperidin-1-yl]-N-(4-phenoxy-phenyl)-acetamide,

[161] 2-4-(6,7-Difluoro-2-oxo-4H-benzo[d][1,3]oxazin-1-yl)-piperidin-1-yl]-N-(9-ethyl-9H-carbazol-3-yl)-acetamide,

[162] 2-[4-(4-Methyl-2-oxo-4H-benzo[d][1,3]oxazin-1-yl)-piperidin-1-yl]-N-(9-oxo-9H-fluoren-3-yl)-acetamide,

[163] 2-[4-(6-Chloro-2-oxo-4H-benzo[d][1,3]oxazin-1-yl)-piperidin-1-yl]-N-(3-dimethylamino-phenyl)-acetamide.

18. Medicament comprising at least one benzoxazinone-derived compound according to claim 1, optionally in form of one of its stereoisomers, its racemate or in form of a mixture of at least two of its stereoisomers in any mixing ration, or a physiologically acceptable salt thereof, or a solvate, respectively, and optionally one or more pharmaceutically acceptable adjuvants.

19. Compounds according to claim 1 where the stereoisomers are enantiomers or diastereomers.

20. Compounds according to claim 3, where $R^1$, $R^2$, $R^3$, $R^4$ are each independently selected from the group consisting of H, F, Cl, $CH_3$, $CH_2CH_3$, $CF_3$, $CF_2CF_3$, cyclopentyl, cyclohexyl, nitro, cyano and —$OR^{12}$.

21. Compounds according to claim 4, where $R^5$ represents H, $CH_3$ or $CH_2CH_3$.

22. Compounds according to claim 5, where $R^6$, $R^7$, $R^8$, $R^9$ are each independently selected from the group consisting of H, $CH_3$, $CH_2CH_3$ and cyano.

23. Compounds according to claim 9, where $R^{12}$ represents H, $CH_3$, $C_2H_5$ or phenyl.

24. Compounds according to claim 10, where $R^{13}$ represents H, $CH_3$, $C_2H_5$ or phenyl.

25. Compounds according to claim 11, where $R^{14}$ represents H, $CH_3$, $C_2H_5$ or phenyl.

26. Compounds according to claim 12, where $R^{15}$ and $R^{16}$ are each independently selected from the group consisting of H, $CH_3$, $C_2H_5$ and phenyl.

27. Compounds according to claim 13, where $R^{17}$ represents H, $CH_3$, $C_2H_5$ or phenyl.

28. Compounds according to claim 14, where $R^{18}$ represents H, $CH_3$ or phenyl.

29. Compounds according to claim 15, where $R^2$ and $R^3$, do not represent hydrogen.

30. Process for the preparation of benzoxazinone-derived compounds according to claim 1, characterized in that at least one compound of formula (II),

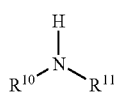
(II)

wherein $R^{10}$ and $R^{11}$ have the meaning according to claim 1 is reacted with at least one compound of formula (III),

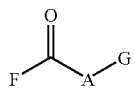
(III)

wherein A has the meaning according to claim 1, F represents halogen, hydroxy or an O-acyl group and G represents halogen, in a suitable reaction medium and in the presence of at least one base and/or at least one auxiliary agent, and reacting the so obtained compound of formula (IV)

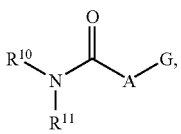
(IV)

wherein A, G, $R^{10}$ and $R^{11}$ have the above defined meaning, with at least one piperidine compound of formula (V) and/or a salt thereof,

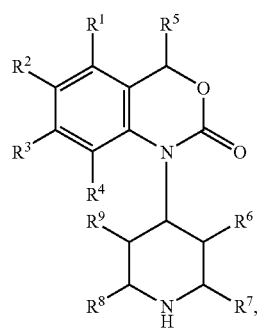
(V)

wherein $R^1$ to $R^9$ have the meaning according to claim 1, in a suitable reaction medium, optionally in the presence of at least one base and/or at least one auxiliary agent.

31. Process for the preparation of a physiologically acceptable salt of the benzoxazinone-derived compounds according to claim 1, characterized in that at least one compound of formula (I) having at least one basic group is reacted with at least one acid, optionally in the presence of a suitable reaction medium.

32. Process for the preparation of a physiologically acceptable salt of the benzoxazinone-derived compounds according to claim 1, characterized in that at least one compound of formula (I) having at least one acidic group is reacted with at least one base, optionally in the presence of a suitable reaction medium.

* * * * *